US011149089B2

(12) United States Patent
Holz et al.

(10) Patent No.: US 11,149,089 B2
(45) Date of Patent: *Oct. 19, 2021

(54) METHOD FOR TREATING RHEUMATOID ARTHRITIS BY ADMINISTERING IL-6 RECEPTOR ANTIBODIES

(71) Applicant: Ablynx N.V., Ghent-Zwijnaarde (BE)

(72) Inventors: Josefin-Beate Holz, Munich (DE); Stefaan Rossenu, Lovendegem (BE); Steven De Bruyn, Baal (BE); Maria-Laura Sargentini-Maier, Brussels (BE); Özkan Yalkinoglu, Wuppertal (DE)

(73) Assignee: Ablynx N.V., Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/149,355

(22) Filed: Oct. 2, 2018

(65) Prior Publication Data

US 2019/0119393 A1    Apr. 25, 2019

Related U.S. Application Data

(62) Division of application No. 14/345,702, filed as application No. PCT/EP2012/068765 on Sep. 24, 2012, now Pat. No. 10,138,302.

(60) Provisional application No. 61/664,337, filed on Jun. 26, 2012, provisional application No. 61/604,774, filed on Feb. 29, 2012, provisional application No. 61/538,500, filed on Sep. 23, 2011.

(51) Int. Cl.
| *A61K 39/395* | (2006.01) |
| *C07K 16/28* | (2006.01) |
| *C07K 14/54* | (2006.01) |
| *C07K 14/715* | (2006.01) |

(52) U.S. Cl.
CPC ...... *C07K 16/2866* (2013.01); *C07K 14/5412* (2013.01); *C07K 14/7155* (2013.01); *C07K 2317/22* (2013.01); *C07K 2317/569* (2013.01)

(58) Field of Classification Search
CPC .................................................. A61K 39/3955
See application file for complete search history.

(56) References Cited

U.S. PATENT DOCUMENTS

| 5,116,964 | A | 5/1992 | Capon et al. |
| 5,888,510 | A | 3/1999 | Kishimoto et al. |
| 6,261,560 | B1 | 7/2001 | Tsujinaka et al. |
| 6,664,374 | B1 | 12/2003 | Saxinger |
| 8,629,244 | B2 | 1/2014 | Kolkman et al. |
| 8,748,581 | B2 | 6/2014 | Beirnaert et al. |
| 8,962,805 | B2 | 2/2015 | Beirnaert et al. |
| 9,181,350 | B2 | 11/2015 | Beirnaert et al. |
| 9,273,150 | B2 | 3/2016 | Beirnaert et al. |
| 9,605,072 | B2 | 3/2017 | Kolkman et al. |
| 9,611,326 | B2 | 4/2017 | Kolkman et al. |
| 9,617,341 | B2 | 4/2017 | Kolkman et al. |
| 10,118,967 | B2 * | 11/2018 | Hoefman ............ C07K 16/2866 |
| 10,138,302 | B2 * | 11/2018 | Holz .................. C07K 16/2866 |
| 10,392,440 | B2 | 8/2019 | Beirnaert et al. |
| 10,618,964 | B2 | 4/2020 | Compernolle et al. |
| 10,618,966 | B2 | 4/2020 | Kolkman et al. |
| 2005/0089932 | A1 | 4/2005 | Kolkman et al. |
| 2005/0142635 | A1 | 6/2005 | Tsuchiya et al. |
| 2007/0036785 | A1 | 2/2007 | Kishimoto et al. |
| 2007/0280945 | A1 | 12/2007 | Stevens et al. |
| 2010/0215664 | A1 | 8/2010 | Kolkman et al. |
| 2011/0243954 | A1 | 10/2011 | Revets et al. |
| 2012/0077731 | A1 | 3/2012 | Beirnaert et al. |
| 2012/0171209 | A1 | 7/2012 | Compernolle et al. |
| 2012/0244158 | A1 | 9/2012 | Brige et al. |
| 2014/0212417 | A1 | 7/2014 | Holz et al. |
| 2014/0221623 | A1 | 8/2014 | Kolkman et al. |
| 2014/0329278 | A1 | 11/2014 | Beirnaert et al. |
| 2014/0343257 | A1 | 11/2014 | Beirnaert et al. |
| 2014/0348830 | A1 | 11/2014 | Beimaert et al. |
| 2014/0349342 | A1 | 11/2014 | Kolkman et al. |
| 2015/0037338 | A1 | 2/2015 | Beirnaert et al. |
| 2015/0050268 | A9 | 2/2015 | Holz et al. |
| 2016/0326252 | A1 | 11/2016 | Hoefman et al. |

(Continued)

FOREIGN PATENT DOCUMENTS

| CN | 1535728 A | 10/2004 |
| EP | 0 257 406 A2 | 3/1988 |

(Continued)

OTHER PUBLICATIONS

[No Author Listed], Ablynx initiates Phase I bioavailability study with subcutaneous formulation of its anti-IL-6R Nanobody partnered with AbbVie. GlobeNewswire. Apr. 23, 2014, p. 3pp.

[No Author Listed], Ablynx Reports Positive Phase I Data for ALX-0061 in Rheumatoid Arthritis. Press release. Ablynx. Ghent, Belgium. Nov. 30, 2011.

[No Author Listed], Ablynx's anti-IL-6R Nanobody partnered with AbbVie demonstrates a bioavailability of more than 80% after subcutaneous injection. GlobeNewswire. Oct. 23, 2014; p. 3pp.

[No Author Listed], Ablynx's anti-IL-6R Nanobody, ALX-0061, shows excellent 24 week safety and efficacy results in a phase II clinical trial in rheumatoid arthritis. Feb. 13, 2013. Ghent, Belgium.

(Continued)

*Primary Examiner* — Prema M Mertz

(74) *Attorney, Agent, or Firm* — Wolf, Greenfield & Sacks, P.C.

(57) ABSTRACT

Polypeptides are provided directed against IL-6R at specific dose ranges and dosing schedules that result in a prolonged effect on IL-6 mediated signaling. In particular, the invention provides pharmacologically active agents, compositions, methods and/or dosing schedules that have certain advantages compared to the agents, compositions, methods and/or dosing schedules that are currently used and/or known in the art, including the ability to dose less frequently or to administer lower doses to obtain equivalent effects in inhibiting IL-6 mediated signaling.

19 Claims, 8 Drawing Sheets

Figure 1:
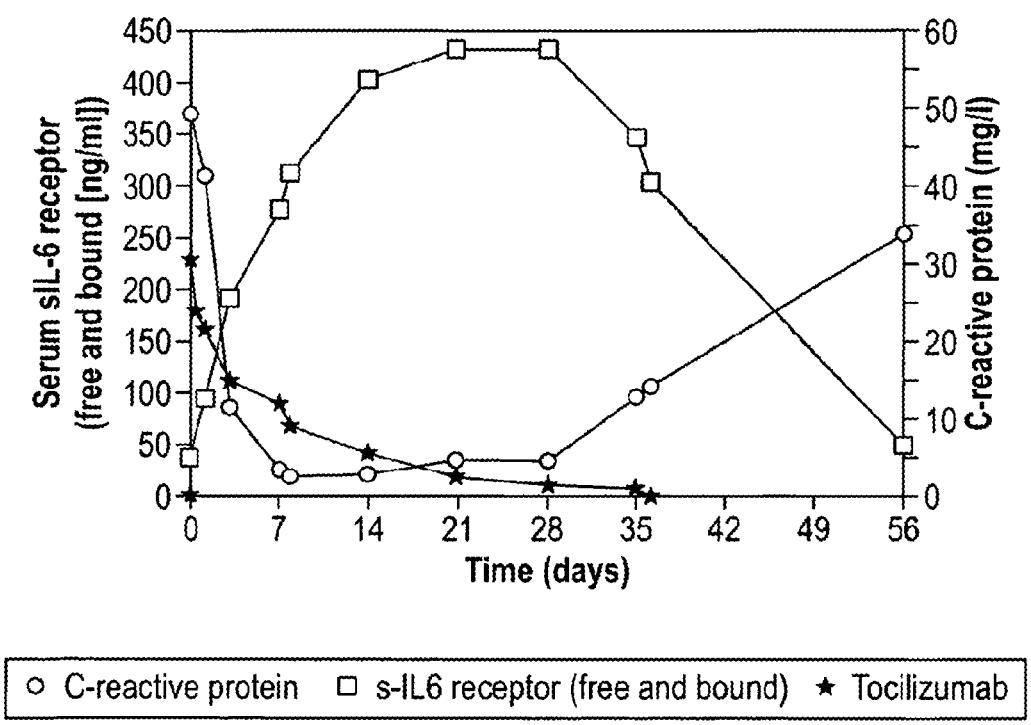

Specification includes a Sequence Listing.

(56) References Cited

U.S. PATENT DOCUMENTS

| | | | |
|---|---|---|---|
| 2016/0333099 | A1 | 11/2016 | Beirnaert et al. |
| 2018/0016342 | A1 | 1/2018 | Kolkman et al. |
| 2019/0119392 | A1 | 4/2019 | Hoefman et al. |

FOREIGN PATENT DOCUMENTS

| | | | |
|---|---|---|---|
| EP | 0 312 996 A2 | 4/1989 | |
| EP | 0 325 474 A2 | 7/1989 | |
| EP | 0 409 607 A2 | 1/1991 | |
| EP | 0 411 946 A2 | 2/1991 | |
| EP | 0 527 809 A1 | 2/1993 | |
| EP | 0 572 118 A1 | 12/1993 | |
| EP | 0 628 639 B1 | 12/1994 | |
| EP | 0 409 607 B1 | 10/1996 | |
| JP | 2000/500644 | 1/2000 | |
| WO | WO 1997/13781 A2 | 4/1997 | |
| WO | WO 2005/003345 A2 | 1/2005 | |
| WO | WO 2006/023144 A2 | 3/2006 | |
| WO | WO 2006/079372 A1 | 8/2006 | |
| WO | WO 2007/042289 A2 | 4/2007 | |
| WO | WO 2007/104529 A2 | 9/2007 | |
| WO | WO 2008/020079 A1 | 2/2008 | |
| WO | WO 2008/071685 A1 | 6/2008 | |
| WO | WO 2008/074840 A2 | 6/2008 | |
| WO | WO 2008/077945 A2 | 7/2008 | |
| WO | WO 2009/004065 A2 | 1/2009 | |
| WO | WO 2009/010539 A2 | 1/2009 | |
| WO | WO 2009/095489 A2 | 8/2009 | |
| WO | WO 2010/100135 A1 | 9/2010 | |
| WO | WO 2010/115995 A2 | 10/2010 | |
| WO | WO 2010/115998 A2 | 10/2010 | |
| WO | WO 2011/026945 A1 | 3/2011 | |
| WO | WO 2011/026948 A1 | 3/2011 | |
| WO | WO 2011/098518 A2 | 8/2011 | |
| WO | WO 2012/064627 A2 | 5/2012 | |
| WO | WO 2013/041722 A1 | 3/2013 | |
| WO | WO 2016/062766 A1 | 4/2016 | |

OTHER PUBLICATIONS

[No Author Listed], Compelling topline results from the Phase IIb combination therapy study of vobarilizumab, ALX-0061 (anti-IL-6R), in patients with moderate to severe RA. Presentation by Ablynx, Aug. 9, 2016.

[No Author Listed], Topline results from the Phase IIb monotherapy study of vobarilizumab. ALX-0061 (anti-IL-6R), in patients with moderate to severe RA. Presentation by Ablynx, Jul. 7, 2016.

Ali et al., Improvements in the cell-free production of functional antibodies using cell extract from protease-deficient *Escherichia coli* mutant. J Biosci Bioeng. Feb. 2005;99(2):181-6.

Atreya et al., Blockade of interleukin 6 trans signaling suppresses T-cell resistance against apoptosis in chronic intestinal inflammation: evidence in Crohn disease and experimental colitis in vivo. Nat Med. May 2000;6(5):583-8. Erratum in: Nat Med. Nov. 2010;16(11):1341.

Bataille et al., Biologic effects of anti-interleukin-6 murine monoclonal antibody in advanced multiple myeloma. Blood. Jul. 15, 1995;86(2):685-91.

Beck et al., Brief report: alleviation of systemic manifestations of Castleman's disease by monoclonal anti-interleukin-6 antibody. N Engl J Med. Mar. 3, 1994;330(9):602-5.

Becker et al., TGF-beta suppresses tumor progression in colon cancer by inhibition of IL-6 trans-signaling. Immunity. Oct. 2004;21(4):491-501.

Boulanger et al., Hexameric structure and assembly of the interleukin-6/IL-6 alpha-receptor/gp130 complex. Science. Jun. 27, 2003;300(5628):2101-4. Erratum in: Science. Aug. 15, 2003;301(5635):918.

Brorson et al., Mutational analysis of avidity and fine specificity of anti-levan antibodies. J Immunol. Dec. 15, 1999;163(12):6694-701.

Brummell et al., Probing the combining site of an anti-carbohydrate antibody by saturation-mutagenesis: role of the heavy-chain CDR3 residues. Biochemistry. Feb. 2, 1993;32(4):1180-7.

Campbell et al., Essential role for interferon-gamma and interleukin-6 in autoimmune insulin-dependent diabetes in NOD/Wehi mice. J Clin Invest. Feb. 1991;87(2):739-42.

Choy et al., Therapeutic benefit of blocking interleukin-6 activity with an anti-interleukin-6 receptor monoclonal antibody in rheumatoid arthritis: a randomized, double-blind, placebo-controlled, dose-escalation trial. Arthritis Rheum. Dec. 2002;46(12):3143-50.

Colman, Effects of amino acid sequence changes on antibody-antigen interactions. Res Immunol. Jan. 1994;145(1):33-6.

David et al., A study of the structural correlates of affinity maturation: antibody affinity as a function of chemical interactions, structural plasticity and stability. Mol Immunol. Feb. 2007;44(6):1342-51. Epub Jul. 18, 2006.

De Bruyn et al., Anti-IL-6 receptor Nanobody (ALX-0061) seamless first-in-human phase I/II POC study in patients with active RA on stable MTX treatment. Arthritis & Rheumatism. Oct. 1, 2012; 64(10) Suppl.: S561.

Decanniere et al., A single-domain antibody fragment in complex with RNase A: non-canonical loop structures and nanomolar affinity using two CDR loops. Structure. Apr. 15, 1999;7(4):361-70.

Desgeorges et al., Concentrations and origins of soluble interleukin 6 receptor-alpha in serum and synovial fluid. J Rheumatol. Aug. 1997;24(8):1510-6.

Desmyter et al., Antigen specificity and high affinity binding provided by one single loop of a camel single-domain antibody. J Biol Chem. Jul. 13, 2001;276(28):26285-90. Epub May 7, 2001.

Desmyter et al., Crystal structure of a camel single-domain VH antibody fragment in complex with lysozyme. Nat Struct Biol. Sep. 1996;3(9):803-11.

Doganci et al., The IL-6R alpha chain controls lung CD4+CD25+ Treg development and function during allergic airway inflammation in vivo. J Clin Invest. Feb. 2005;115(2):313-25. Erratum in: J Clin Invest. May 2005;115(5):1388. Lehr, Hans A [added].

Emilie et al., Cytokines in HIV infection. Int J Immunopharmacol. May-Jun. 1994;16(5-6):391-6.

Emilie et al., Administration of an anti-interleukin-6 monoclonal antibody to patients with acquired immunodeficiency syndrome and lymphoma: effect on lymphoma growth and on B clinical symptoms. Blood. Oct. 15, 1994;84(8):2472-9.

Frankel et al., Characterization of diphtheria fusion proteins targeted to the human interleukin-3 receptor. Protein Eng. Aug. 2000;13(8):575-81.

Frey et al., Population pharmacokinetic analysis of tocilizumab in patients with rheumatoid arthritis. J Clin Pharmacol. Jul. 2010;50(7):754-66. doi: 10.1177/0091270009350623. Epub Jan. 23, 2010.

Gaillard et al., Identification of a novel antigenic structure of the human receptor for interleukin-6 involved in the interaction with the glycoprotein 130 chain. Immunology. Sep. 1996;89(1):135-41.

Gratacos et al., Serum cytokines (IL-6, TNF-alpha, IL-1 beta and IFN-gamma) in ankylosing spondylitis: a close correlation between serum IL-6 and disease activity and severity. Br J Rheumatol. Oct. 1994;33(10):927-31.

Grau et al., Interleukin 6 production in experimental cerebral malaria: modulation by anticytokine antibodies and possible role in hypergammaglobulinemia. J Exp Med. Nov. 1, 1990;172(5):1505-8.

Grogg et al., HIV infection and lymphoma. J Clin Pathol. Dec. 2007;60(12):1365-72.

Hibi et al., Molecular cloning and expression of an IL-6 signal transducer, gp130. Cell. Dec. 21, 1990;63(6):1149-57.

Hinton et al., An engineered human IgG1 antibody with longer serum half-life. J Immunol. Jan. 1, 2006;176(1):346-56.

Hirano et al., Interleukin 6 and its receptor in the immune response and hematopoiesis. Int J Cell Cloning. Jan. 1990;8 Suppl 1:155-66; discussion 166-7.

Hirano et al., Biological and clinical aspects of interleukin 6. Immunol Today. Dec. 1990;11(12):443-9.

Hirano et al., Purification to homogeneity and characterization of human B-cell differentiation factor (BCDF or BSFp-2). Proc Natl Acad Sci U S A. Aug. 1985;82(16):5490-4.

(56) References Cited

OTHER PUBLICATIONS

Holliger et al., Engineered antibody fragments and the rise of single domains. Nat Biotechnol. Sep. 2005;23(9):1126-36.
Holt et al., Domain antibodies: proteins for therapy. Trends Biotechnol. Nov. 2003;21(11):484-90.
Holz et al., Twenty-four weeks of treatment with a novel anti-IL-6 receptor Nanobody (R) (ALX-0061) resulted in 84% ACR20 improvement and 58% DAS28 remission in a phase I/II study in RA. Annals of the Rheumatic Diseases. Jun. 2013; 72(suppl 3): 64. & Annual European Congress of Rheumatology (EULAR). Madrid, Spain. Jun. 12-15, 2013.
Holz et al.: Developing Nanobodies: from bench to bedside. Internet citation. Jun. 24, 2008. pp. 1-37. Retrieved from the internet http://www.pda.org/Presentation/2008/PDAEBEDublin/holzjosefin. asp.
Hosea et al., Prediction of human pharmacokinetics from preclinical information: comparative accuracy of quantitative prediction approaches. J Clin Pharmacol. May 2009;49(5):513-33. doi:10.1177/0091270009333209. Epub Mar. 19, 2009.
Houdebine, Production of pharmaceutical proteins by transgenic animals. Comp Immunol Microbiol Infect Dis. Mar. 2009;32(2):107-21. doi: 10.1016/j.cimid.2007.11.005. Epub Feb. 19, 2008.
Imazeki et al., IL-6 functions in cynomolgus monkeys blocked by a humanized antibody to human IL-6 receptor. Int J Immunopharmacol. Jul. 1998;20(7):345-57.
Ishihara et al., IL-6 in autoimmune disease and chronic inflammatory proliferative disease. Cytokine Growth Factor Rev. Aug.-Oct. 2002;13(4-5):357-68.
Ishihara et al., Molecular basis of the cell specificity of cytokine action. Biochim Biophys Acta. Nov. 11, 2002;1592(3):281-96.
Ito et al., A pilot randomized trial of a human anti-interleukin-6 receptor monoclonal antibody in active Crohn's disease. Gastroenterology. 2004;126:989-96.
Jang et al., Pharmacokinetic/pharmacodynamic (PK/PD) modeling and trial simulations to guide dose selection with CNTO 328, a chimeric anti-IL-6 monoclonal antibody (Mab), in patients with renal cell carcinoma (RCC). Journal of Clinical Oncology, 2004 ASCO Annual Meeting Proceedings (Post-Meeting Edition). 2004;22(14S, Jul. 15 Supplement):2608. Abstract.
Jilka et al., Increased osteoclast development after estrogen loss: mediation by interleukin-6. Science. Jul. 3, 1992;257(5066):88-91.
Jones et al., Replacing the complementarity-determining regions in a human antibody with those from a mouse. Nature. May 29-Jun. 4, 1986;321(6069):522-5.
Jones et al., Therapeutic strategies for the clinical blockade of IL 6/gp130 signaling. J Clin Invest. Sep. 2011;121(9):3375-83. doi: 10.1172/JCI57158. Epub Sep. 1, 2011.
Kalai et al., Participation of two Ser-Ser-Phe-Tyr repeats in interleukin-6 (IL-6)-binding sites of the human IL-6 receptor. Eur J Biochem. Jun. 15, 1996;238(3):714-23.
Kaufman et al., Transgenic analysis of a 100-kb human beta-globin cluster-containing DNA fragment propagated as a bacterial artificial chromosome. Blood. Nov. 1, 1999;94(9):3178-84. Erratum in: Blood Feb. 1, 2000;95(3):744.
Kipriyanov, Generation of bispecific and tandem diabodies. Methods Mol Biol. 2009;562:177-93.
Klein et al., Murine anti-interleukin-6 monoclonal antibody therapy for a patient with plasma cell leukemia. Blood. Sep. 1, 1991;78(5):1198-204.
Ko et al., Production of antibodies in plants: approaches and perspectives. Curr Top Microbiol Immunol. 2009;332:55-78. doi: 10.1007/978-3-540-70868-1_4.
Kobayashi et al., Tryptophan H33 plays an important role in pyrimidine (6-4) pyrimidone photoproduct binding by a high-affinity antibody. Protein Eng. Oct. 1999;12(10):879-84.
Lederman et al., A single amino acid substitution in a common African allele of the CD4 molecule ablates binding of the monoclonal antibody, OKT4. Mol Immunol. Nov. 1991;28(11):1171-81.
Levi et al., Effect of tocilizumab exposure on IL-6 and IL-6 receptor levels in patients with rheumatoid arthritis: graphical analysis of pooled data from four phase 3 clinical trials. Ann Rheum Dis. 2008;67(Suppl II):192. Abstract THU0176.
Levi et al., Effect of tocilizumab exposure on IL-6 and IL-6 receptor levels in patients with rheumatoid arthritis: graphical analysis of pooled data from four phase 3 clinical trials. Presentation EULAR conference. Jun. 11-14, 2008.
Levi et al., Reduction in inflammatory biomarkers with increasing exposure to the IL-6 inhibitor, tocilizumab, in patients with rheumatoid arthritis: Graphical analysis of pooled data. Ann Rheum Dis. 2008;67(Suppl II):192. Abstract THU0177.
Li et al., beta-Endorphin omission analogs: dissociation of immunoreactivity from other biological activities. Proc Natl Acad Sci U S A. Jun. 1980;77(6):3211-4.
Liautard et al., Epitope analysis of human IL-6 receptor gp80 molecule with monoclonal antibodies. Eur Cytokine Netw. May-Jun. 1994;5(3):293-300.
Lu et al., Acquired antagonistic activity of a bispecific diabody direct against two different epitopes on vascular endothelial growth factor receptor 2. J Immunol Methods. Nov. 19, 1999;230(1-2):159-71.
Martin, Protein Sequence and Structure Analysis of Antibody Variable Domains. In: Antibody Engineering Lab Manual (Ed.: Duebel, Kontermann, Springer-Verlag, Heidelberg). Chapter 3. 2010. 33-51.
Merk et al., Cell-free expression of two single-chain monoclonal antibodies against lysozyme: effect of domain arrangement on the expression. J Biochem. Feb. 1999;125(2):328-33.
Mihara et al., Humanized antibody to human interleukin-6 receptor inhibits the development of collagen arthritis in cynomolgus monkeys. Clin Immunol. Mar. 2001;98(3):319-26.
Murakami et al., The value of blocking IL-6 outside of rheumatoid arthritis: current perspective. Curr Opin Rheumatol. May 2011;23(3):273-7. doi: 10.1097/BOR.0b013e3283456797.
Muyldermans et al., Unique single-domain antigen binding fragments derived from naturally occurring camel heavy-chain antibodies. J Mol Recognit. Mar.-Apr. 1999;12(2):131-40.
Nakashima et al., Drug delivery options to increase patient adherence and satisfaction in the management of rheumatoid arthritis—focus on subcutaneous tocilizumab. Drug Des Devel Ther. Jul. 4, 2014;8:913-9. doi: 10.2147/DDDT.S52099. eCollection 2014.
Neurath et al., IL-6 signaling in autoimmunity, chronic inflammation and inflammation-associated cancer. Cytokine Growth Factor Rev. Apr. 2011;22(2):83-9. doi: 10.1016/j.cytogfr.2011.02.003. Epub Mar. 5, 2011.
Nishimoto et al., Humanized anti-interleukin-6 receptor antibody treatment of multicentric Castleman disease. Blood. Oct. 15, 2005;106(8):2627-32. Epub Jul. 5, 2005.
Nishimoto et al., Interleukin 6: from bench to bedside. Nat Clin Pract Rheumatol. Nov. 2006;2(11):619-26. Erratum in: Nat Clin Pract Rheumatol. Dec. 2006;2(12):691.
Nishimoto et al., Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease. Blood. Nov. 15, 2008;112(10):3959-64. doi: 10.1182/blood-2008-05-155846. Epub Sep. 10, 2008.
Nishimoto et al., Toxicity, pharmacokinetics, and dose-finding study of repetitive treatment with the humanized anti-interleukin 6 receptor antibody MRA in rheumatoid arthritis. Phase I/II clinical study. J Rheumatol. Jul. 2003;30(7):1426-35.
Nishimoto et al., Treatment of rheumatoid arthritis with humanized anti-interleukin-6 receptor antibody: a multicenter, double-blind, placebo-controlled trial. Arthritis Rheum. Jun. 2004;50(6):1761-9.
Nishimoto, Interleukin-6 as a therapeutic target in candidate inflammatory diseases. Clin Pharmacol Ther. Apr. 2010;87(4):483-7. doi: 10.1038/Clpt.2009.313. Epub Feb. 24, 2010.
Nowell et al., Soluble IL-6 receptor governs IL-6 activity in experimental arthritis: blockade of arthritis severity by soluble glycoprotein 130. J Immunol. Sep. 15, 2003;171(6):3202-9.
Ogata et al., Advances in interleukin-6 therapy. Jpn J Clin Pathol. Apr. 1999;47(4):321-6.
Paul, Fundamental immunology, 3rd Edition, 1993:292-295, under the heading Fv structure and diversity in three dimensions.

(56) References Cited

OTHER PUBLICATIONS

Prabhakar et al., Correlation of serum CNTO 328-Anti IL-6 monoclonal antibody (Mab) concentrations and biomarker expression in renal cell carcinoma (RCC) patients. Journal of Clinical Oncology, 2004 ASCO Annual Meeting Proceedings (Post-Meeting Edition). 2004;22(14S, Jul. 15 Supplement):2560. Abstract.

Rajpal et al., A general method for greatly improving the affinity of antibodies by using combinatorial libraries. Proc Natl Acad Sci U S A. Jun. 14, 2005;102(24):8466-71. Epub Jun. 6, 2005.

Revets et al., Nanobodies as novel agents for cancer therapy. Expert Opin Biol Ther. Jan. 2005;5(1):111-24.

Riechmann et al., Single domain antibodies: comparison of camel VH and camelised human VH domains. J Immunol Methods. Dec. 10, 1999;231(1-2):25-38.

Riechmann, Rearrangement of the former VL interface in the solution structure of a camelised, single antibody VH domain. J Mol Biol. Jun. 28, 1996;259(5):957-69.

Robert et al., Tumor targeting with newly designed biparatopic antibodies directed against two different epitopes of the carcinoembryonic antigen (CEA). Int J Cancer. Apr. 12, 1999;81(2):285-91.

Roitt et al., Immunology. 5th edition. 1998;80-81, 107. (translation of 110-111, 150 fromRussian-language version of ROITT et al., Immunology).

Roodman et al., Interleukin 6. A potential autocrine/paracrine factor in Paget's disease of bone. J Clin Invest. Jan. 1992;89(1):46-52.

Roodman et al., Interleukin-6: an osteotropic factor? J Bone Miner Res. May 1992;7(5):475-8.

Roovers et al., Efficient inhibition of EGFR signaling and of tumour growth by antagonistic anti-EFGR Nanobodies. Cancer Immunol Immunother. Mar. 2007;56(3):303-317.

Roovers et al., Nanobodies in therapeutic applications. Curr Opin Mol Ther. Aug. 2007;9(4):327-35.

Rose-John et al., Interleukin-6 biology is coordinated by membrane-bound and soluble receptors: role in inflammation and cancer. J Leukoc Biol. Aug. 2006;80(2):227-36. Epub May 17, 2006.

Rudikoff et al., Single amino acid substitution altering antigen-binding specificity. Proc Natl Acad Sci U S A. Mar. 1982;79(6):1979-83.

Saito et al., Preparation of monoclonal antibodies against the IL-6 signal transducer, gp130, that can inhibit IL-6-mediated functions. J Immunol Methods. Aug. 9, 1993;163(2):217-23.

Sato et al., Reshaping a human antibody to inhibit the interleukin 6-dependent tumor cell growth. Cancer Res. Feb. 15, 1993;53(4):851-6.

Scheller et al., Interleukin-6 and its receptor: from bench to bedside. Med Microbiol Immunol. Dec. 2006;195(4):173-83. Epub May 31, 2006.

Schmitt et al., Disease-drug-drug interaction involving tocilizumab and simvastatin in patients with rheumatoid arthritis. Clin Pharmacol Ther. May 2011;89(5):735-40. doi: 10.1038/clpt.2011.35. Epub Mar. 23, 2011. Erratum in: Clin Pharmacol Ther. Sep. 2011;90(3):479.

Schoels et al., Blocking the effects of interleukin-6 in rheumatoid arthritis and other inflammatory rheumatic diseases: systematic literature review and meta-analysis informing a consensus statement. Ann Rheum Dis. Apr. 2013;72(4):583-9. doi: 10.1136/annrheumdis-2012-202470. Epub Nov. 10, 2012.

Shinkura et al., In vivo blocking effects of a humanized antibody to human interleukin-6 receptor on interleukin-6 function in primates. Anticancer Res. Mar-Apr. 1998;18(2A):1217-21.

Smolen et al., Option Investigators. Effect of interleukin-6 receptor inhibition with tocilizumab in patients with rheumatoid arthritis (OPTION study): a double-blind, placebo-controlled, randomised trial. Lancet. Mar. 22, 2008;371(9617):987-97. doi: 10.1016/S0140-6736(08)60453-5.

Spinelli et al., The crystal structure of a llama heavy chain variable domain. Nat Struct Biol. Sep. 1996;3(9):752-7.

Starnes et al., Anti-IL-6 monoclonal antibodies protect against lethal *Escherichia coli* infection and lethal tumor necrosis factor-alpha challenge in mice [retraction of Starnes HF Jr, Pearce MK, Tewari A, Yim JH, Zou JC, Abrams JS. In: J Immunol Dec. 15, 1990;145(12):4185-91]. J Immunol. Mar. 15, 1995;148(6):1968.

Strassman et al., Evidence for the involvement of interleukin 6 in experimental cancer cachexia. J Clin Invest. May 1992;89:1681-1684.

Taga et al., Interleukin-6 triggers the association of its receptor with a possible signal transducer, gp130. Cell. Aug. 11, 1989;58(3):573-81.

Tanaka et al., Targeting interleukin-6: all the way to treat autoimmune and inflammatory diseases. Int J Biol Sci. 2012;8(9):1227-36. doi: 10.7150/ijbs.4666. Epub Oct. 24, 2012.

Tanaka et al., Therapeutic targeting of the interleukin-6 receptor. Annu Rev Pharmacol Toxicol. 2012;52:199-219. doi:10.1146/annurev-pharmtox-010611-134715. Epub Sep. 9, 2011.

Tijink et al., Improved tumor targeting of anti-epidermal growth factor receptor Nanobodies through albumin binding: taking advantage of modular Nanobody technology. Mol Cancer Ther. Aug. 2008;7(8):2288-97. doi: 10.1158/1535-7163.MCT-07-2384.

Trikha et al., Targeted anti-interleukin-6 monoclonal antibody therapy for cancer: a review of the rationale and clinical evidence. Clin Cancer Res. Oct. 15, 2003;9(13):4653-65.

Uson et al., Soluble interleukin 6 (IL-6) receptor and IL-6 levels in serum and synovial fluid of patients with different arthropathies. J Rheumatol. Nov. 1997;24(11):2069-75.

Van Roy et al., ALX-0061, an anti-IL-6R Nanobody® for therapeutic use in rheumatoid arthritis, demonstrates in vitro a different biological activity profile as compared to tocilizumab. [Online] (Jan. 2014) ResearchGate. Retrieved on Jul. 18, 2019 Retrieved from: https://www.researchgate.net/profile /Maarten_Van_Roy/publication /275562632_FRI0021_ALX-0061_an_anti-IL-r_nanobodyR_for_therapeutic_use_in_rheumatoid_arthritis_demonstrates_in_vitro_a_differential_biological_activity_profile_as_compared_to_tocilizumab/links/572ca03d08ae9e 18450dgd3f/FRI0021_Alx-0061-an-anti-IL-6r-nanobodyR-for-therapeutic-use-in-rheumatoid-arthritis-demonstrates-in-vitro-a-differential-biological-activity-profile-as-compared-to-tocilizumab.pdf?origin=publiation_detail>. 5 pages. p. 1 is full poster. pp. 2-5 are magnifications of each quadrant.

Van Roy et al., The preclinical pharmacology of the high affinity anti-IL-6R Nanobody® ALX-0061 supports its clinical development in rheumatoid arthritis. Arthritis Res Ther. May 20, 2015;17:135. doi: 10.1186/s13075-015-0651-0.

Vierboom et al., Preclinical evaluation of anti-rheumatic drugs in a non-human primate model of arthritic disease. Drug Discovery Today: Disease Models. 2008; 30(20):e1-7. doi.10.1016/j.ddmod.2008.06.003.

Wang et al., Rapid analysis of gene expression (RAGE) facilitates universal expression profiling. Nucleic Acids Res. Dec. 1, 1999;27(23):4609-18.

Wendling et al., Treatment of severe rheumatoid arthritis by anti-interleukin 6 monoclonal antibody. J Rheumatol. Feb. 1993;20(2):259-62.

Wesolowski et al., Single domain antibodies: promising experimental and therapeutic tools in infection and immunity. Med Miccrobiol Immunol. Aug. 2009;198(3):157-74. doi: 10.1007/s00430-009-0116-7. Epub Jun. 16, 2009.

Woo et al., Open label phase II trial of single, ascending doses of MRA in Caucasian children with severe systemic juvenile idiopathic arthritis: proof of principle of the efficacy of IL-6 receptor blockade in this type of arthritis and demonstration of prolonged clinical improvement. Arthritis Res Ther. 2005;7(6):R1281-8. Epub Sep. 15, 2005.

Yamasaki et al., Cloning and expression of the human interleukin-6 (BSF-2/IFN beta 2) receptor. Science. Aug. 12, 1988;241(4867):825-8.

Yau et al., Affinity maturation of a V(H)H by mutational hotspot randomization, J Immunol Methods. Feb. 2005;297(1-2):213-24. Epub Jan. 20, 2005.

Yokota et al., Phase 2 trials of anti-IL6 receptor antibody (MRA) for systemic onset juvenile idiopathic arthritis. Autoimmune Rev. 2004;3:599-600.

(56) References Cited

OTHER PUBLICATIONS

Zaki et al., CNTO 328, a monoclonal antibody to IL-6, inhibits human tumor-induced cachexia in nude mice. Int J Cancer. Sep. 10, 2004;111(4):592-5.
Zhang et al., Clinical pharmacology of tocilizumab for the treatment of patients with rheumatoid arthritis. Expert Rev Clin Pharmacol. Sep. 2011;4(5):539-58. doi: 10.1586/ecp.11.33.
Richter et al., Mechanistic determinants of biotherapeutics absorption following SC administration. AAPS J. Sep. 2012;14(3):559-70. doi: 10.1208/s12248-012-9367-0. Epub May 23, 2012.
Richter et al., Subcutaneous absorption of biotherapeutics: knowns and unknowns. Drug Metab Dispos. Nov. 2014;42(11):1881-9. doi: 10.1124/dmd.114.059238. Epub Aug. 6, 2014.
Zheng et al., Minipig as a potential translatable model for monoclonal antibody pharmacokinetics after intravenous and subcutaneous administration. MAbs. Mar.-Apr. 2012;4(2):243-55. doi: 10.4161/mabs.4.2.19387. Epub Mar. 1, 2012.
PCT/EP2015/074364, May 4, 2017, International Prelminary Report on Patentability.

\* cited by examiner

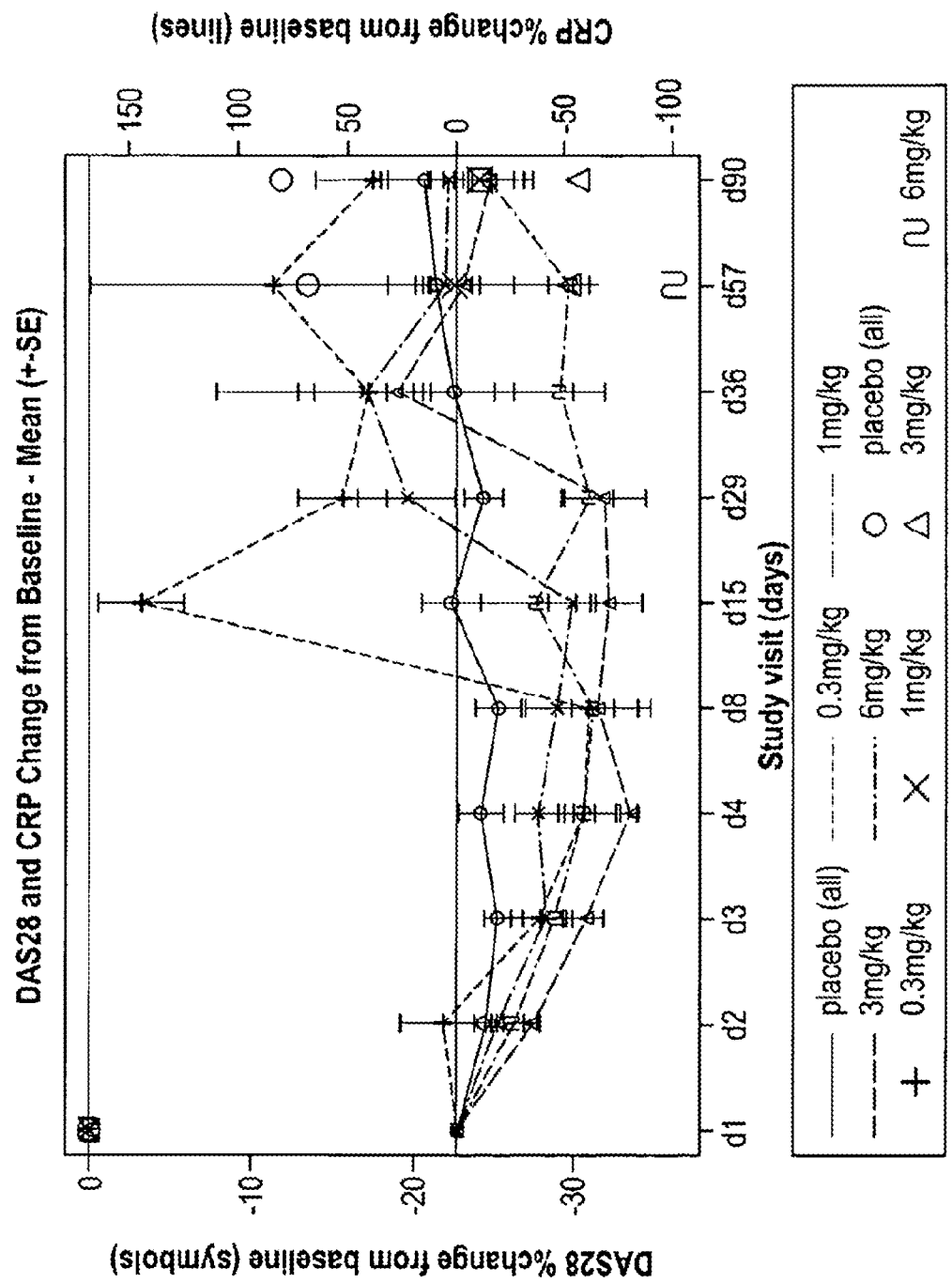

SEQUENCE LISTING

<160> NUMBER OF SEQ ID NOS: 55

<210> SEQ ID NO 1
<211> LENGTH: 121
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Tyr Trp Gly
                100                 105                 110

Gln Gly Thr Leu Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Thr Thr Phe Arg Ile Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
                100                 105                 110

Gln Gly Thr Leu Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Arg Val Asn
            20                  25                  30

Val Met Ala Trp Tyr Arg Gln Ala Pro Gly Lys Gly Arg Glu Leu Val
        35                  40                  45

Ala Ala Val Ile Asn Gly Gly Thr Thr Tyr Ala Asp Ser Val Lys
    50                  55                  60

Gly Arg Phe Thr Ile Ser Arg Asp Asn Ala Lys Asn Thr Leu Tyr Leu
 65                  70                  75                  80
```

```
Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Ile Met Ala Trp Tyr Arg Gln Ala Pro Gly Lys Gly Arg Glu Leu Val
        35                  40                  45

Ala Gly Val Ile Thr Gly Gly Asn Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg Ile Asn
            20                  25                  30

Val Met Ala Trp Tyr Arg Gln Ala Pro Gly Lys Gly Arg Glu Leu Val
        35                  40                  45

Ala Gly Val Ile Asn Asp Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120
```

```
<210> SEQ ID NO 6
<211> LENGTH: 121
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Val Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Asn Ser Asp Tyr Asp Leu Gly Arg Arg Tyr Trp Gly
            100                 105                 110

Gln Gly Thr Leu Val Thr Val Ser Ser
        115                 120

<210> SEQ ID NO 7
<211> LENGTH: 121
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Val Asn
            20                  25                  30

Val Met Ala Trp Tyr Arg Gln Ala Pro Gly Lys Gly Arg Glu Leu Val
        35                  40                  45

Ala Gly Ile Ile Asn Gly Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 8
<211> LENGTH: 121
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
            35                  40                  45

Ala Gly Ile Val Ser Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser
            115                 120

<210> SEQ ID NO 9
<211> LENGTH: 121
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Ile Asn
            20                  25                  30

Val Met Ala Trp Tyr Arg Gln Ala Pro Gly Lys Gly Arg Glu Leu Val
            35                  40                  45

Ala Gly Ile Val Thr Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser
            115                 120

<210> SEQ ID NO 10
<211> LENGTH: 121
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
            35                  40                  45

Ala Gly Ile Val Thr Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
```

```
                65                  70                  75                  80
Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser
        115                 120

<210> SEQ ID NO 11
<211> LENGTH: 30
<212> TYPE: PRT
<213> ORGANISM: Artificial Sequence
<220> FEATURE:
<223> OTHER INFORMATION: Framework sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Framework sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Framework sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Framework sequence

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg
            20                  25                  30

<210> SEQ ID NO 15
<211> LENGTH: 30
<212> TYPE: PRT
```

```
<213> ORGANISM: Artificial Sequence
<220> FEATURE:
<223> OTHER INFORMATION: Framework sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Framework sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys
            20                  25                  30

<210> SEQ ID NO 17
<211> LENGTH: 5
<212> TYPE: PRT
<213> ORGANISM: Artificial Sequence
<220> FEATURE:
<223> OTHER INFORMATION: CDR sequence

<400> SEQUENCE: 17

Ile Asn Val Met Ala
1               5

<210> SEQ ID NO 18
<211> LENGTH: 5
<212> TYPE: PRT
<213> ORGANISM: Artificial Sequence
<220> FEATURE:
<223> OTHER INFORMATION: CDR sequence

<400> SEQUENCE: 18

Val Asn Val Met Ala
1               5

<210> SEQ ID NO 19
<211> LENGTH: 5
<212> TYPE: PRT
<213> ORGANISM: Artificial Sequence
<220> FEATURE:
<223> OTHER INFORMATION: CDR sequence

<400> SEQUENCE: 19

Ile Asn Ile Met Ala
1               5

<210> SEQ ID NO 20
<211> LENGTH: 14
<212> TYPE: PRT
<213> ORGANISM: Artificial Sequence
<220> FEATURE:
<223> OTHER INFORMATION: Framework sequence

<400> SEQUENCE: 20

Trp Tyr Arg Gln Ala Pro Gly Lys Gly Arg Glu Leu Val Ala
1               5                   10
```

```
<210> SEQ ID NO 21
<211> LENGTH: 16
<212> TYPE: PRT
<213> ORGANISM: Artificial Sequence
<220> FEATURE:
<223> OTHER INFORMATION: CDR sequence

<400> SEQUENCE: 21

Gly Ile Ile Ser Gly Gly Ser Thr Ser Tyr Ala Asp Ser Val Lys Gly
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: CDR sequence

<400> SEQUENCE: 22

Gly Ile Ile Thr Asn Gly Ser Thr Ser Tyr Ala Asp Ser Val Lys Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: CDR sequence

<400> SEQUENCE: 23

Ala Val Ile Asn Gly Gly Thr Thr Thr Tyr Ala Asp Ser Val Lys Gly
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: CDR sequence

<400> SEQUENCE: 24

Gly Val Ile Thr Gly Gly Asn Thr Thr Tyr Ala Asp Ser Val Lys Gly
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: CDR sequence

<400> SEQUENCE: 25

Gly Val Ile Asn Asp Gly Ser Thr Thr Tyr Ala Asp Ser Val Lys Gly
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: CDR sequence

<400> SEQUENCE: 26

Gly Ile Val Ser Gly Gly Ser Thr Ser Tyr Ala Asp Ser Val Lys Gly
1               5                   10                  15
```

```
<210> SEQ ID NO 27
<211> LENGTH: 16
<212> TYPE: PRT
<213> ORGANISM: Artificial Sequence
<220> FEATURE:
<223> OTHER INFORMATION: CDR sequence

<400> SEQUENCE: 27

Gly Ile Ile Asn Gly Gly Ser Thr Thr Tyr Ala Asp Ser Val Lys Gly
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: CDR sequence

<400> SEQUENCE: 28

Gly Ile Val Thr Gly Gly Ser Thr Ser Tyr Ala Asp Ser Val Lys Gly
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Framework sequence

<400> SEQUENCE: 29

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Phe
            20                  25                  30

<210> SEQ ID NO 30
<211> LENGTH: 13
<212> TYPE: PRT
<213> ORGANISM: Artificial Sequence
<220> FEATURE:
<223> OTHER INFORMATION: CDR sequence

<400> SEQUENCE: 30

Ile Thr Thr Glu Ser Asp Tyr Asp Leu Gly Arg Arg Tyr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: CDR sequence

<400> SEQUENCE: 31

Ile Thr Thr Asn Ser Asp Tyr Asp Leu Gly Arg Arg Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: CDR sequence

<400> SEQUENCE: 32

Val Thr Thr Asn Ser Asp Tyr Asp Leu Gly Arg Asp Tyr
```

<210> SEQ ID NO 33
<211> LENGTH: 11
<212> TYPE: PRT
<213> ORGANISM: Artificial Sequence
<220> FEATURE:
<223> OTHER INFORMATION: Framework sequence

<400> SEQUENCE: 33

Trp Gly Gln Gly Thr Leu Val Thr Val Ser Ser
1               5                   10

<210> SEQ ID NO 34
<211> LENGTH: 245
<212> TYPE: PRT
<213> ORGANISM: Artificial Sequence
<220> FEATURE:
<223> OTHER INFORMATION: Nanobody sequence

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser
                245

<210> SEQ ID NO 35
<211> LENGTH: 375
<212> TYPE: PRT
<213> ORGANISM: Artificial Sequence
<220> FEATURE:

<223> OTHER INFORMATION: Nanobody sequence

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
            85                  90                  95

Phe Ile Thr Thr Glu Ser Asp Tyr Asp Leu Gly Arg Arg Tyr Trp Gly
        100                 105                 110

Gln Gly Thr Leu Val Thr Val Ser Ser Gly Gly Gly Ser Gly Gly
    115                 120                 125

Gly Ser Glu Val Gln Leu Val Glu Ser Gly Gly Gly Leu Val Gln Pro
130                 135                 140

Gly Gly Ser Leu Arg Leu Ser Cys Ala Ala Ser Gly Ser Val Phe Lys
145                 150                 155                 160

Ile Asn Val Met Ala Trp Tyr Arg Gln Ala Pro Gly Lys Gly Arg Glu
                165                 170                 175

Leu Val Ala Gly Ile Ile Ser Gly Gly Ser Thr Ser Tyr Ala Asp Ser
            180                 185                 190

Val Lys Gly Arg Phe Thr Ile Ser Arg Asp Asn Ala Lys Asn Thr Leu
        195                 200                 205

Tyr Leu Gln Met Asn Ser Leu Arg Pro Glu Asp Thr Ala Val Tyr Tyr
    210                 215                 220

Cys Ala Phe Ile Thr Thr Glu Ser Asp Tyr Asp Leu Gly Arg Arg Tyr
225                 230                 235                 240

Trp Gly Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Asn Ser Leu Arg Leu Ser Cys Ala Ala Ser Gly Phe Thr
        275                 280                 285

Phe Ser Ser Phe Gly Met Ser Trp Val Arg Gln Ala Pro Gly Lys Gly
    290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
        355                 360                 365

Thr Leu Val Thr Val Ser Ser
    370                 375
```

<210> SEQ ID NO 36
<211> LENGTH: 375

```
<212> TYPE: PRT
<213> ORGANISM: Artificial Sequence
<220> FEATURE:
<223> OTHER INFORMATION: Nanobody sequence

<400> SEQUENCE: 36

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Arg Leu Ser Cys Ala Ala Ser Gly Ser Val Phe Lys Ile Asn Val Met
        275                 280                 285

Ala Trp Tyr Arg Gln Ala Pro Gly Lys Gly Arg Glu Leu Val Ala Gly
    290                 295                 300

Ile Ile Ser Gly Gly Ser Thr Ser Tyr Ala Asp Ser Val Lys Gly Arg
305                 310                 315                 320

Phe Thr Ile Ser Arg Asp Asn Ala Lys Asn Thr Leu Tyr Leu Gln Met
                325                 330                 335

Asn Ser Leu Arg Pro Glu Asp Thr Ala Val Tyr Tyr Cys Ala Phe Ile
            340                 345                 350

Thr Thr Glu Ser Asp Tyr Asp Leu Gly Arg Arg Tyr Trp Gly Gln Gly
        355                 360                 365

Thr Leu Val Thr Val Ser Ser
    370                 375
```

<210> SEQ ID NO 37
<211> LENGTH: 115
<212> TYPE: PRT
<213> ORGANISM: Artificial Sequence
<220> FEATURE:
<223> OTHER INFORMATION: Nanobody sequence

<400> SEQUENCE: 37

```
Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115
```

<210> SEQ ID NO 38
<211> LENGTH: 115
<212> TYPE: PRT
<213> ORGANISM: Artificial Sequence
<220> FEATURE:
<223> OTHER INFORMATION: Nanobody sequence

<400> SEQUENCE: 38

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 39
<211> LENGTH: 117
<212> TYPE: PRT
<213> ORGANISM: Artificial Sequence
<220> FEATURE:
<223> OTHER INFORMATION: Nanobody sequence

<400> SEQUENCE: 39

Ala Val Gln Leu Val Glu Ser Gly Gly Gly Leu Val Gln Gly Gly Gly

```
                1               5                  10                  15
Ser Leu Arg Leu Ala Cys Ala Ala Ser Glu Arg Ile Phe Asp Leu Asn
                    20                  25                  30

Leu Met Gly Trp Tyr Arg Gln Gly Pro Gly Asn Glu Arg Glu Leu Val
                    35                  40                  45

Ala Thr Cys Ile Thr Val Gly Asp Ser Thr Asn Tyr Ala Asp Ser Val
        50                  55                  60

Lys Gly Arg Phe Thr Ile Ser Met Asp Tyr Lys Gln Thr Val Tyr
65                  70                  75                  80

Leu His Met Asn Ser Leu Arg Pro Glu Asp Thr Gly Leu Tyr Tyr Cys
                    85                  90                  95

Lys Ile Arg Arg Thr Trp His Ser Glu Leu Trp Gly Gln Gly Thr Gln
                    100                 105                 110

Val Thr Val Ser Ser
            115

<210> SEQ ID NO 40
<211> LENGTH: 5
<212> TYPE: PRT
<213> ORGANISM: Artificial Sequence
<220> FEATURE:
<223> OTHER INFORMATION: Linker sequence

<400> SEQUENCE: 40

Gly Gly Gly Gly Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Linker sequence

<400> SEQUENCE: 41

Ser Gly Gly Ser Gly Gly Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Linker sequence

<400> SEQUENCE: 42

Gly Gly Gly Gly Ser Gly Gly Gly Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Linker sequence

<400> SEQUENCE: 43

Gly Gly Gly Gly Ser Gly Gly Gly Ser
1               5

<210> SEQ ID NO 44
<211> LENGTH: 10
<212> TYPE: PRT
```

```
<213> ORGANISM: Artificial Sequence
<220> FEATURE:
<223> OTHER INFORMATION: Linker sequence

<400> SEQUENCE: 44

Gly Gly Gly Gly Ser Gly Gly Gly Ser
1               5

<210> SEQ ID NO 45
<211> LENGTH: 15
<212> TYPE: PRT
<213> ORGANISM: Artificial Sequence
<220> FEATURE:
<223> OTHER INFORMATION: Linker sequence

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 18
<212> TYPE: PRT
<213> ORGANISM: Artificial Sequence
<220> FEATURE:
<223> OTHER INFORMATION: Linker sequence

<400> SEQUENCE: 46

Gly Gly Gly Gly Ser Gly Gly Gly Gly Ser Gly Gly Gly Gly Gly
1               5                   10                  15

Gly Ser

<210> SEQ ID NO 47
<211> LENGTH: 20
<212> TYPE: PRT
<213> ORGANISM: Artificial Sequence
<220> FEATURE:
<223> OTHER INFORMATION: Linker sequence

<400> SEQUENCE: 47

Gly Gly Gly Gly Ser Gly Gly Gly Gly Ser Gly Gly Gly Gly Ser Gly
1               5                   10                  15

Gly Gly Gly Ser
            20

<210> SEQ ID NO 48
<211> LENGTH: 25
<212> TYPE: PRT
<213> ORGANISM: Artificial Sequence
<220> FEATURE:
<223> OTHER INFORMATION: Linker sequence

<400> SEQUENCE: 48

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 49
<211> LENGTH: 30
<212> TYPE: PRT
<213> ORGANISM: Artificial Sequence
<220> FEATURE:
<223> OTHER INFORMATION: Linker sequence

<400> SEQUENCE: 49
```

```
Gly Gly Gly Gly Ser Gly Gly Gly Gly Ser Gly Gly Gly Ser Gly
1               5                   10                  15
Gly Gly Gly Ser Gly Gly Gly Ser Gly Gly Gly Ser
            20                  25              30
```

<210> SEQ ID NO 50
<211> LENGTH: 35
<212> TYPE: PRT
<213> ORGANISM: Artificial Sequence
<220> FEATURE:
<223> OTHER INFORMATION: Linker sequence

<400> SEQUENCE: 50

```
Gly Gly Gly Gly Ser Gly Gly Gly Gly Ser Gly Gly Gly Ser Gly
1               5                   10                  15
Gly Gly Gly Ser Gly Gly Gly Ser Gly Gly Gly Ser Gly Gly
            20                  25                  30
Gly Gly Ser
        35
```

<210> SEQ ID NO 51
<211> LENGTH: 15
<212> TYPE: PRT
<213> ORGANISM: Artificial Sequence
<220> FEATURE:
<223> OTHER INFORMATION: Linker sequence

<400> SEQUENCE: 51

```
Glu Pro Lys Ser Cys Asp Lys Thr His Thr Cys Pro Pro Cys Pro
1               5                   10                  15
```

<210> SEQ ID NO 52
<211> LENGTH: 24
<212> TYPE: PRT
<213> ORGANISM: Artificial Sequence
<220> FEATURE:
<223> OTHER INFORMATION: Linker sequence

<400> SEQUENCE: 52

```
Gly Gly Gly Gly Ser Gly Gly Gly Ser Glu Pro Lys Ser Cys Asp Lys
1               5                   10                  15
Thr His Thr Cys Pro Pro Cys Pro
            20
```

<210> SEQ ID NO 53
<211> LENGTH: 12
<212> TYPE: PRT
<213> ORGANISM: Artificial Sequence
<220> FEATURE:
<223> OTHER INFORMATION: Linker sequence

<400> SEQUENCE: 53

```
Glu Pro Lys Thr Pro Lys Pro Gln Pro Ala Ala Ala
1               5                   10
```

<210> SEQ ID NO 54
<211> LENGTH: 62
<212> TYPE: PRT
<213> ORGANISM: Artificial Sequence
<220> FEATURE:
<223> OTHER INFORMATION: Linker sequence

<400> SEQUENCE: 54

```
Glu Leu Lys Thr Pro Leu Gly Asp Thr Thr His Thr Cys Pro Arg Cys
1               5                   10                  15
```

```
Pro Glu Pro Lys Ser Cys Asp Thr Pro Pro Cys Pro Arg Cys Pro
            20                  25              30

Glu Pro Lys Ser Cys Asp Thr Pro Pro Cys Pro Arg Cys Pro Glu
        35                  40              45

Pro Lys Ser Cys Asp Thr Pro Pro Pro Cys Pro Arg Cys Pro
    50                  55              60

<210> SEQ ID NO 55
<211> LENGTH: 3
<212> TYPE: PRT
<213> ORGANISM: Artificial Sequence
<220> FEATURE:
<223> OTHER INFORMATION: Linker sequence

<400> SEQUENCE: 55

Ala Ala Ala
1
```

METHOD FOR TREATING RHEUMATOID ARTHRITIS BY ADMINISTERING IL-6 RECEPTOR ANTIBODIES

RELATED APPLICATIONS

This application is a divisional of U.S. application Ser. No. 14/345,702, filed Mar. 19, 2014, which is a national stage filing under 35 U.S.C. § 371 of international application PCT/EP2012/068765, filed Sep. 24, 2012, which was published under PCT Article 21(2) in English, and claims the benefit under 35 U.S.C. § 119(e) of U.S. provisional application Ser. No. 61/538,500, filed Sep. 23, 2011, U.S. provisional application Ser. No. 61/604,774, filed Feb. 29, 2012, and U.S. provisional application Ser. No. 61/664,337, filed Jun. 26, 2012, the disclosures of which are incorporated by reference herein in their entireties.

FIELD OF THE INVENTION

The present invention relates to methods for inhibiting IL-6 mediated signaling for prolonged periods of time. More specifically, the present invention provides polypeptides directed against IL-6R at specific dose ranges for inhibiting IL-6 mediated signaling for prolonged periods of time.

BACKGROUND OF THE INVENTION

Interleukin-6 (IL-6), originally identified as a B cell differentiation factor (Hirano et al. 1985, Proc. Natl. Acad. Sci. USA, 82: 5490-4; EP 0257406), is a multifunction cytokine that has a wide range of biological activities in various target cells and regulates—amongst others—immune responses, acute phase reactions, hematopoiesis, bone metabolism, angiogenesis, and inflammation (Nishimoto et al. 2006, Nat. Clin. Pract. Rheumatol. 2: 619-626). The interaction of IL-6 with IL-6 receptor (IL-6R) (Yamasaki et al. 1988, Science 241: 825-8; EP 0325474), an 80-kDa ligand-binding chain (IL-6R α-chain, or CD126), results in the formation of the IL-6/IL-6R complex. This complex binds to the membrane protein gp130 (Taga et al. 1989, Cell 58: 573-81; EP 0411946), a 130-kDa non-ligand-binding signal-transducing chain (IL-6R β-chain, or CD130) on a target cell, which transmits various physiological actions of IL-6. In cells with sufficient membrane-bound IL-6R, IL-6 binds to these receptors, the IL-6/IL-6R complex induces homodimerization of the gp130 molecule, and a high-affinity functional receptor complex of IL-6, IL-6R, and gp130 is formed (Hibi et al. 1990, Cell 63: 1149-1157). In cells that do not express sufficient cell-surface IL-6R, IL-6 signal transduction starts with the binding of IL-6 to the free, soluble form of IL-6R (sIL-6R), which lacks the membrane and intracytoplasmic portion of the 80-kDa membrane-bound IL-6R molecule (Taga et al. 1989, Cell 58: 573-581; Hibi et al. 1990, Cell 63: 1149-1157). Thus, either membrane-bound or soluble IL-6R can mediate IL-6 signal into cells, as long as the cells express gp130. Considerable amounts of sIL-6R are observed in serum and body fluids (Usón et al. 1997, J. Rheumatol. 24: 2069-2075; Desgeorges et al. 1997, 24: 1510-1516), and sIL-6R may play physiologic roles as well as having a pathologic role in immune-inflammatory and malignant diseases (Rose-John et al. 2006, J. Leukocyte Biol. 80: 227-236). Processes mediated via sIL-6R are indicated as trans-signaling.

Deregulation of IL-6 production is implicated in the pathology of several autoimmune and chronic inflammatory proliferative disease processes (Ishihara and Hirano 2002, Biochim. Biophys. Acta 1592: 281-96). IL-6 overproduction and signaling (and in particular trans-signaling) are involved in various diseases and disorders, such as sepsis (Starnes et al. 1999, J. Immunol. 148: 1968) and various forms of cancer such as multiple myeloma disease (MM), renal cell carcinoma (RCC), plasma cell leukaemia (Klein et al. 1991, Blood 78: 1198-204), lymphoma, B-lymphoproliferative disorder (BLPD) and prostate cancer. Non-limiting examples of other diseases caused by excessive IL-6 production or signaling include bone resorption (osteoporosis) (Roodman et al. 1992, J. Bone Miner. Res. 7: 475-8; Jilka et al. 1992, Science 257: 88-91), cachexia (Strassman et al. 1992, J. Clin. Invest. 89: 1681-1684), psoriasis, mesangial proliferative glomerulonephritis, Kaposi's sarcoma, AIDS-related lymphoma (Emilie et al. 1994, Int. J. Immunopharmacol. 16: 391-6), inflammatory diseases and disorder such as rheumatoid arthritis (RA), systemic onset juvenile idiopathic arthritis (JIA), hypergammaglobulinemia (Grau et al. 1990, J. Exp. Med. 172: 1505-8); Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al. 1991, J. Clin. Invest. 87: 739-742).

As a consequence, inhibitors of IL-6 induced signaling have attracted much attention in the past (Hirano et al. 1990, Immunol. Today 11: 443-9). Polypeptides specifically binding to IL-6 (Klein et al. 1991, Blood 78: 1198-204; EP 0312996), IL-6R (EP 0409607) or gp130 (Saito et al. 1993, J. Immunol. Methods 163: 217-223; EP 0572118) proved to exhibit an efficient inhibitory effect on IL-6 functioning. Different antibodies and antibody fragments directed against human IL-6, against human IL-6R and against human gp130 protein for the prevention and treatment of IL-6 related disorders have been described. Examples are tocilizumab (Woo et al. 2005, Arthritis Res. Ther. 7: 1281-8; Nishimoto et al. 2005, Blood 106: 2627-32; Ito et al. 2004, Gastroenterology 126: 989-96; Choy et al. 2002, Arthritis Rheum. 46: 3143-50), BE8 (Bataille et al. 1995, Blood 86: 685-91; Emilie et al. 1994, Blood 84: 2472-9; Beck et al. 1994, N. Engl. J. Med. 330: 602-5; Wendling et al. 1993, J. Rheumatol. 20: 259-62) and CNTO-328 of Centocor (2004, Journal of Clinical Oncology 22/14S: 2560; 2004, Journal of Clinical Oncology 22/14S: 2608; 2004, Int. J. Cancer 111: 592-5). Another active principle known in the art for the prevention and treatment of IL-6 related disorders is an Fc fusion of soluble gp130 (Becker et al. 2004, Immunity 21: 491-501; Doganci et al. 2005, J. Clin. Invest. 115: 313-25; Nowell et al. 2003, J. Immunol. 171: 3202-9; Atreya et al. 2000, Nat. Med. 6: 583-8). Immunoglobulin single variable domains directed against IL-6R and polypeptides comprising the same have been described in WO 08/020079. Improved immunoglobulin single variable domains directed against IL-6R, have been described in WO 2010/115998 (see e.g. SEQ ID NOs: 60-72 of WO 2010/115998).

Tocilizumab is a humanized anti-human IL-6R antibody engineered by grafting the complementarily determining regions of a mouse anti-human IL-6R antibody into human IgG1κ to create a human antibody with a human IL-6R binding site (Sato et al. 1993, Cancer Res. 53: 851-856). Tocilizumab binds to the IL-6 binding site of human IL-6R and competitively inhibits IL-6 signaling. A series of clinical studies have shown that inhibition of IL-6 signaling by tocilizumab is therapeutically effective in RA, JIA, Castleman disease, and Crohn's disease (Nishimoto et al. 2003, J. Rheumatol. 30: 1426-1435; Nishimoto et al. 2004, Arthritis Rheum. 50: 1761-1769; Yokota et al. 2004, Autoimmun.

Rev. 3: 599-600; Nishimote et al. 2005, Blood 106: 2627-2632; Ito et al. 2004, Gastroenterology 126: 989-996). In all of these diseases, tocilizumab ameliorated inflammatory manifestations and normalized acute phase protein levels, including C-reactive protein (CRP). Studies have confirmed 8 mg/kg every 4 weeks as the optimal dose and 4 mg/kg as the starting dose for the treatment of RA, with favorable efficacy and acceptable safety profiles. Tocilizumab 8 mg/kg every 4 weeks produced a sustained, adequate blockade of IL-6 receptors and normalized acute-phase reactants, such as C-reactive protein.

It was noticed that both serum IL-6 and serum sIL-6R increased in patients when IL-6 signaling was inhibited by tocilizumab while the disease symptoms continued to be ameliorated. Data showed that IL-6 temporarily increased following administration of tocilizumab. The increase was most likely caused by IL-6R blockade inhibiting clearance of IL-6 from the blood. Subsequently, there was a trend for decreasing IL-6 peak levels during 24 weeks for tocilizumab 8 mg/kg, suggesting decreased IL-6 production with amelioration of the disease or inflammatory status.

Following multiple doses of tocilizumab 4 or 8 mg/kg every 4 weeks for 24 weeks, mean sIL-6R levels increased with increasing treatment duration and reached a plateau at approximately weeks 8-12. For the 4 mg/kg dose, sIL-6R levels increased slightly with treatment duration. Peak sIL-6R levels were achieved in the middle of the dosing interval (i.e., at weeks 2, 6 and 14). The highest mean sIL-6R levels for tocilizumab 4 mg/kg were 5.1-5.6-fold above baseline. For the 8 mg/kg dose, mean sIL-6R levels remained high and increased with treatment duration, with minor fluctuations within the dosing interval. The highest mean sIL-6R levels for tocilizumab 8 mg/kg were 10-14-fold above baseline. The sustained increase in sIL-6R levels observed for the 8 mg/kg dose suggests persistent binding of tocilizumab to sIL-6R. At the 4 mg/kg dose, the fluctuating levels of sIL-6R suggest that tocilizumab exposure was below that for consistent binding of tocilizumab to sIL-6R. The accumulation of the sIL-6R in serum with an increasing number of tocilizumab infusions suggests that the tocilizumab/sIL-6R complex has a slower clearance than sIL-6R (Levi et al. 2008, Ann. Rheum. Dis. 67 (Suppl. II): 192).

Mean CRP normalized by week 2 of treatment with tocilizumab 8 mg/kg every 4 weeks and remained below the upper limit of normal through to week 24. By contrast, the improvement with tocilizumab 4 mg/kg was less striking and CRP concentrations fluctuated during the dosing interval (Smolen et al. 2008, Lancet 371: 987-997). Higher tocilizumab AUC (area under the curve for serum tocilizumab concentration-time profile from week 0-24) was associated with a more persistent low CRP level with a normal range from pooled pivotal Phase III studies (Levi et al. 2008, Ann. Rheum. Dis. 67 (Suppl. II): 192). Tocilizumab normalized the CRP levels in patients with RA as long as free tocilizumab remained ≥µg/ml (Nishimoto et al. 2008, Blood 112: 3959-3964).

It was shown that, after tocilizumab administration, more than 95% of the sIL-6R molecules were bound as immune complex, as long as the free tocilizumab concentration remained ≥µg/ml (Nishimoto et al. 2008, Blood 112: 3959-3964). The relationship of tocilizumab, sIL-6R and CRP following single-dose tocilizumab administration (10 mg/kg) in RA patients is further illustrated in FIG. 1 (Schmitt et al. 2010, Clin. Pharmacol. Ther. 89: 735-740). (Zhan and Peck, 2011, Expert Rev. Clin. Pharmacol. 4: 539-558)

SUMMARY OF THE INVENTION

The present invention is based on the finding that the administration to human subjects of polypeptides as described herein that specifically bind IL-6R (also referred herein as "polypeptides of the invention") provides an unexpectedly sustained, prolonged effect on IL-6 mediated signaling in the human subjects as observed through changes in relevant biomarkers (such as sIL-6R, IL-6, CRP, ESR, fibrinogen and/or serum amyloid A). This sustained, prolonged effect on IL-6 mediated signaling is mainly caused by a slower target mediated clearance of the polypeptide of the invention compared to the target mediated clearance of tocilizumab, of which the value was used in preclinical modeling. Because of this slower target mediated clearance of the polypeptide of the invention an unexpectedly sustained, prolonged effect on IL-6 mediated signaling in the human subjects was observed compared to what was assessed based on pre-clinical modeling. As a consequence, less therapeutic molecules (i.e. lower doses) need to be administered, or less frequent dosing of the therapeutic molecule needs to be applied in order to obtained the same effect on IL-6 mediated signaling (observed through changes in relevant biomarkers such as sIL-6R, IL-6, CRP, ESR, fibrinogen and serum amyloid A). Alternatively, a longer effect on IL-6 mediated signaling can be obtained with a similar dose of the polypeptide of the invention.

Accordingly, the present invention provides methods for inhibiting IL-6 mediated signaling in a subject by administering to the subject a polypeptide of the invention, wherein the amount of the polypeptide administered is effective to change one or more markers of IL-6 mediated signaling, such as total sIL-6R, total IL-6, CRP, ESR, fibrinogen and/or serum amyloid A, for unexpectedly prolonged periods of time. The present invention provides specific dose ranges and dosing schedules for the polypeptides of the invention that result in this prolonged effect on IL-6 mediated signaling. In particular, the invention provides pharmacologically active agents, compositions, methods and/or dosing schedules that have certain advantages compared to the agents, compositions, methods and/or dosing schedules that are currently used and/or known in the art, including the ability to dose less frequently or to administer lower doses to obtain equivalent effects in inhibiting IL-6 mediated signaling. These advantages will become clear from the further description below.

Accordingly, in one aspect, the invention relates to a method for inhibiting IL-6 mediated signaling in a subject, said method comprising administering to the subject a polypeptide that specifically binds IL-6R (also referred to herein as "polypeptide of the invention"), wherein the amount of the polypeptide administered is effective to increase total sIL-6R levels in serum to at least 400 ng/ml and to maintain total sIL-6R levels in serum at at least 400 ng/ml for at least 4 weeks after administration. The invention thus also relates to a polypeptide of the invention for inhibiting IL-6 mediated signaling, wherein the amount of the polypeptide administered is effective to increase total sIL-6R levels in serum to at least 400 ng/ml and to maintain total sIL-6R levels in serum at at least 400 ng/ml for at least 4 weeks after administration. The invention also relates to a polypeptide of the invention for treatment of diseases and/or disorders associated with IL-6 mediated signaling, wherein the amount of the polypeptide administered is effective to increase total sIL-6R levels in serum to at least 400 ng/ml and to maintain total sIL-6R levels in serum at at least 400 ng/ml for at least 4 weeks after administration.

In another aspect, the invention relates to a method for inhibiting IL-6 mediated signaling in a subject comprising administering to the subject a polypeptide of the invention, wherein the amount of the polypeptide administered is effective to increase total IL-6 levels in serum to at least 40 pg/ml and to maintain total IL-6 levels in serum at at least 40 pg/ml for at least 4 weeks after administration. The invention thus also relates to a polypeptide of the invention for inhibiting IL-6 mediated signaling, wherein the amount of the polypeptide administered is effective to increase total IL-6 levels in serum to at least 40 pg/ml and to maintain total IL-6 levels in serum at at least 40 pg/ml for at least 4 weeks after administration. The invention also relates to a polypeptide of the invention for treatment of diseases and/or disorders associated with IL-6 mediated signaling, wherein the amount of the polypeptide administered is effective to increase total IL-6 levels in serum to at least 40 pg/ml and to maintain total IL-6 levels in serum at at least 40 pg/ml for at least 4 weeks after administration.

In a further aspect, the invention relates to a method for inhibiting IL-6 mediated signaling in a subject comprising administering to the subject a polypeptide of the invention, wherein the amount of the polypeptide administered is effective to reduce CRP levels in serum below 10 mg/l and to maintain CRP levels in serum below 10 mg/l for at least 4 weeks after administration. The invention thus also relates to a polypeptide of the invention for inhibiting IL-6 mediated signaling, wherein the amount of the polypeptide administered is effective to reduce CRP levels in serum below 10 mg/l and to maintain CRP levels in serum below 10 mg/l for at least 4 weeks after administration. The invention also relates to a polypeptide of the invention for treatment of diseases and/or disorders associated with IL-6 mediated signaling, wherein the amount of the polypeptide administered is effective to reduce CRP levels in serum below 10 mg/l and to maintain CRP levels in serum below 10 mg/l for at least 4 weeks after administration.

In a specific aspect, when the subject is also receiving methotrexate (MTX) therapy, the baseline CRP levels (i.e. the CRP levels before dosing the polypeptide of the invention) in serum are most likely already below 10 mg/ml (unrelated to the anti-IL-6R therapy). Accordingly, "reduction of CRP levels in serum below 10 mg/l and maintenance of CRP levels in serum below 10 mg/l" cannot be used as a relevant marker for the pharmacodynamic effect of the polypeptide of the invention in subjects that also receive MTX therapy, but only in subjects that do not receive methotrexate (MTX) therapy.

Therefore, in certain cases (such as when the subject is also receiving MTX therapy), changes in CRP levels can also be determined as "% reduction compared to baseline (i.e. CRP levels before treatment with the polypeptide of the invention (pre-treatment) and/or at normal levels)". In a further aspect, the invention relates to a method for inhibiting IL-6 mediated signaling in a subject comprising administering to the subject a polypeptide of the invention, wherein the amount of the polypeptide administered is effective to reduce CRP levels in serum by 50% or more compared to baseline (i.e. pre-treatment or normal) levels and to maintain CRP levels in serum at 50% or more reduction compared to baseline levels for at least 4 weeks after administration. The invention thus also relates to a polypeptide of the invention for inhibiting IL-6 mediated signaling, wherein the amount of the polypeptide administered is effective to reduce CRP levels in serum by 50% or more compared to baseline (i.e. pre-treatment or normal) levels and to maintain CRP levels in serum at 50% or more reduction compared to baseline levels for at least 4 weeks after administration. The invention also relates to a polypeptide of the invention for treatment of diseases and/or disorders associated with IL-6 mediated signaling, wherein the amount of the polypeptide administered is effective to reduce CRP levels in serum by 50% or more compared to baseline (i.e. pre-treatment or normal) levels and to maintain CRP levels in serum at 50% or more reduction compared to baseline levels for at least 4 weeks after administration.

In a further aspect, the invention relates to a method for inhibiting IL-6 mediated signaling in a subject comprising administering to the subject a polypeptide of the invention, wherein the amount of the polypeptide administered is effective to reduce ESR levels in serum by 30% or more compared to baseline (i.e. pre-treatment or normal) levels and to maintain ESR levels in serum at 30% or more reduction compared to baseline levels for at least 4 weeks after administration. The invention thus also relates to a polypeptide of the invention for inhibiting IL-6 mediated signaling, wherein the amount of the polypeptide administered is effective to reduce ESR levels in serum by 30% or more compared to baseline (i.e. pre-treatment or normal) levels and to maintain ESR levels in serum at 30% or more reduction compared to baseline levels for at least 4 weeks after administration. The invention also relates to a polypeptide of the invention for treatment of diseases and/or disorders associated with IL-6 mediated signaling, wherein the amount of the polypeptide administered is effective to reduce ESR levels in serum by 30% or more compared to baseline (i.e. pre-treatment or normal) levels and to maintain ESR levels in serum at 30% or more reduction compared to baseline levels for at least 4 weeks after administration.

In a further aspect, the invention relates to a method for inhibiting IL-6 mediated signaling in a subject comprising administering to the subject a polypeptide of the invention, wherein the amount of the polypeptide administered is effective to reduce fibrinogen levels in serum by 30% or more compared to baseline (i.e. pre-treatment or normal) levels and to maintain fibrinogen levels in serum at 30% or more reduction compared to baseline levels for at least 4 weeks after administration. The invention thus also relates to a polypeptide of the invention for inhibiting IL-6 mediated signaling, wherein the amount of the polypeptide administered is effective to reduce fibrinogen levels in serum by 30% or more compared to baseline (i.e. pre-treatment or normal) levels and to maintain fibrinogen levels in serum at 30% or more reduction compared to baseline levels for at least 4 weeks after administration. The invention also relates to a polypeptide of the invention for treatment of diseases and/or disorders associated with IL-6 mediated signaling, wherein the amount of the polypeptide administered is effective to reduce fibrinogen levels in serum by 30% or more compared to baseline (i.e. pre-treatment or normal) levels and to maintain fibrinogen levels in serum at 30% or more reduction compared to baseline levels for at least 4 weeks after administration.

In a further aspect, the invention relates to a method for inhibiting IL-6 mediated signaling in a subject comprising administering to the subject a polypeptide of the invention, wherein the amount of the polypeptide administered is effective to reduce serum amyloid A levels by 30% or more compared to baseline (i.e. pre-treatment or normal) levels and to maintain serum amyloid A levels at 30% or more reduction compared to baseline levels for at least 4 weeks after administration. The invention thus also relates to a polypeptide of the invention for inhibiting IL-6 mediated signaling, wherein the amount of the polypeptide administered is effective to reduce serum amyloid A levels by 30% or more compared to baseline (i.e. pre-treatment or normal) levels and to maintain serum amyloid A levels at 30% or more reduction compared to baseline levels for at least 4 weeks after administration. The invention also relates to a polypeptide of the invention for treatment of diseases and/or disorders associated with IL-6 mediated signaling, wherein the amount of the polypeptide administered is effective to reduce serum amyloid A levels by 30% or more compared to baseline (i.e. pre-treatment or normal) levels and to maintain serum amyloid A levels at 30% or more reduction compared to baseline levels for at least 4 weeks after administration.

Preferably, total sIL-6R levels in serum are increased to at least 400 ng/ml within two weeks after the start of the therapy (i.e. within two weeks after administration of the polypeptide of the invention).

Preferably, total IL-6 levels in serum are increased to at least 40 pg/ml within two weeks after the start of the therapy (i.e. within two weeks after administration of the polypeptide of the invention).

Preferably, CRP levels in serum are reduced below 10 mg/l within two weeks after the start of the therapy (i.e. within two weeks after administration of the polypeptide of the invention).

Preferably, CRP levels in serum are reduced by 50% or more compared to baseline (i.e. pre-treatment or normal) levels within two weeks after the start of the therapy (i.e. within two weeks after administration of the polypeptide of the invention).

Preferably, ESR levels in serum are reduced by 30% or more compared to baseline (i.e. pre-treatment or normal) levels within two weeks after the start of the therapy (i.e. within two weeks after administration of the polypeptide of the invention).

Preferably, fibrinogen levels in serum are reduced by 30% or more compared to baseline (i.e. pre-treatment or normal) levels within two weeks after the start of the therapy (i.e. within two weeks after administration of the polypeptide of the invention).

Preferably, serum amyloid A levels are reduced by 30% or more compared to baseline (i.e. pre-treatment or normal) levels within two weeks after the start of the therapy (i.e. within two weeks after administration of the polypeptide of the invention).

In the method of the present invention, the polypeptide is administered in an amount from about 1 mg/kg to about 10 mg/kg, preferably from about 3 mg/kg to about 6 mg/kg. Accordingly, in a specific aspect, the invention relates to a method for inhibiting IL-6 mediated signaling in a subject, said method comprising administering to the subject a polypeptide of the invention in an amount from about 1 mg/kg to about 10 mg/kg, preferably from about 3 mg/kg to about 6 mg/kg, wherein total sIL-6R levels in serum are increased to and maintained at at least 400 ng/ml for at least 4 weeks after administration. The invention thus also relates to a polypeptide of the invention for inhibiting IL-6 mediated signaling, wherein the polypeptide is administered in an amount from about 1 mg/kg to about 10 mg/kg, preferably from about 3 mg/kg to about 6 mg/kg and wherein total sIL-6R levels in serum are increased to and maintained at at least 400 ng/ml for at least 4 weeks after administration. The invention also relates to a polypeptide of the invention for treatment of diseases and/or disorders associated with IL-6 mediated signaling, wherein the polypeptide is administered in an amount from about 1 mg/kg to about 10 mg/kg, preferably from about 3 mg/kg to about 6 mg/kg and wherein total sIL-6R levels in serum are increased to and maintained at at least 400 ng/ml for at least 4 weeks after administration.

In the method of the invention, the polypeptide of the invention is administered in an amount from about 1 mg/kg to about 10 mg/kg, preferably from about 3 mg/kg to about 6 mg/kg and total sIL-6R levels in serum are maintained at at least 400 ng/ml for up to 4 weeks or more, such as at least 5 weeks after administration, preferably at least 6 weeks, or at least 7 weeks after administration, and most preferably at least 8 weeks after administration.

In the method of the invention, the polypeptide of the invention is administered in an amount from about 1 mg/kg to about 10 mg/kg, preferably from about 3 mg/kg to about 6 mg/kg and total sIL-6R levels in serum are increased to and maintained at at least 400 ng/ml or more, such as at least 500 ng/ml, preferably at least 600 ng/ml, at least 650 ng/ml, or even at least 700 ng/ml or more, for up to 4 weeks or more.

In another aspect, the invention relates to a method for inhibiting IL-6 mediated signaling in a subject, said method comprising administering to the subject a polypeptide of the invention in an amount from about 1 mg/kg to about 10 mg/kg, preferably from about 3 mg/kg to about 6 mg/kg, wherein total IL-6 levels in serum are increased to and maintained at at least 40 pg/ml for at least 4 weeks after administration. The invention thus also relates to a polypeptide of the invention for inhibiting IL-6 mediated signaling, wherein the polypeptide is administered in an amount from about 1 mg/kg to about 10 mg/kg, preferably from about 3 mg/kg to about 6 mg/kg and wherein total IL-6 levels in serum are increased to and maintained at at least 40 pg/ml for at least 4 weeks after administration. The invention also relates to a polypeptide of the invention for treatment of diseases and/or disorders associated with IL-6 mediated signaling, wherein the polypeptide is administered in an amount from about 1 mg/kg to about 10 mg/kg, preferably from about 3 mg/kg to about 6 mg/kg and wherein total IL-6 levels in serum are increased to and maintained at at least 40 pg/ml for at least 4 weeks after administration.

In the method of the invention, the polypeptide of the invention is administered in an amount from about 1 mg/kg to about 10 mg/kg, preferably from about 3 mg/kg to about 6 mg/kg and total IL-6 levels in serum are maintained at at least 40 pg/ml for up to 4 weeks or more, such as at least 5 weeks after administration, preferably at least 6 weeks, or at least 7 weeks after administration, and most preferably at least 8 weeks after administration.

In the method of the invention, the polypeptide of the invention is administered in an amount from about 1 mg/kg to about 10 mg/kg, preferably from about 3 mg/kg to about 6 mg/kg and total IL-6 levels in serum are increased to and maintained at at least 40 pg/ml or more, such as at least 50 pg/ml, preferably at least 60 pg/ml or more, for up to 4 weeks or more.

In a further aspect, the invention relates to a method for inhibiting IL-6 mediated signaling in a subject, said method comprising administering to the subject a polypeptide of the invention in an amount from about 1 mg/kg to about 10 mg/kg, preferably from about 3 mg/kg to about 6 mg/kg, wherein CRP levels in serum are decreased to and maintained below 10 mg/l for at least 4 weeks after administration. The invention thus also relates to a polypeptide of the invention for inhibiting of IL-6 mediated signaling, wherein the polypeptide is administered in an amount from about 1 mg/kg to about 10 mg/kg, preferably from about 3 mg/kg to about 6 mg/kg and wherein CRP levels in serum are decreased to and maintained below 10 mg/l for at least 4 weeks after administration. The invention also relates to a polypeptide of the invention for treatment of diseases and/or disorders associated with IL-6 mediated signaling, wherein the polypeptide is administered in an amount from about 1 mg/kg to about 10 mg/kg, preferably from about 3 mg/kg to about 6 mg/kg and wherein CRP levels in serum are decreased to and maintained below 10 mg/l for at least 4 weeks after administration.

In the method of the invention, the polypeptide of the invention is administered in an amount from about 1 mg/kg to about 10 mg/kg, preferably from about 3 mg/kg to about 6 mg/kg and CRP levels in serum are maintained below 10 mg/l for up to 4 weeks or more, such as at least 5 weeks after administration, preferably at least 6 weeks, or at least 7 weeks after administration, and most preferably at least 8 weeks after administration.

In the method of the invention, the polypeptide of the invention is administered in an amount amount from about 1 mg/kg to about 10 mg/kg, preferably from about 3 mg/kg to about 6 mg/kg and CRP levels in serum are decreased to and maintained below 10 mg/l or less, such as below 9 mg/l, below 8 mg/l, more preferably below 7.5 mg/l, below 7 mg/l, below 6.5 mg/l, most preferably below 6 mg/l, below 5.5 mg/l or below 5 mg/l or lower, for up to 4 weeks or more.

In a specific aspect, when the subject is also receiving methotrexate (MTX) therapy, the baseline CRP levels (i.e. the CRP levels before dosing the polypeptide of the invention) in serum are most likely already below 10 mg/ml (unrelated to the anti-IL-6R therapy). Accordingly, "reduction of CRP levels in serum below 10 mg/l and maintenance of CRP levels in serum below 10 mg/l" cannot be used as a relevant marker for the pharmacodynamic effect of the polypeptide of the invention in subjects that also receive MTX therapy, but only in subjects that do not receive methotrexate (MTX) therapy.

In a further aspect, the invention relates to a method for inhibiting IL-6 mediated signaling in a subject, said method comprising administering to the subject a polypeptide of the invention in an amount from about 1 mg/kg to about 10 mg/kg, preferably from about 3 mg/kg to about 6 mg/kg, wherein CRP levels in serum are decreased by and maintained at 50% or more (reduction) compared to baseline (i.e. pre-treatment or normal) levels for at least 4 weeks after administration. The invention thus also relates to a polypeptide of the invention for inhibiting of IL-6 mediated signaling, wherein the polypeptide is administered in an amount from about 1 mg/kg to about 10 mg/kg, preferably from about 3 mg/kg to about 6 mg/kg and wherein CRP levels in serum are decreased by and maintained at 50% or more (reduction) compared to baseline (i.e. pre-treatment or normal) levels for at least 4 weeks after administration. The invention also relates to a polypeptide of the invention for treatment of diseases and/or disorders associated with IL-6 mediated signaling, wherein the polypeptide is administered in an amount from about 1 mg/kg to about 10 mg/kg, preferably from about 3 mg/kg to about 6 mg/kg and wherein CRP levels in serum are decreased by and maintained at 50% or more (reduction) compared to baseline (i.e. pre-treatment or normal) levels for at least 4 weeks after administration.

In the method of the invention, the polypeptide of the invention is administered in an amount from about 1 mg/kg to about 10 mg/kg, preferably from about 3 mg/kg to about 6 mg/kg and CRP levels in serum are maintained at 50% or more reduction compared to baseline (i.e. pre-treatment or normal) levels for up to 4 weeks or more, such as at least 5 weeks after administration, preferably at least 6 weeks, or at least 7 weeks after administration, and most preferably at least 8 weeks after administration.

In the method of the invention, the polypeptide of the invention is administered in an amount from about 1 mg/kg to about 10 mg/kg, preferably from about 3 mg/kg to about 6 mg/kg and CRP levels in serum are decreased by and maintained at 50% or more (reduction) compared to baseline (i.e. pre-treatment or normal) levels, at 30% or more, 40% or more, 50% or more, 60% or more, or even 70% or more reduction compared to baseline (i.e. pre-treatment or normal) levels, for up to 4 weeks or more.

In a further aspect, the invention relates to a method for inhibiting IL-6 mediated signaling in a subject, said method comprising administering to the subject a polypeptide of the invention in an amount from about 1 mg/kg to about 10 mg/kg, preferably from about 3 mg/kg to about 6 mg/kg, wherein ESR levels in serum are decreased by and maintained at 30% or more (reduction) compared to baseline (i.e. pre-treatment or normal) levels for at least 4 weeks after administration. The invention thus also relates to a polypeptide of the invention for inhibiting of IL-6 mediated signaling, wherein the polypeptide is administered in an amount from about 1 mg/kg to about 10 mg/kg, preferably from about 3 mg/kg to about 6 mg/kg and wherein ESR levels in serum are decreased by and maintained at 30% or more (reduction) compared to baseline (i.e. pre-treatment or normal) levels for at least 4 weeks after administration. The invention also relates to a polypeptide of the invention for treatment of diseases and/or disorders associated with IL-6 mediated signaling, wherein the polypeptide is administered in an amount from about 1 mg/kg to about 10 mg/kg, preferably from about 3 mg/kg to about 6 mg/kg and wherein ESR levels in serum are decreased by and maintained at 30% or more (reduction) compared to baseline (i.e. pre-treatment or normal) levels for at least 4 weeks after administration.

In the method of the invention, the polypeptide of the invention is administered in an amount from about 1 mg/kg to about 10 mg/kg, preferably from about 3 mg/kg to about 6 mg/kg and ESR levels in serum are maintained at 30% or more reduction compared to baseline (i.e. pre-treatment or normal) levels for up to 4 weeks or more, such as at least 5 weeks after administration, preferably at least 6 weeks, or at least 7 weeks after administration, and most preferably at least 8 weeks after administration.

In the method of the invention, the polypeptide of the invention is administered in an amount from about 1 mg/kg to about 10 mg/kg, preferably from about 3 mg/kg to about 6 mg/kg and ESR levels in serum are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels, for up to 4 weeks or more.

In a further aspect, the invention relates to a method for inhibiting IL-6 mediated signaling in a subject, said method comprising administering to the subject a polypeptide of the invention in an amount from about 1 mg/kg to about 10 mg/kg, preferably from about 3 mg/kg to about 6 mg/kg, wherein fibrinogen levels in serum are decreased by and maintained at 30% or more (reduction) compared to baseline (i.e. pre-treatment or normal) levels for at least 4 weeks after administration. The invention thus also relates to a polypeptide of the invention for inhibiting of IL-6 mediated signaling, wherein the polypeptide is administered in an amount from about 1 mg/kg to about 10 mg/kg, preferably from about 3 mg/kg to about 6 mg/kg and wherein fibrinogen levels in serum are decreased by and maintained at 30% or more (reduction) compared to baseline (i.e. pre-treatment or normal) levels for at least 4 weeks after administration. The invention also relates to a polypeptide of the invention for treatment of diseases and/or disorders associated with IL-6 mediated signaling, wherein the polypeptide is administered in an amount from about 1 mg/kg to about 10 mg/kg, preferably from about 3 mg/kg to about 6 mg/kg and wherein fibrinogen levels in serum are decreased by and maintained at 30% or more (reduction) compared to baseline (i.e. pre-treatment or normal) levels for at least 4 weeks after administration.

In the method of the invention, the polypeptide of the invention is administered in an amount from about 1 mg/kg to about 10 mg/kg, preferably from about 3 mg/kg to about 6 mg/kg and fibrinogen levels in serum are maintained at 30% or more reduction compared to baseline (i.e. pre-treatment or normal) levels for up to 4 weeks or more, such as at least 5 weeks after administration, preferably at least 6 weeks, or at least 7 weeks after administration, and most preferably at least 8 weeks after administration.

In the method of the invention, the polypeptide of the invention is administered in an amount from about 1 mg/kg to about 10 mg/kg, preferably from about 3 mg/kg to about 6 mg/kg and fibrinogen levels in serum are decreased by and maintained at 30% or more (reduction) compared to baseline (i.e. pre-treatment or normal) levels, at 20% or more, 30% or more, 40% or more, or even 50% or more reduction compared to baseline (i.e. pre-treatment or normal) levels, for up to 4 weeks or more.

In a further aspect, the invention relates to a method for inhibiting IL-6 mediated signaling in a subject, said method comprising administering to the subject a polypeptide of the invention in an amount from about 1 mg/kg to about 10 mg/kg, preferably from about 3 mg/kg to about 6 mg/kg, wherein serum amyloid A levels are decreased by and maintained at 30% or more (reduction) compared to baseline (i.e. pre-treatment or normal) levels for at least 4 weeks after administration. The invention thus also relates to a polypeptide of the invention for inhibiting of IL-6 mediated signaling, wherein the polypeptide is administered in an amount from about 1 mg/kg to about 10 mg/kg, preferably from about 3 mg/kg to about 6 mg/kg and wherein serum amyloid A levels are decreased by and maintained at 30% or more (reduction) compared to baseline (i.e. pre-treatment or normal) levels for at least 4 weeks after administration. The invention also relates to a polypeptide of the invention for treatment of diseases and/or disorders associated with IL-6 mediated signaling, wherein the polypeptide is administered in an amount from about 1 mg/kg to about 10 mg/kg, preferably from about 3 mg/kg to about 6 mg/kg and wherein serum amyloid A levels are decreased by and maintained at 30% or more (reduction) compared to baseline (i.e. pre-treatment or normal) levels for at least 4 weeks after administration.

In the method of the invention, the polypeptide of the invention is administered in an amount from about 1 mg/kg to about 10 mg/kg, preferably from about 3 mg/kg to about 6 mg/kg and serum amyloid A levels are maintained at 30% or more reduction compared to baseline (i.e. pre-treatment or normal) levels for up to 4 weeks or more, such as at least 5 weeks after administration, preferably at least 6 weeks, or at least 7 weeks after administration, and most preferably at least 8 weeks after administration.

In the method of the invention, the polypeptide of the invention is administered in an amount from about 1 mg/kg to about 10 mg/kg, preferably from about 3 mg/kg to about 6 mg/kg and serum amyloid A levels are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels, for up to 4 weeks or more.

In one aspect, the polypeptide of the invention is administered as a single dose. In another aspect, the polypeptide of the invention is administered as a multiple dose. Preferred frequencies of administering the polypeptide of the invention include 4 to 8 weekly dosing, such as 4 weekly or 8 weekly dosing. Preferred dosage schedules include about 3 mg/kg every 4 weeks, about 6 mg/kg every 4 weeks, and about 6 mg/kg every 8 weeks.

The invention thus relates to a method for inhibiting IL-6 mediated signaling in a subject, said method comprising administering to the subject a polypeptide of the invention in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein total sIL-6R levels in serum are increased to and maintained (throughout the treatment period) at at least 400 ng/ml. The invention thus also relates to a polypeptide of the invention for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein total sIL-6R levels in serum are increased to and maintained (throughout the treatment period) at at least 400 ng/ml. The invention also relates to a polypeptide of the invention for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein total sIL-6R levels in serum are increased to and maintained (throughout the treatment period) at at least 400 ng/ml.

In the method of the invention, the polypeptide of the invention is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and total sIL-6R levels in serum are increased to and maintained at at least 400 ng/ml or more, such as at least 500 ng/ml, preferably at least 600 ng/ml, at least 650 ng/ml, or even at least 700 ng/ml or more.

In another aspect, the invention relates to a method for inhibiting IL-6 mediated signaling in a subject, said method comprising administering to the subject a polypeptide of the invention in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein total IL-6 levels in serum are increased to and maintained at at least 40 pg/ml. The invention thus also relates to a polypeptide of the invention for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein total IL-6 levels in serum are increased to and maintained at at least 40 pg/ml. The invention also relates to a polypeptide of the invention for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks)

and wherein total IL-6 levels in serum are increased to and maintained at least 40 pg/ml.

In the method of the invention, the polypeptide of the invention is administered in an amount from about 3 mg/kg to about 6 mg/kg every 4 to 8 weeks (such as 3 mg/kg every 4 weeks, 6 mg/kg every 4 weeks, or 6 mg/kg every 8 weeks) and total IL-6 levels in serum are increased to and maintained at least 40 pg/ml or more, such as at least 50 pg/ml, preferably at least 60 pg/ml or more.

In a further aspect, the invention relates to a method for inhibiting IL-6 mediated signaling in a subject, said method comprising administering to the subject a polypeptide of the invention in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein CRP levels in serum are decreased to and maintained below 10 mg/l. The invention thus also relates to a polypeptide of the invention for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased to and maintained below 10 mg/l. The invention also relates to a polypeptide of the invention for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased to and maintained below 10 mg/l.

In the method of the invention, the polypeptide of the invention is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and CRP levels in serum are decreased to and maintained below 10 mg/l or less, such as below 9 mg/l, below 8 mg/l, more preferably below 7.5 mg/l, below 7 mg/l, below 6.5 mg/l, most preferably below 6 mg/l, below 5.5 mg/l or below 5 mg/l or lower.

In a specific aspect, when the subject is also receiving methotrexate (MTX) therapy, the baseline CRP levels (i.e. the CRP levels before dosing the polypeptide of the invention) in serum are most likely already below 10 mg/ml or less (unrelated to the anti-IL-6R therapy). Accordingly, "reduction of CRP levels in serum below 10 mg/l or less and maintenance of CRP levels in serum below 10 mg/l or less" cannot be used as a relevant marker for the pharmacodynamic effect of the polypeptide of the invention in subjects that also receive MTX therapy, but only in subjects that do not receive methotrexate (MTX) therapy.

In a further aspect, the invention relates to a method for inhibiting IL-6 mediated signaling in a subject, said method comprising administering to the subject a polypeptide of the invention in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein CRP levels in serum are decreased by and maintained at 50% or more (reduction) compared to baseline (i.e. pre-treatment or normal) levels. The invention thus also relates to a polypeptide of the invention for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased by and maintained at 50% or more (reduction) compared to baseline (i.e. pre-treatment or normal) levels. The invention also relates to a polypeptide of the invention for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased by and maintained at 50% or more (reduction) compared to baseline (i.e. pre-treatment or normal) levels.

In the method of the invention, the polypeptide of the invention is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and CRP levels in serum are decreased by and maintained at 50% or more (reduction) compared to baseline (i.e. pre-treatment or normal) levels, at 30% or more, 40% or more, 50% or more, 60% or more, or even 70% or more reduction compared to baseline (i.e. pre-treatment or normal) levels.

In a further aspect, the invention relates to a method for inhibiting IL-6 mediated signaling in a subject, said method comprising administering to the subject a polypeptide of the invention in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein ESR levels in serum are decreased by and maintained at 30% or more (reduction) compared to baseline (i.e. pre-treatment or normal) levels. The invention thus also relates to a polypeptide of the invention for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein ESR levels in serum are decreased by and maintained at 30% or more (reduction) compared to baseline (i.e. pre-treatment or normal) levels. The invention also relates to a polypeptide of the invention for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein ESR levels in serum are decreased by and maintained at 30% or more (reduction) compared to baseline (i.e. pre-treatment or normal) levels.

In the method of the invention, the polypeptide of the invention is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and ESR levels in serum are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels.

In a further aspect, the invention relates to a method for inhibiting IL-6 mediated signaling in a subject, said method comprising administering to the subject a polypeptide of the invention in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein fibrinogen levels in serum are decreased by and maintained at 30% or more (reduction) compared to baseline (i.e. pre-treatment or normal) levels. The invention thus also relates to a polypeptide of the invention for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein fibrinogen levels in serum are decreased by and maintained at 30% or more (reduction) compared to baseline (i.e. pre-treatment or normal) levels. The invention also relates to a polypeptide of the invention for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein fibrinogen levels in serum are decreased by and maintained at 30% or more (reduction) compared to baseline (i.e. pre-treatment or normal) levels.

In the method of the invention, the polypeptide of the invention is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and fibrinogen levels in serum are decreased by and maintained at 30% or more (reduction) compared to baseline (i.e. pre-treatment or normal) levels, at 20% or more, 30% or more, 40% or more, or even 50% or more reduction compared to baseline (i.e. pre-treatment or normal) levels.

In a further aspect, the invention relates to a method for inhibiting IL-6 mediated signaling in a subject, said method comprising administering to the subject a polypeptide of the invention in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein serum amyloid A levels are decreased by and maintained at 30% or more (reduction) compared to baseline (i.e. pre-treatment or normal) levels. The invention thus also relates to a polypeptide of the invention for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein serum amyloid A levels are decreased by and maintained at 30% or more (reduction) compared to baseline (i.e. pre-treatment or normal) levels. The invention also relates to a polypeptide of the invention for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein serum amyloid A levels are decreased by and maintained at 30% or more (reduction) compared to baseline (i.e. pre-treatment or normal) levels.

In the method of the invention, the polypeptide of the invention is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and serum amyloid A levels are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels.

The method of the present invention can be used for prevention and/or treatment of subjects that suffer from IL-6 mediated diseases and/or disorders, or diseases and/or disorders in which IL-6 mediated processes could play a role, i.e. diseases and/or disorders related to IL-6 mediated signaling, such as but not limited to sepsis, various forms of cancer (such as multiple myeloma disease (MM), renal cell carcinoma (RCC), plasma cell leukaemia, lymphoma, B-lymphoproliferative disorder (BLPD) and prostate cancer), bone resorption (osteoporosis), cachexia, psoriasis, mesangial proliferative glomerulonephritis, Kaposi's sarcoma, AIDS-related lymphoma, inflammatory diseases and disorder (such as rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus).

The polypeptide of the invention comprises or essentially consists of one or more immunoglobulin single variable domains that specifically bind IL-6R. The one or more immunoglobulin single variable domains can be light chain variable domain sequences (e.g. a VL-sequence), or heavy chain variable domain sequences (e.g. a VH-sequence); more specifically, the immunoglobulin single variable domains can be heavy chain variable domain sequences that are derived from a conventional four-chain antibody or heavy chain variable domain sequences that are derived from a heavy chain antibody. For example, the immunoglobulin single variable domain may be a (single) domain, a "dAb" or dAb or a Nanobody (as defined herein, and including but not limited to a VHH sequence).

Preferred polypeptides of the invention comprise or essentially consist of one or more immunoglobulin single variable domains that comprise or essentially consists of 4 framework regions (FR1 to FR4, respectively) and 3 complementarity determining regions (CDR1 to CDR3, respectively), in which (Table A-1):
  a) CDR1 is chosen from the group consisting of: SEQ ID NO's: 17-19;
  b) CDR2 is chosen from the group consisting of: SEQ ID NO's: 21-28; and
  c) CDR3 is chosen from the group consisting of: SEQ ID NO's: 30-32.

Particularly preferred are polypeptides that comprise or essentially consist of one or more immunoglobulin single variable domains that have a CDR1 with SEQ ID NO: 17, a CDR2 with SEQ ID NO: 21 and a CDR3 with SEQ ID NO: 30.

In another preferred aspect, the one or more immunoglobulin single variable domain present in the polypeptide of the invention is selected from SEQ ID NOs: 1-10 (Table A-2), preferably SEQ ID NO: 1.

In another preferred aspect, the polypeptide of the invention may comprise an half-life extension moiety. In one aspect, the half-life extension moiety specifically binds a serum protein, preferably serum albumin, and in particular human serum albumin, thyroxine-binding protein, (human) transferrin, fibrinogen, an immunoglobulin such as IgG, IgE or IgM, or one of the serum proteins listed in WO 04/003019.

The half-life extension moiety may comprise or consist of an immunoglobulin single variable domain, such as e.g. a VHH domain, an humanized VHH domain, a camelized VH domain, a domain antibody, a single domain antibody and/or a "dAb". Preferred immunoglobulin single variable domains that bind serum albumin include SEQ ID NOs: 37-39 (Table A-4).

In a preferred aspect, the polypeptide of the invention is selected from SEQ ID NOs: 34-36, preferably SEQ ID NO: 34. Accordingly, the invention relates to a method for inhibiting IL-6 mediated signaling in a subject, said method comprising administering to the subject a polypeptide with SEQ ID NO: 34 in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein total sIL-6R levels in serum are increased to and maintained (throughout the treatment period) at at least 400 ng/ml. The invention thus also relates to a polypeptide with SEQ ID NO: 34 for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein total sIL-6R levels in serum are increased to and maintained (throughout the treatment period) at at least 400 ng/ml. The invention also relates to a polypeptide with SEQ ID NO: 34 for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein total sIL-6R levels in serum are increased to and maintained (throughout the treatment period) at at least 400 ng/ml.

In one aspect of the invention, the polypeptide with SEQ ID NO: 34 is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and total sIL-6R levels in serum are increased to and maintained at at least 400 ng/ml or more, such as at least 500 ng/ml, preferably at least 600 ng/ml, at least 650 ng/ml, or even at least 700 ng/ml or more.

In one aspect of the invention, the polypeptide with SEQ ID NO: 34 is administered in an amount from about 3 mg/kg to about 6 mg/kg (such as 3 mg/kg or 6 mg/kg) and total sIL-6R levels in serum are maintained at at least 400 ng/ml for up to 4 weeks or more, such as at least 5 weeks after administration, preferably at least 6 weeks or at least 7 weeks after administration, and most preferably at least 8 weeks after administration.

In one aspect of the invention, the polypeptide with SEQ ID NO: 34 is administered in an amount from about 3 mg/kg to about 6 mg/kg (such as 3 mg/kg or 6 mg/kg) and total sIL-6R levels in serum are increased to and maintained at at least 400 ng/ml or more, such as at least 500 ng/ml, preferably at least 600 ng/ml, at least 650 ng/ml, or even at least 700 ng/ml or more, for up to at least 4 weeks or more.

In another aspect, the invention relates to a method for inhibiting IL-6 mediated signaling in a subject, said method comprising administering to the subject a polypeptide with SEQ ID NO: 34 in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein total IL-6 levels in serum are increased to and maintained at at least 40 pg/ml. The invention thus also relates to a polypeptide with SEQ ID NO: 34 for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein total IL-6 levels in serum are increased to and maintained at at least 40 pg/ml. The invention also relates to a polypeptide with SEQ ID NO: 34 for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein total IL-6 levels in serum are increased to and maintained at at least 40 pg/ml.

In the method of the invention, the polypeptide with SEQ ID NO: 34 is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and total IL-6 levels in serum are increased to and maintained at at least 40 pg/ml or more, such as at least 50 pg/ml, preferably at least 60 pg/ml or more.

In one aspect of the invention, the polypeptide with SEQ ID NO: 34 is administered in an amount from about 3 mg/kg to about 6 mg/kg (such as 3 mg/kg or 6 mg/kg) and total IL-6 levels in serum are maintained at at least 40 pg/ml for up to 4 weeks or more, such as at least 5 weeks after administration, preferably at least 6 weeks or at least 7 weeks after administration, and most preferably at least 8 weeks after administration.

In the method of the invention, the polypeptide with SEQ ID NO: 34 is administered in an amount from about 3 mg/kg to about 6 mg/kg (such as 3 mg/kg or 6 mg/kg) and total IL-6 levels in serum are increased to and maintained at at least 40 pg/ml or more, such as at least 50 pg/ml, preferably at least 60 pg/ml or pore, for up to at least 4 weeks or more.

In a further aspect, the invention relates to a method for inhibiting IL-6 mediated signaling in a subject, said method comprising administering to the subject a polypeptide with SEQ ID NO: 34 in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein CRP levels in serum are decreased to and maintained below 10 mg/l. The invention thus also relates to a polypeptide with SEQ ID NO: 34 for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased to and maintained below 10 mg/l. The invention also relates to a polypeptide with SEQ ID NO: 34 for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased to and maintained below 10 mg/l.

In the method of the invention, the polypeptide with SEQ ID NO: 34 is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and CRP levels in serum are decreased to and maintained below 10 mg/l or less, such as below 9 mg/l, below 8 mg/l, more preferably below 7.5 mg/l, below 7 mg/l, below 6.5 mg/l, most preferably below 6 mg/l, below 5.5 mg/l or below 5 mg/l or lower.

In one aspect of the invention, the polypeptide with SEQ ID NO: 34 is administered in an amount from about 3 mg/kg to about 6 mg/kg (such as 3 mg/kg or 6 mg/kg) and CRP levels in serum are maintained below 10 mg/l for up to at least 4 weeks or more, such as at least 5 weeks after administration, preferably at least 6 weeks or at least 7 weeks after administration, and most preferably at least 8 weeks after administration.

In the method of the invention, the polypeptide with SEQ ID NO: 34 is administered in an amount from about 3 mg/kg to about 6 mg/kg (such as 3 mg/kg or 6 mg/kg) and CRP levels in serum are decreased to and maintained below 10 mg/l or less, such as below 9 mg/l, below 8 mg/l, more preferably below 7.5 mg/l, below 7 mg/l, below 6.5 mg/l, most preferably below 6 mg/l, below 5.5 mg/l or below 5 mg/l or lower, for up to at least 4 weeks or more.

In a specific aspect, when the subject is also receiving methotrexate (MTX) therapy, the baseline CRP levels (i.e. the CRP levels before dosing the polypeptide of the invention) in serum are most likely already below 10 mg/ml or less (unrelated to the anti-IL-6R therapy). Accordingly, "reduction of CRP levels in serum below 10 mg/l or less and maintenance of CRP levels in serum below 10 mg/l or less" cannot be used as a relevant marker for the pharmacodynamic effect of the polypeptide with SEQ ID NO: 34 in subjects that also receive MTX therapy, but only in subjects that do not receive methotrexate (MTX) therapy.

In a further aspect, the invention relates to a method for inhibiting IL-6 mediated signaling in a subject, said method comprising administering to the subject a polypeptide with SEQ ID NO: 34 in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein CRP levels in serum are decreased by and maintained at 50% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased by and maintained at 50% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein CRP levels in serum are decreased by and maintained at 50% or more (reduction) compared to baseline (i.e. pre-treatment or normal) levels.

In one aspect of the invention, the polypeptide with SEQ ID NO: 34 is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and CRP levels in serum are decreased by and maintained at 50% or more (reduction) compared to baseline (i.e. pre-treatment or normal) levels, at 30% or more, 40% or more, 50% or more, 60% or more, or even 70% or more reduction compared to baseline (i.e. pre-treatment or normal) levels.

In one aspect of the invention, the polypeptide with SEQ ID NO: 34 is administered in an amount from about 3 mg/kg to about 6 mg/kg (such as 3 mg/kg or 6 mg/kg) and CRP levels in serum are decreased by and maintained at 50% or more reduction compared to baseline (i.e. pre-treatment or normal) levels for up to at least 4 weeks or more, such as at least 5 weeks after administration, preferably at least 6 weeks or at least 7 weeks after administration, and most preferably at least 8 weeks after administration.

In one aspect of the invention, the polypeptide with SEQ ID NO: 34 is administered in an amount from about 3 mg/kg to about 6 mg/kg (such as 3 mg/kg or 6 mg/kg) and CRP levels in serum are decreased by and maintained at 50% or more (reduction) compared to baseline (i.e. pre-treatment or normal) levels, at 30% or more, 40% or more, 50% or more, 60% or more, or even 70% or more reduction compared to baseline (i.e. pre-treatment or normal) levels, for up to at least 4 weeks or more.

In a further aspect, the invention relates to a method for inhibiting IL-6 mediated signaling in a subject, said method comprising administering to the subject a polypeptide with SEQ ID NO: 34 in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein ESR levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein ESR levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein ESR levels in serum are decreased by and maintained at 30% or more (reduction) compared to baseline (i.e. pre-treatment or normal) levels.

In one aspect of the invention, the polypeptide with SEQ ID NO: 34 is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and ESR levels in serum are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels.

In one aspect of the invention, the polypeptide with SEQ ID NO: 34 is administered in an amount from about 3 mg/kg to about 6 mg/kg (such as 3 mg/kg or 6 mg/kg) and ESR levels in serum are decreased by and maintained at 30% or more reduction compared to baseline (i.e. pre-treatment or normal) levels for up to at least 4 weeks or more, such as at least 5 weeks after administration, preferably at least 6 weeks or at least 7 weeks after administration, and most preferably at least 8 weeks after administration.

In one aspect of the invention, the polypeptide with SEQ ID NO: 34 is administered in an amount from about 3 mg/kg to about 6 mg/kg (such as 3 mg/kg or 6 mg/kg) and ESR levels in serum are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels, for up to at least 4 weeks or more.

In a further aspect, the invention relates to a method for inhibiting IL-6 mediated signaling in a subject, said method comprising administering to the subject a polypeptide with SEQ ID NO: 34 in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein fibrinogen levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein fibrinogen levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein fibrinogen levels in serum are decreased by and maintained at 30% or more (reduction) compared to baseline (i.e. pre-treatment or normal) levels.

In one aspect of the invention, the polypeptide with SEQ ID NO: 34 is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and fibrinogen levels in serum are decreased by and maintained at 30% or more (reduction) compared to baseline (i.e. pre-treatment or normal) levels, at 20% or more, 30% or more, 40% or more, or even 50% or more reduction compared to baseline (i.e. pre-treatment or normal) levels.

In one aspect of the invention, the polypeptide with SEQ ID NO: 34 is administered in an amount from about 3 mg/kg to about 6 mg/kg (such as 3 mg/kg or 6 mg/kg) and fibrinogen levels in serum are decreased by and maintained at 30% or more reduction compared to baseline (i.e. pre-treatment or normal) levels for up to at least 4 weeks or more, such as at least 5 weeks after administration, preferably at least 6 weeks or at least 7 weeks after administration, and most preferably at least 8 weeks after administration.

In one aspect of the invention, the polypeptide with SEQ ID NO: 34 is administered in an amount from about 3 mg/kg to about 6 mg/kg (such as 3 mg/kg or 6 mg/kg) and fibrinogen levels in serum are decreased by and maintained at 30% or more (reduction) compared to baseline (i.e. pre-treatment or normal) levels, at 20% or more, 30% or more, 40% or more, or even 50% or more reduction compared to baseline (i.e. pre-treatment or normal) levels for up to at least 4 weeks or more.

In a further aspect, the invention relates to a method for inhibiting IL-6 mediated signaling in a subject, said method comprising administering to the subject a polypeptide with SEQ ID NO: 34 in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks), wherein serum amyloid A levels are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein serum amyloid A levels are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and wherein serum amyloid A levels are decreased by and maintained at 30% or more (reduction) compared to baseline (i.e. pre-treatment or normal) levels.

In one aspect of the invention, the polypeptide with SEQ ID NO: 34 is administered in an amount from about 3 mg/kg to about 6 mg/kg every 4 to 8 weeks (such as e.g. 3 mg/kg every 4 weeks, 6 mg/kg every 4 weeks, or 6 mg/kg every 8 weeks) and serum amyloid A levels are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels.

In one aspect of the invention, the polypeptide with SEQ ID NO: 34 is administered in an amount from about 3 mg/kg to about 6 mg/kg (such as 3 mg/kg or 6 mg/kg) and serum amyloid A levels are decreased by and maintained at 30% or more reduction compared to baseline (i.e. pre-treatment or normal) levels for up to at least 4 weeks or more, such as at least 5 weeks after administration, preferably at least 6 weeks or at least 7 weeks after administration, and most preferably at least 8 weeks after administration.

In one aspect of the invention, the polypeptide with SEQ ID NO: 34 is administered in an amount from about 3 mg/kg to about 6 mg/kg (such as 3 mg/kg or 6 mg/kg) and serum amyloid A levels are decreased by and maintained at 30% or more (reduction) compared to baseline (i.e. pre-treatment or normal) levels, such as at 40% or more, 50% or more, 60% or more, or even 70% or more reduction compared to baseline (i.e. pre-treatment or normal) levels for up to at least 4 weeks or more.

FIGURE LEGENDS

FIG. 1. Relationship of soluble IL-6 receptor, free tocilizumab and C-reactive protein in serum following a single infusion of tocilizumab (10 mg/kg) to rheumatoid arthritis patients (n=12). sIL-6: Soluble IL-6. Data taken from Schmitt et al. (2010, Clin. Pharmacol. Ther. 89: 735-740).

Figure 2:
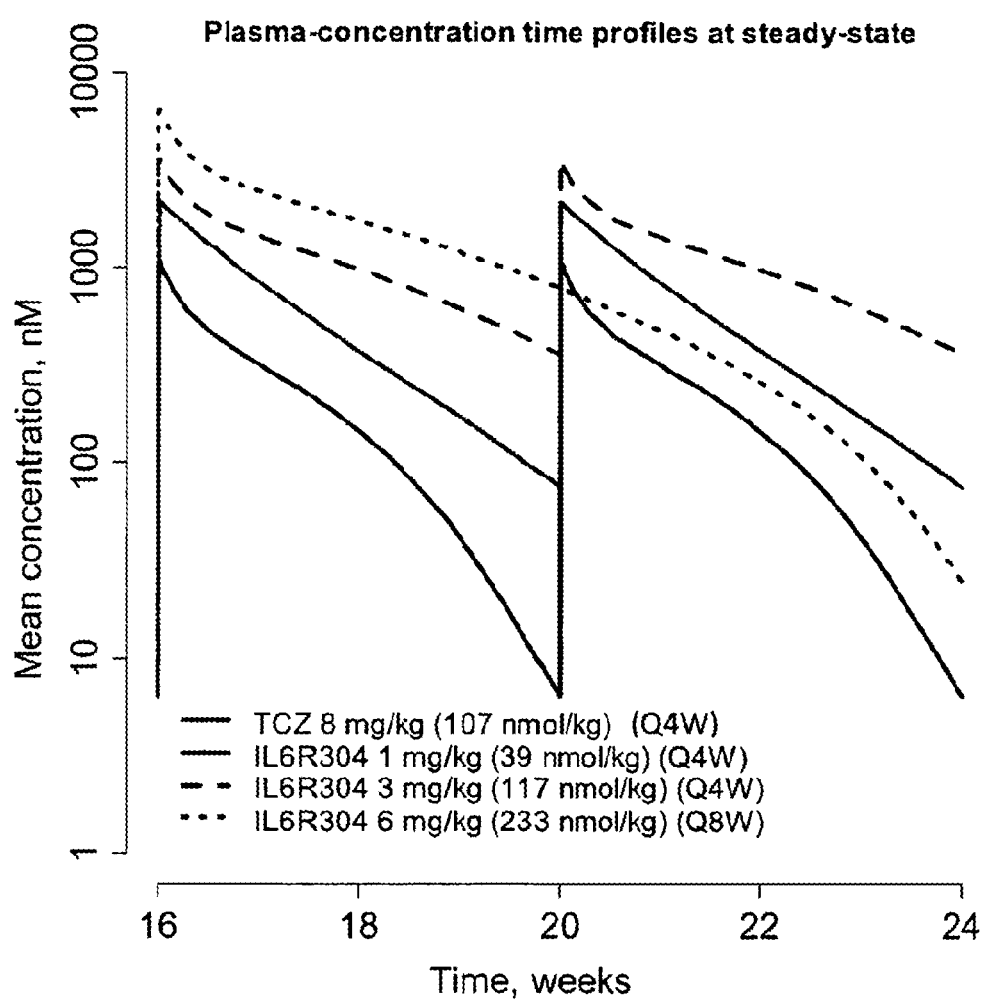

FIG. 2. Median IL6R304 plasma profiles expected after repeated IL6R304 administration of 1 mg/kg (39 nmol/kg) Q4W, 3 mg/kg (117 nmol/kg) Q4W and 6 mg/kg (233 nmol/kg) Q8W. The median tocilizumab (TCZ) profile after repeated dose of 8 mg/kg (107 nmol/kg) Q4W, reproduced from a published model, is added for comparison (Frey N., Grange S. and Woodworth T. 2010, Population Pharmacokinetic Analysis of Tocilizumab in Patients with Rheumatoid Arthritis. J. Clin. Pharm. 50: 754-766).

Figure 3:
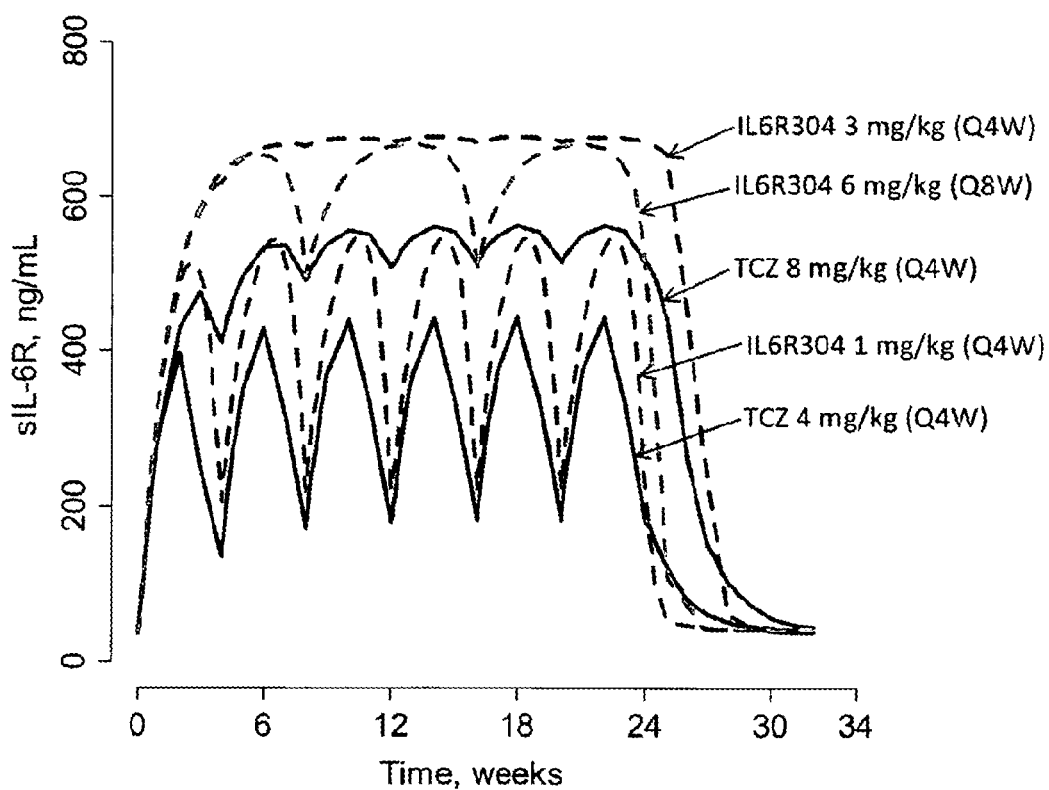

FIG. 3. Median sIL-6R plasma profiles expected after repeated IL6R304 administration of 1 mg/kg (39 nmol/kg) Q4W, 3 mg/kg (117 nmol/kg) Q4W and 6 mg/kg (233 nmol/kg) Q8W. The median tocilizumab (TCZ) profile after repeated dose of 4 mg/kg (54 nmol/kg) Q4W or 8 mg/kg (107 nmol/kg) Q4W, reproduced from a published model (Levi et al. 2012, J. Clin. Pharmacol. February 14. [Epub ahead of print]; Gibiansky and Frey 2012, J. Pharmacokinet. Pharmacodyn. 39(1): 5-16; Zhang and Peck 2011, Expert Rev. Clin. Pharmacol. 4(5): 539-55), is added for comparison.

Figure 4:
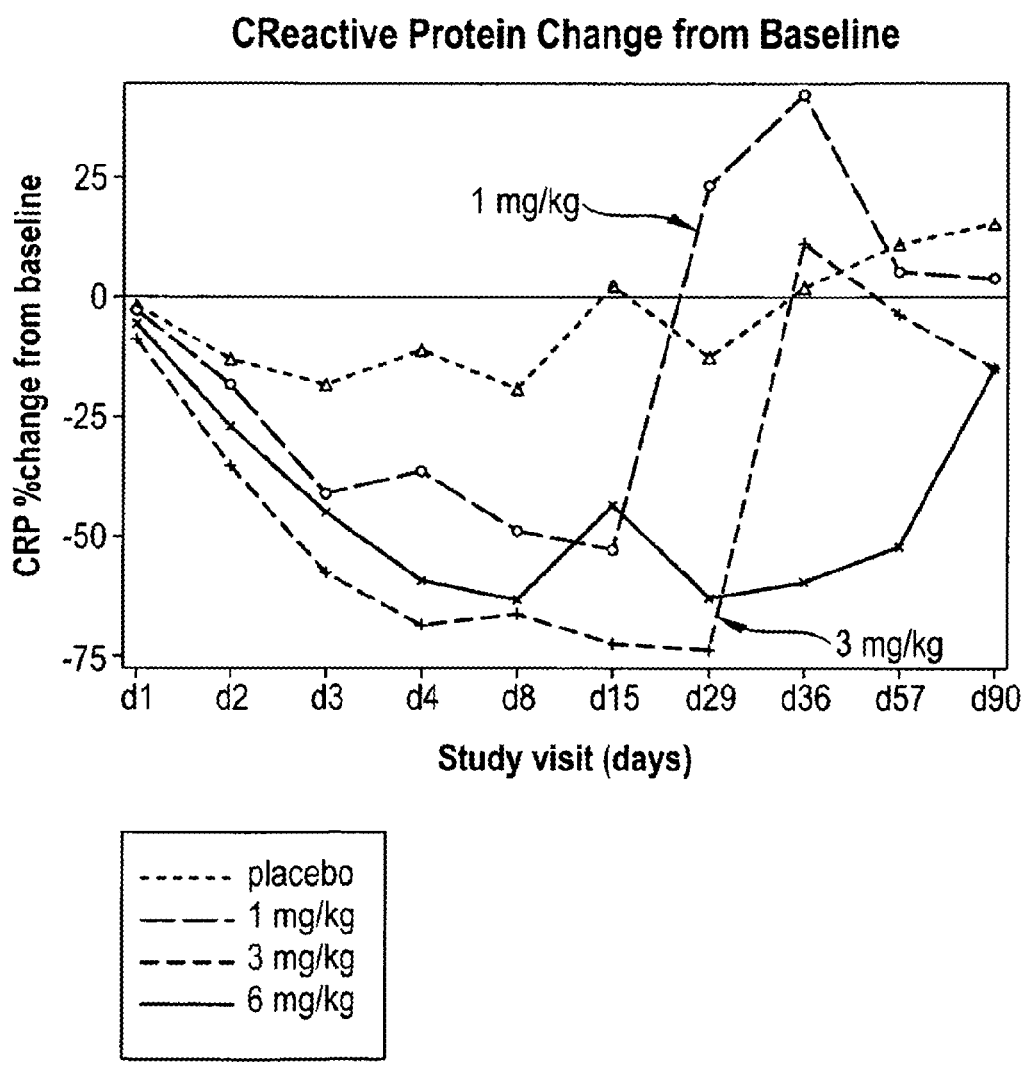

FIG. 4. C-Reactive Protein (CRP) changes (in %) from baseline (i.e. % reduction compared to baseline) in the different patient groups during the SAD study with IL6R304 as described in Example 4.

Figure 5:
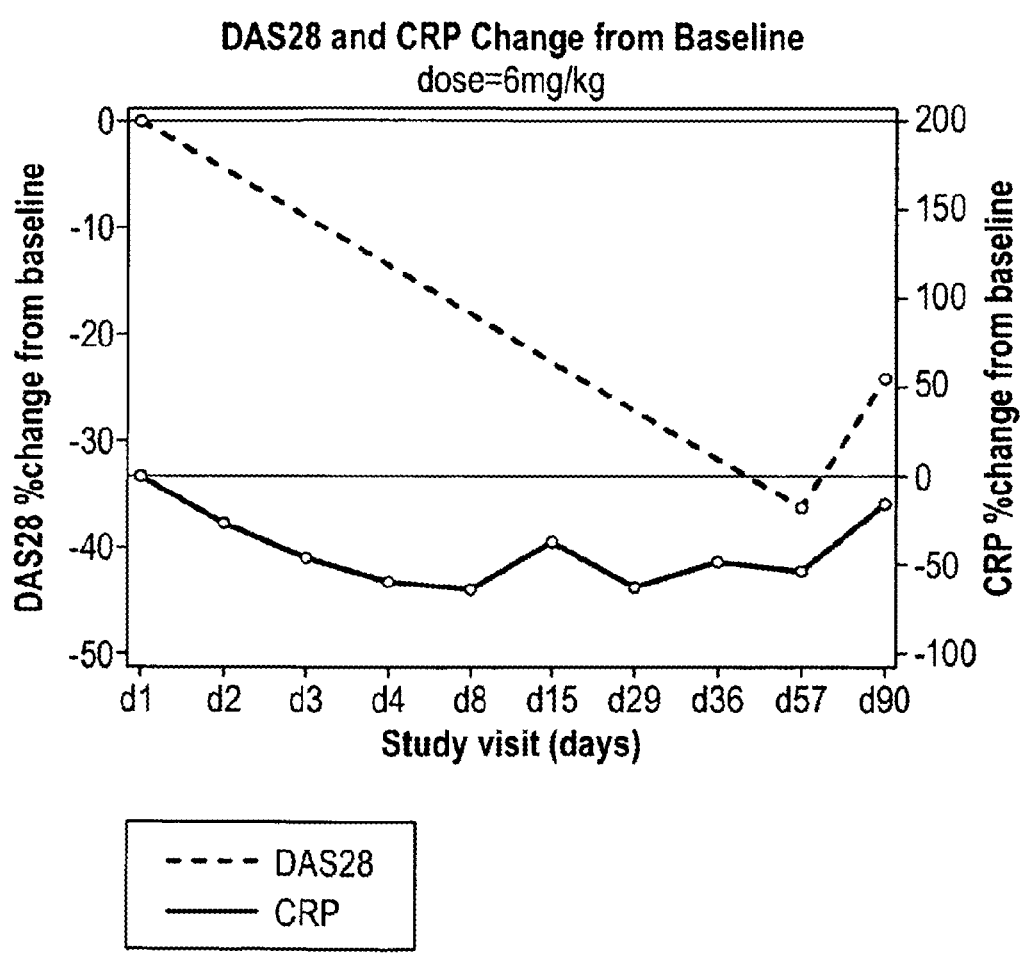

FIG. 5. DAS28 and CRP changes (in %) from baseline (i.e. % reduction compared to baseline) in the 6 mg/kg dosing group during the SAD study with IL6R304.

Figure 6:
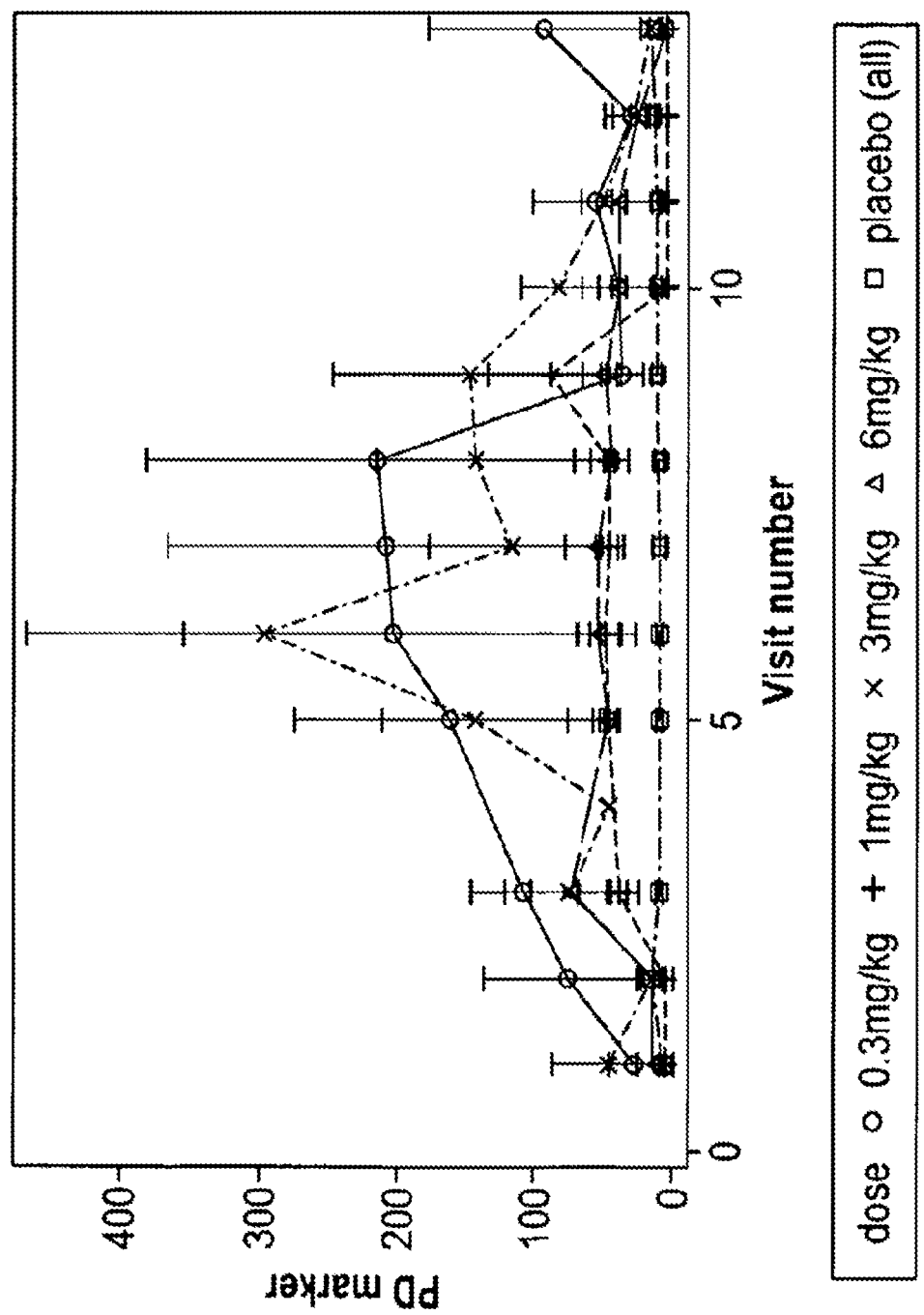

FIG. 6. Changes in IL-6 levels (pg/ml) for the different treatment groups during the SAD study with IL6R304. Visit 1: Day −28 to −2; Visit 2: Day 1 (pre-dose); Visit 3: Day 1 (8 hrs post-dose); Visit 4: Unscheduled Lab 1; Visit 5: Day 2 (24 hrs post-dose); Visit 6: Day 3 (48 hrs post-dose); Visit 7: Day 4 (72 hrs post-dose); Visit 8: Day 8; Visit 9: Day 15; Visit 10: Day 29; Visit 11: Day 36; Visit 12: Day 57; Visit 13: Follow-up.

Figure 7:
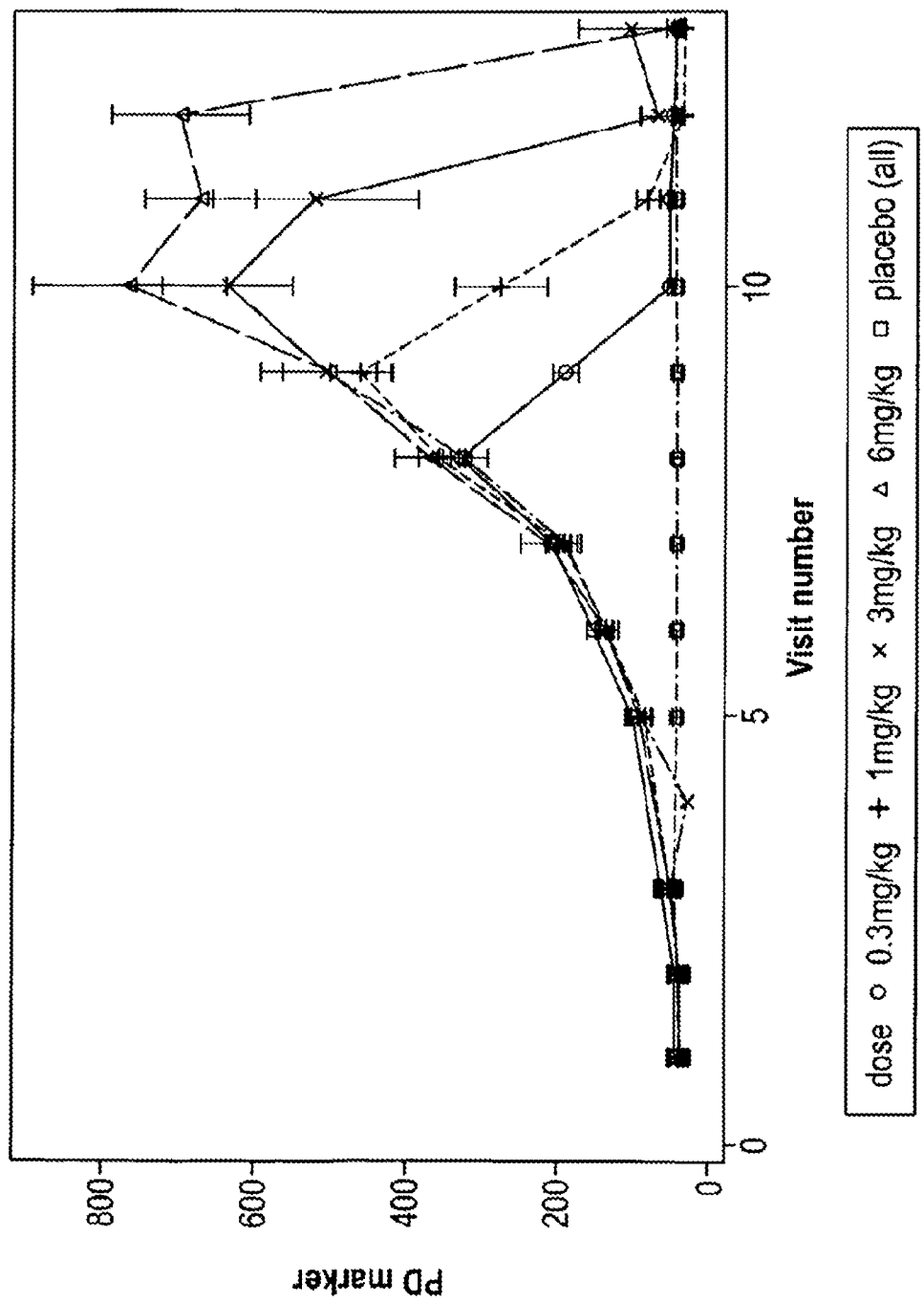

FIG. 7. Changes in sIL-6R levels (ng/ml) for the different treatment groups during the SAD study with IL6R304. Visit 1: Day −28 to −2; Visit 2: Day 1 (pre-dose); Visit 3: Day 1 (8 hrs post-dose); Visit 4: Unscheduled Lab 1; Visit 5: Day 2 (24 hrs post-dose); Visit 6: Day 3 (48 hrs post-dose); Visit 7: Day 4 (72 hrs post-dose); Visit 8: Day 8; Visit 9: Day 15; Visit 10: Day 29; Visit 11: Day 36; Visit 12: Day 57; Visit 13: Follow-up.

FIG. 8. Mean (±SE) DAS28 and CRP changes (in %) from baseline (i.e. % reduction compared to baseline). Single symbols indicated DAS28 scores. Lines with symbols indicate CRP changes.

DETAILED DESCRIPTION

Methods of the Invention

The Applicant has discovered that the administration to human subjects of polypeptides as described herein that specifically bind IL-6R (referred to herein as "polypeptide(s) of the invention" as further defined herein) provides an unexpectedly sustained, prolonged effect on inhibition of IL-6 mediated signaling in the human subjects as observed through changes in relevant biomarkers (such as serum IL-6R, serum IL-6, serum CRP, serum ESR, serum fibrinogen and/or serum amyloid A). Therefore, the invention relates to the use of the polypeptides of the invention to inhibit IL-6 mediated signaling in a subject for unexpectedly prolonged periods of time, particularly in view of the doses administered. The invention also provides for less frequent and/or lower dose administration to a subject of the polypeptides of the invention, while still maintaining effective inhibition of IL-6 mediated signaling in the subject at unexpectedly prolonged periods of time. Accordingly, methods are provided for inhibiting IL-6 mediated signaling in a subject by administering to the subject a polypeptide of the invention that specifically binds IL-6R, wherein the amount of the polypeptide administered is effective to change one or more markers of IL-6 mediated signaling, such as total sIL-6R, total IL-6, CRP, ESR, fibrinogen and/or serum amyloid A for unexpectedly prolonged periods of time.

Various biomarkers are available for measuring IL-6 mediated signaling. In a preferred aspect, markers of IL-6 mediated signaling are selected from soluble interleukin-6 receptor (sIL-6R), interleukin-6 (IL-6), C-reactive protein (CRP), Erythrocytes Sedimentation Rate (ESR), fibrinogen and Serum Amyloid A. These markers can be measured using standard methods known to and used by the skilled person, such as various immunologically based assays, including enzyme-linked immunosorbent assays (ELISA; also known as an enzyme immunoassay (EIA)), radioimmunoassays or immunoenzymetric assays. Chemical, colorimetric and enzymatic based assays also may be used when suitable.

Soluble IL-6R (sIL-6R) includes serum IL-6R free from IL-6 and serum IL-6R free from polypeptide of the invention as well as serum IL-6R in complex with IL-6, serum IL-6R in complex with IL-6 and gp130 and serum IL-6R in an immune complex with the polypeptide of the invention. Serum sIL-6R is free or bound to IL-6 before administration of the polypeptide of the invention. Following administration of the polypeptide of the invention, the sIL-6R binds to the polypeptide of the invention to form a sIL-6R/polypeptide of the invention immune complex.

Serum sIL-6R levels can be determined by any method as described herein and/or known in the art. Preferred and easy methods for determining sIL-6R levels include immunoassays such as flow cytometry, inhibition assay, immunoprecipitation, immunohistochemistry (Frozen) and ELISA (such as e.g. the Quantikine Human IL-6sR kit from R&D Systems, Minneapolis, Minn.; E91815Hu ELISA Kit for Interleukin 6 Receptor (IL6R) from Uscn Life Science Inc, Wuhan, China; SEK10398 human IL6R/CD126 ELISA kit from Sino Biological, Inc., Beijing, China; EL10034 Interleukin 6 Soluble Receptor (IL 6 sR) ELISA Kit, human from Biosupply, UK; or any other assay such as e.g. the assays described in the example section).

IL-6 includes serum IL-6 free from IL-6R as well as serum IL-6 in complex with IL-6R and serum IL-6 in complex with IL-6R and sgp130. Serum IL-6 levels are free or bound to IL-6R before administration of the polypeptide of the invention. Following administration of the polypeptide of the invention IL-6 temporarily increases. This increase is most likely caused by IL-6R blockade inhibiting clearance of IL-6 from the blood.

Serum IL-6 levels can be determined by any method as described herein and/or known in the art. Preferred and easy methods for determining IL-6 levels include immunoassays such as flow cytometry, inhibition assay, immunoprecipitation, immunohistochemistry (Frozen) and ELISA (such as e.g. Human IL-6 Quantiglo ELISA Kit" from R&D Systems, Minneapolis, Minn. (cat #Q6000B); Human IL-6 ELISA Ready-SET-Go!® from eBioscience Ltd., Hatfield, United Kingdom; Human Interleukin-6 (IL6/IFNB2) ELISA Kit from Sino Biological Inc., Beijing, China; Interleukin 6 (IL 6) ELISA Kit, human from Biosupply, UK).

C-reactive protein (CRP) is an acute-phase protein found in the blood, of which the levels rise in response to inflammation. C-reactive protein (CRP) is synthesized by hepatocytes as a direct effect of IL-6 stimulation. Elevated CRP levels are an indication of inflammation intensity in RA. It has been demonstrated that blockade of IL-6 mediated signaling (such as by blockade of IL-6R) can lower CRP levels (Nishimoto et al. 2008, Blood 112: 3959-3964).

The level of C-reactive protein in serum can be determined by any method as described herein and/or known in the art. Preferred and easy methods include immunoassays such as the C-reactive protein detection kit (Difco Laboratories, Detroit, Mich., US), the Human C-Reactive Protein ELISA Kit (Abnova Corporation, Taipei, Taiwan R.O.C.), the Human CRP ELISA Kit, High sensitivity (American Diagnostic GmbH, Pfungstadt, Germany), the Human CRP ELISA Kit (Antigenix America Inc., N.Y., US) and the IMMAGE Immunochemistry System (Beckman Coulter Inc., Brea, Calif., US).

Erythrocytye Sedimentation Rate (ESR) is the rate at which red blood cells sediment in a period of 1 hour. It is a common hematology test, and is a non-specific measure of inflammation. To perform the test, anticoagulated blood is placed in an upright tube, known as a Westergren tube, and the rate at which the red blood cells fall is measured and reported in mm/h. The ESR is governed by the balance between pro-sedimentation factors, mainly fibrinogen, and those factors resisting sedimentation, namely the negative charge of the erythrocytes (zeta potential). When an inflammatory process is present, the high proportion of fibrinogen in the blood causes red blood cells to stick to each other. The red cells form stacks called 'rouleaux,' which settle faster.

The ESR can further be determined (without being limiting) with the Greiner ESR tube (Cat. No. 454076), or with the Preanalytics—VACUETTE® Evacuated Collection Tubes (Greiner Bio-One, Wemmel, Belgium), with Sediplus® S 2000 (Sarstedt; Nümbrecht, Germany), or with Seditainer™ (Product Number: 366016; Becton Dickinson, N.J. USA).

Fibrinogen (factor I) is a soluble 340 kDa glycoprotein, synthesized in the liver by hepatocytes, that is converted by thrombin into fibrin during blood coagulation. The concentration in blood plasma is 1.5-4.0 g/L (normally measured using the Clauss method) or about 7 μM. Recent research has shown that fibrin plays a key role in the inflammatory response and development of rheumatoid arthritis. It may be elevated in any form of inflammation, as it is an acute-phase protein (Gilliam et al. 2011, Pediatric Rheumatology 9: 8).

The fibrinogen level can be determined by any method as described above and/or known in the art. Preferred and easy methods include (without being limiting) the STA® Fibrinogen 5 (Stago, Parsippany, N.J., USA) for quantitative determination of fibrinogen by the Clauss method, the STA Compact®, a fully automated, benchtop, Haemostasis analyser for clotting, chromogenic and immunological assays using random access mode (Stago, Parsippany, N.J., USA), ACL TOP® 500 CTS (Beckman Coulter Inc., Brea, Calif., US) and Ceveron® alpha (TC technoclone, Vienna, Austria).

Serum amyloid A (SAA) proteins are a family of apolipoproteins associated with high-density lipoprotein (HDL) in plasma. Acute-phase serum amyloid A proteins (A-SAAs) are secreted during the acute phase of inflammation. A-SAAs are implicated in several chronic inflammatory diseases, such as amyloidosis, atherosclerosis, and rheumatoid arthritis (Zhang et al. 2005, J. Immunol. 174: 8125-34).

The level of serum amyloid A in serum can be determined by any method as described above and/or known in the art. Preferred and easy methods include the Phase SAA Assay (Tridelta Development Ltd. Maynooth, County Kildare, Ireland; Cat. no. TP-802), or the ELISA assay as described in the Examples section.

In one aspect, methods are provided for inhibiting IL-6 mediated signaling in a subject by administering to the subject a polypeptide of the invention, wherein the amount of the polypeptide administered is effective to increase total sIL-6R levels in serum to at least 400 ng/ml and maintain total sIL-6R levels in serum at at least 400 ng/ml. Preferably total sIL-6R levels are increased to and maintained at at least 450 ng/ml, at least 500 ng/ml, more preferably at least 550 ng/ml or even at least 600 ng/ml, at least 650 ng/ml, or even at least 700 ng/ml or more.

In another aspect, methods are provided for inhibiting IL-6 mediated signaling in a subject by administering to the subject a polypeptide of the invention, wherein the amount of the polypeptide administered is effective to increase total IL-6 levels in serum to at least 40 pg/ml and maintain total IL-6 levels in serum at at least 40 pg/ml. Preferably total IL-6 levels are increased to and maintained at at least 45 pg/ml, at least 50 pg/ml, more preferably at least 55 pg/ml or even at least 60 pg/ml or more.

In yet another aspect, methods are provided for inhibiting IL-6 mediated signaling in a subject by administering to the subject a polypeptide of the invention, wherein the amount of the polypeptide administered is effective to reduce CRP levels below 10 mg/l and maintain CRP levels below 10 mg/l. Preferably CRP levels are reduced to and maintained below 9 mg/l or below 8 mg/l, more preferably below 7.5 mg/l, below 7 mg/l or below 6.5 mg/l, or even below 6 mg/l, below 5.5 mg/l, below 5 mg/l or less.

In a specific aspect, when the subject is also receiving methotrexate (MTX) therapy, the baseline CRP levels (i.e. the CRP levels before dosing the polypeptide of the invention) in serum are most likely already below 10 mg/ml or less (unrelated to the anti-IL-6R therapy). Accordingly, "reduction of CRP levels in serum below 10 mg/l or less and maintenance of CRP levels in serum below 10 mg/l or less" cannot be used as a relevant marker for the pharmacodynamic effect of the polypeptide of the invention in such subjects (that also receive MTX therapy), but only in subjects that do not receive methotrexate (MTX) therapy.

Therefore, in certain cases (such as when the subject is also receiving MTX therapy), changes in CRP levels can also be determined as "% reduction compared to baseline (i.e. compared to CRP levels before treatment with the polypeptide of the invention (pre-treatment) and/or at normal levels)".

Accordingly, in yet another aspect, methods are provided for inhibiting IL-6 mediated signaling in a subject by administering to the subject a polypeptide of the invention, wherein the amount of the polypeptide administered is effective to reduce CRP levels in serum by 50% or more compared to baseline (i.e. pre-treatment or normal) levels and to maintain CRP levels in serum at 50% or more reduction compared to baseline levels. Preferably CRP levels are reduced by and maintained at 30% or more, 40% or more, 50% or more, 60% or more, or even 70% or more (reduction) compared to baseline (i.e. pre-treatment or normal) levels.

In yet another aspect, methods are provided for inhibiting IL-6 mediated signaling in a subject by administering to the subject a polypeptide of the invention, wherein the amount of the polypeptide administered is effective to reduce ESR levels in serum by 30% or more compared to baseline (i.e. pre-treatment or normal) levels and to maintain ESR levels in serum at 30% or more reduction compared to baseline levels. Preferably ESR levels are reduced by and maintained at 40% or more, 50% or more, 60% or more, or even 70% or more (reduction) compared to baseline (i.e. pre-treatment or normal) levels.

In yet another aspect, methods are provided for inhibiting IL-6 mediated signaling in a subject by administering to the subject a polypeptide of the invention, wherein the amount of the polypeptide administered is effective to reduce fibrinogen levels in serum by 30% or more compared to baseline (i.e. pre-treatment or normal) levels and to maintain fibrinogen levels in serum at 30% or more reduction compared to baseline levels. Preferably fibrinogen levels are reduced by and maintained at 20% or more, 30% or more, 40% or more, or even 50% or more (reduction) compared to baseline (i.e. pre-treatment or normal) levels.

In yet another aspect, methods are provided for inhibiting IL-6 mediated signaling in a subject by administering to the subject a polypeptide of the invention, wherein the amount of the polypeptide administered is effective to reduce serum amyloid A levels by 30% or more compared to baseline (i.e. pre-treatment or normal) levels and to maintain serum amyloid A levels at 30% or more reduction compared to baseline levels. Preferably serum amyloid A levels are reduced by and maintained at 40% or more, 50% or more, 60% or more, or even 70% or more (reduction) compared to baseline (i.e. pre-treatment or normal) levels.

In another aspect, methods for inhibiting IL-6 mediated signaling in a subject are provided that include administering to the subject a polypeptide of the invention, wherein the amount of the polypeptide administered is effective to change one or more markers of IL-6 mediated signaling for at least 4 weeks after administration. Certain amounts of the polypeptide of the invention may change the one or more markers of IL-6 mediated signaling for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

Accordingly, the present invention provides methods for inhibiting IL-6 mediated signaling in a subject that include administering to the subject a polypeptide of the invention, wherein the amount of the polypeptide administered is effective to increase total sIL-6R levels in serum for at least 4 weeks after administration. In some embodiments, the serum level of sIL-6R is increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more. The increase in the serum level of sIL-6R can persist for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

In a specific aspect, the levels of sIL-6R are increased to and maintained at at least 400 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of sIL-6R are increased to and maintained at at least 450 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of sIL-6R are increased to and maintained at at least 500 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of sIL-6R are increased to and maintained at at least 550 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of sIL-6R are increased to and maintained at at least 600 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of sIL-6R are increased to and maintained at at least 650 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of sIL-6R are increased to and maintained at at least 700 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another aspect of the invention, methods for inhibiting IL-6 mediated signaling in a subject are provided that include administering to the subject a polypeptide of the invention, wherein the amount of the polypeptide administered is effective to increase total IL-6 levels in serum for at least 4 weeks after administration. In some embodiments, the serum level of IL-6 is increased to and maintained at at least 40 pg/ml or more, such as at least 45 pg/ml, at least 50 pg/ml, more preferably at least 55 pg/ml or even at least 60 pg/ml or more. The increase in the serum level of IL-6 can persist for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

In a specific aspect, the levels of IL-6 are increased to and maintained at at least 40 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of IL-6 are increased to and maintained at at least 45 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of IL-6 are increased to and maintained at at least 50 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of IL-6 are increased to and maintained at at least 55 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of IL-6 are increased to and maintained at at least 60 pg/ml or more for up to at least 5 weeks, at least 6 weeks, at least 7 weeks, at least 8 weeks, at least 9 weeks, at least 10 weeks, at least 11 weeks, or even at least 12 weeks after administration.

In another aspect of the invention, methods for inhibiting IL-6 mediated signaling in a subject are provided that include administering to the subject a polypeptide of the invention, wherein the amount of the polypeptide administered is effective to reduce CRP levels in serum for at least 4 weeks after administration. In some embodiments, the serum level of CRP are reduced to and maintained below 10 mg/l, such as below 9 mg/l or below 8 mg/l, more preferably below 7.5 mg/l, below 7 mg/l or below 6.5 mg/l, or even below 6 mg/l, below 5.5 mg/l, below 5 mg/l or less. The reduction in the serum level of CRP can persist for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

In a specific aspect, the levels of CRP are reduced to and maintained below 10 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 9 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 8 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 7.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 7 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 6.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 6 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 5.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced to and maintained below 5 mg/l or less for up to at least 5 weeks, at least 6 weeks, at least 7 weeks, at least 8 weeks, at least 9 weeks, at least 10 weeks, at least 11 weeks, or even at least 12 weeks after administration.

In a specific aspect, when the subject is also receiving methotrexate (MTX) therapy, the baseline CRP levels (i.e. the CRP levels before dosing the polypeptide of the invention) in serum are most likely already below 10 mg/ml or less (unrelated to the anti-IL-6R therapy). Accordingly, "reduction of CRP levels in serum below 10 mg/l or less and maintenance of CRP levels in serum below 10 mg/l or less" cannot be used as a relevant marker for the pharmacodynamic effect of the polypeptide of the invention in subjects that also receive MTX therapy, but only in subjects that do not receive methotrexate (MTX) therapy.

In another aspect of the invention, methods for inhibiting IL-6 mediated signaling in a subject are provided that include administering to the subject a polypeptide of the invention, wherein the amount of the polypeptide administered is effective to reduce CRP levels in serum for at least 4 weeks after administration. In some embodiments, the serum level of CRP are reduced by and maintained at 30% or more, 40% or more, 50% or more, 60% or more, or even 70% or more (reduction) compared to baseline (i.e. pre-treatment or normal) levels. The reduction in the serum level of CRP can persist for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

In a specific aspect, the levels of CRP are reduced by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced by and maintained at 45% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced by and maintained at 55% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of CRP are reduced by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another aspect of the invention, methods for inhibiting IL-6 mediated signaling in a subject are provided that include administering to the subject a polypeptide of the invention, wherein the amount of the polypeptide administered is effective to reduce ESR levels in serum for at least 4 weeks after administration. In some embodiments, the serum levels of ESR are reduced by and maintained at 30% or more, 40% or more, 50% or more, 60% or more, or even 70% or more (reduction) compared to baseline (i.e. pre-treatment or normal) levels. The reduction in the serum level of ESR can persist for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

In a specific aspect, the levels of ESR are reduced by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of ESR are reduced by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of ESR are reduced by and maintained at 45% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of ESR are reduced by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of ESR are reduced by and maintained at 55% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of ESR are reduced by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of ESR are reduced by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another aspect of the invention, methods for inhibiting IL-6 mediated signaling in a subject are provided that include administering to the subject a polypeptide of the invention, wherein the amount of the polypeptide administered is effective to reduce fibrinogen levels in serum for at least 4 weeks after administration. In some embodiments, the serum levels of fibrinogen are reduced by and maintained at 20% or more, 30% or more, 40% or more, or even 50% or more (reduction) compared to baseline (i.e. pre-treatment or normal) levels. The reduction in the serum level of fibrinogen can persist for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

In a specific aspect, the levels of fibrinogen are reduced by and maintained at 20% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of fibrinogen are reduced by and maintained at 25% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of fibrinogen are reduced by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of fibrinogen are reduced by and maintained at 35% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of fibrinogen are reduced by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the levels of fibrinogen are reduced by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another aspect of the invention, methods for inhibiting IL-6 mediated signaling in a subject are provided that include administering to the subject a polypeptide of the invention, wherein the amount of the polypeptide administered is effective to reduce serum amyloid A levels for at least 4 weeks after administration. In some embodiments, the serum amyloid A levels are reduced by and maintained at 30% or more, 40% or more, 50% or more, 60% or more, 70% or more (reduction) compared to baseline (i.e. pre-treatment or normal) levels. The reduction in the serum amyloid A level can persist for longer periods of time, such as at least 5 weeks, at least 6 weeks, at least 7 weeks, at least 8 weeks, at least 9 weeks, at least 10 weeks, at least 11 weeks, or even at least 12 weeks; for example (including the ends of each range) 4-5 weeks, 5-6 weeks, 6-7 weeks, 7-8 weeks, 8-9 weeks, 9-10 weeks, 10-11 weeks, 11-12 weeks, 4-6 weeks, 5-7 weeks, 6-8 weeks, 7-9 weeks, 8-10 weeks, 9-11 weeks, 10-12 weeks, 4-7 weeks, 5-8 weeks, 6-9 weeks, 7-10 weeks, 8-11 weeks, 9-12 weeks, 4-8 weeks, 5-9 weeks, 6-10 weeks, 7-11 weeks, 8-12 weeks, 4-9 weeks, 5-10 weeks, 6-11 weeks, 7-12 weeks, 4-10 weeks, 5-11 weeks, 6-12 weeks, 4-11 weeks, 5-12 weeks, 4-12 weeks.

In a specific aspect, the serum amyloid A levels are reduced by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the serum amyloid A levels are reduced by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the serum amyloid A levels are reduced by and maintained at 45% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the serum amyloid A levels are reduced by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the serum amyloid A levels are reduced by and maintained at 55% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the serum amyloid A levels are reduced by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, the serum amyloid A levels are reduced by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Polypeptide of the Invention
Immunoglobulin Single Variable Domain

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs.

The term "immunoglobulin single variable domain" and "single variable domain" hence does not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a VL-sequence) or a suitable fragment thereof; or a heavy chain variable domain sequence (e.g. a VH-sequence or VHH sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a VH/VL interaction—to form a functional antigen binding domain).

In one embodiment of the invention, the immunoglobulin single variable domains are light chain variable domain sequences (e.g. a VL-sequence), or heavy chain variable domain sequences (e.g. a VH-sequence); more specifically, the immunoglobulin single variable domains can be heavy chain variable domain sequences that are derived from a conventional four-chain antibody or heavy chain variable domain sequences that are derived from a heavy chain antibody.

For a general description of heavy chain antibodies and the variable domains thereof, reference is inter alia made to the prior art cited herein, as well as to the prior art mentioned on page 59 of WO 08/020079 and to the list of references mentioned on pages 41-43 of the International application WO 06/040153, which prior art and references are incorporated herein by reference.

For example, the single variable domain or immunoglobulin single variable domain (or an amino acid sequence that is suitable for use as an immunoglobulin single variable domain) may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH sequence); other single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-6), to Holt et al. 2003 (Trends Biotechnol.

21(11): 484-490); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

The amino acid sequence and structure of an immunoglobulin sequence, in particular an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in an immunoglobulin single variable domain can be in the region of 110-120, is preferably 112-115, and is most preferably 113. It should however be noted that parts, fragments, analogs or derivatives of an immunoglobulin single variable domain are not particularly limited as to their length and/or size, as long as such parts, fragments, analogs or derivatives meet the further requirements outlined herein and are also preferably suitable for the purposes described herein.

For a further description of VHH's and Nanobodies, reference is made to the review article by Muyldermans 2001 (Reviews in Molecular Biotechnology 74: 277-302); as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825 by Ablynx N.V., and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

Thus, in the meaning of the present invention, the term "immunoglobulin single variable domain" or "single variable domain" comprises polypeptides which are derived from a non-human source, preferably a camelid, preferably a camel heavy chain antibody. They may be humanized, as previously described. Moreover, the term comprises polypeptides derived from non-camelid sources, e.g. mouse or human, which have been "camelized", as previously described.

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences and humanized camelid immunoglobulin sequences, or camelized immunoglobulin single variable domains, e.g. camelized dAb as described by Ward et al (see for example WO 94/04678 and Davies and Riechmann 1994, Febs Lett. 339: 285 and 1996, Protein Engineering 9: 531).

Immunoglobulin single variable domains (and polypeptides comprising the same) that are directed against IL-6R have been described in WO 08/020079 and WO 2010/115998. Preferred immunoglobulin single variable domains for use in the polypeptides of the invention include the improved Nanobodies described in WO 2010/115998.

For example, preferred immunoglobulin single variable domains may essentially consists of 4 framework regions (FR1 to FR4, respectively) and 3 complementarity determining regions (CDR1 to CDR3, respectively), in which:

a) CDR1 is chosen from the group consisting of: SEQ ID NO's: 17-19;

b) CDR2 is chosen from the group consisting of: SEQ ID NO's: 21-28; and c) CDR3 is chosen from the group consisting of: SEQ ID NO's: 30-32.

More preferably, the immunoglobulin single variable domain used in the polypeptide of the invention essentially consists of 4 framework regions (FR1 to FR4, respectively) and 3 complementarity determining regions (CDR1 to CDR3, respectively), in which:

a) CDR1 is chosen from SEQ ID NO: 17;

b) CDR2 is chosen from SEQ ID NO: 21; and c) CDR3 is chosen from SEQ ID NO: 30.

Preferred immunoglobulin single variable domains for use in the polypeptide of the invention include PMP7F4, PMP7C4, PMP7D6, PMP7G7, PMP7G8, 20F6, 20A11, 20E10, 21A10 and 21D11 (SEQ ID NO's: 1-10), more particularly 20F6, 20A11, 20E10, 21A10 and 21D11 (SEQ ID NO's: 1, 6, and 8-10) of which 20A11 (SEQ ID NO: 1) is particularly preferred.

Polypeptide of the Invention

The immunoglobulin single variable domains for use in the method of the invention may form part of a protein or polypeptide (referred herein as "polypeptide of the invention"), which may comprise or essentially consist of one or more immunoglobulin single variable domains that specifically binds IL-6R and which may optionally further comprise one or more further amino acid sequences (all optionally linked via one or more suitable linkers). The term "immunoglobulin single variable domain" may also encompass such polypeptide of the invention. For example, and without limitation, the one or more immunoglobulin single variable domains may be used as a binding unit in such a protein or polypeptide, which may optionally contain one or more further amino acid sequences that can serve as a binding unit, so as to provide a monovalent, multivalent or multispecific polypeptide of the invention, respectively (for multivalent and multispecific polypeptides containing one or more VHH domains and their preparation, reference is also made to Conrath et al. 2001 (J. Biol. Chem. 276: 7346-7350), as well as to for example WO 96/34103, WO 99/23221 and WO 2010/115998).

The polypeptides of the invention may encompass constructs comprising two or more antigen binding units in the form of single variable domains, as outlined above. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific etc. constructs can be formed. For example, an immunoglobulin single variable domain according to the invention may comprise two or three immunoglobulin single variable domains directed against the same target (i.e. IL-6R), or one or two immunoglobulin single variable domains directed against target A (i.e. IL-6R), and one immunoglobulin single variable domain against target B. Such constructs and modifications thereof, which the skilled person can readily envisage, are all encompassed by the term immunoglobulin single variable domain as used herein.

In an aspect of the invention, the polypeptide of the invention that comprises or essentially consists of one or more immunoglobulin single variable domains (or suitable fragments thereof) that specifically bind IL-6R, may further comprise one or more other groups, residues, moieties or binding units. Such further groups, residues, moieties, binding units or amino acid sequences may or may not provide further functionality to the immunoglobulin single variable domain (and/or to the polypeptide in which it is present) and may or may not modify the properties of the immunoglobulin single variable domain.

For example, such further groups, residues, moieties or binding units may be one or more additional amino acid sequences, such that the compound, construct or polypeptide is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domain so as to provide a "derivative" of the immunoglobulin single variable domain.

In the polypeptides described above, the one or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

Suitable spacers or linkers for use in multivalent and/or multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each amino acid sequence or Nanobody by itself forms a complete antigen-binding site).

For example, a linker may be a suitable amino acid sequence, and in particular amino acid sequences of between 1 and 50, preferably between 1 and 30, such as between 1 and 20 or between 1 and 10 amino acid residues. Widely used peptide linkers comprise Gly-Ser repeats, e.g. (Gly)4-Ser in one, two, three, four, five, six or more repeats, or for example of the type $(gly_x ser_y)_z$, such as (for example $(gly_4 ser)_3$ or $(gly_3 ser_2)_3$, as described in WO 99/42077, or hinge-like regions such as the hinge regions of naturally occurring heavy chain antibodies or similar sequences (such as described in WO 94/04678). Some other particularly preferred linkers are poly-alanine (such as AAA), as well as the linkers mentioned in Table A-5, of which AAA, GS-7, GS-8 and GS-9 are particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

In one specific aspect of the invention, a polypeptide of the invention is prepared that has an increased half-life, compared to the corresponding immunoglobulin single variable domain. Examples of polypeptides of the invention that comprise such half-life extending moieties for example include, without limitation, polypeptides in which the immunoglobulin single variable domain is suitable linked to one or more serum proteins or fragments thereof (such as (human) serum albumin or suitable fragments thereof) or to one or more binding units or peptides that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrine); polypeptides in which the immunoglobulin single variable domain is linked to an Fc portion (such as a human Fc) or a suitable part or fragment thereof; or polypeptides in which the one or more immunoglobulin single variable domains are suitable linked to one or more small proteins or peptides that can bind to serum proteins (such as, without limitation, the proteins and peptides described in WO 91/01743, WO 01/45746, or WO 02/076489).

Generally, the polypeptides of the invention with increased half-life preferably have a half-life that is at least 1.5 times, preferably at least 2 times, such as at least 5 times, for example at least 10 times or more than 20 times, greater than the half-life of the corresponding immunoglobulin single variable domain or polypeptide of the invention per se.

A preferred polypeptide of the invention comprises one or more immunoglobulin single variable domains against IL-6R, e.g. according to SEQ ID NO's: 1-10, in particular SEQ ID NO: 1, in combination with at least one binding domain or peptide suitable for extending serum half-life (preferably T1/2β) of the construct. In these constructs, the "serum-albumin binding domain or peptide" may be any suitable serum-albumin binding peptide or binding domain capable of increasing the half-life (preferably T1/2β) of the construct (compared to the same construct without the serum-albumin binding peptide or binding domain). Specifically, the polypeptide sequence suitable for extending serum half-life is a polypeptide sequence capable of binding to a serum protein with a long serum half-life, such as serum albumin, transferring, IgG, etc., in particular serum albumin. Polypeptide sequences capable of binding to serum albumin have previously been described and may in particular be serum albumin binding peptides as described in WO 08/068280 by applicant (and in particular WO 09/127691 and WO 2011/095545, both by applicant), or a serum albumin binding immunoglobulin single variable domains (such as a serum-albumin binding Nanobody; for example Alb-1 or a humanized version of Alb-1 such as Alb-8, for which reference is for example made to WO 06/122787 and Table A-4).

As discussed above, in the polypeptides of the invention the one or more immunoglobulin single variable domain binding to IL-6R and the amino acid sequences or domains suitable for extending serum half-life can be fused with or without a linker, e.g. a peptide linker.

In a preferred polypeptide for use in the method of the invention one or more immunoglobulin single variable domains against IL-6R, e.g. according to SEQ ID NO's: 1-10, in particular SEQ ID NO: 1, is linked to a serum albumin binding immunoglobulin single variable domains, such as for example Alb-1 or a humanized version of Alb-1 such as Alb-8. Preferred polypeptides of the invention include IL6R304, IL6R305 and IL6R306 (SEQ ID NO's: 34-36), particularly IL6R304 (SEQ ID NO: 34).

The polypeptides of the invention administered in the methods of the invention, i.e., that specifically bind IL-6R, in some aspects have an apparent $K_D$ for binding to IL-6R, as determined by Biacore assay, of 1 nM to 1 pM (moles/litre) or less, preferably 500 pM to 1 pM (moles/litre) or less, more preferably 100 pM to 1 pM (moles/litre) or less, or even more preferably about 50 pM to 1 pM or less.

The polypeptides of the invention may be produced by a method comprising the following steps:
 a) expressing, in a suitable host cell or host organism or in another suitable expression system, a nucleic acid or nucleotide sequence, or a genetic construct encoding the polypeptide of the invention;
 optionally followed by:
 b) isolating and/or purifying the polypeptide of the invention thus obtained.

The method for producing the polypeptide of the invention may comprise the steps of:
 a) cultivating and/or maintaining a host or host cell under conditions that are such that said host or host cell expresses and/or produces at least one polypeptide of the invention,
 optionally followed by:
 b) isolating and/or purifying the polypeptide of the invention thus obtained.

According to one preferred, but non-limiting embodiment of the invention, the polypeptide of the invention is produced in a bacterial cell, in particular a bacterial cell suitable for large scale pharmaceutical production.

According to another preferred, but non-limiting embodiment of the invention, the polypeptide of the invention is produced in a yeast cell, in particular a yeast cell suitable for large scale pharmaceutical production.

According to yet another preferred, but non-limiting embodiment of the invention, the polypeptide of the invention is produced in a mammalian cell, in particular in a human cell or in a cell of a human cell line, and more in particular in a human cell or in a cell of a human cell line that is suitable for large scale pharmaceutical production.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

Subsequently, the polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds. Such a formulation may be in a form suitable for parenteral administration (such as by intravenous, intramuscular or subcutaneous injection or intravenous infusion).

Generally, the polypeptides of the invention can be formulated and administered in any suitable manner known per se, for which reference is for example made to the general background art cited above (and in particular to WO 04/041862, WO 04/041863, WO 04/041865 and WO 04/041867) as well as to the standard handbooks, such as Remington's Pharmaceutical Sciences, 18$^{th}$ Ed., Mack Publishing Company, USA (1990) or Remington, the Science and Practice of Pharmacy, 21th Edition, Lippincott Williams and Wilkins (2005).

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The invention, however, also encompasses products obtainable by further processing of a liquid formulation, such as a frozen, lyophilized or spray dried product. Upon reconstitution, these solid products can become liquid formulations as described herein (but are not limited thereto). In its broadest sense, therefore, the term "formulation" encompasses both liquid and solid formulations. However, solid formulations are understood as derivable from the liquid formulations (e.g. by freezing, freeze-drying or spray-drying), and hence have characteristics that are defined by the features specified for liquid formulations herein. The invention does not exclude reconstitution that leads to a composition that deviates from the original composition before e.g. freeze- or spray drying.

Sterile injectable solutions are prepared by incorporating the polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Generally, the concentration of the polypeptides of the invention in a liquid composition, such as an injectable or infusible preparation, or a lotion, will be from about 0.1-25 wt %, preferably from about 0.5-10 wt %, although the amounts are not limited to these ranges and may be higher or lower weight percentages depending on the need for higher or lower doses that can be administered in a volume that is suitable.

As demonstrated herein in the working examples, concentrations of 10 mg/mL have been used. It is expected that other concentrations having values between these concentrations (and also outside these values, i.e., higher or lower than these values) therefore also can be used. For example, concentrations of 0.5, 1, 2, 5, 10, 20, 25, 30, 40, 50, 60, 70, 80, 90, 100, 120, 150 mg/mL or more can be used.

To obtain the unexpected prolonged and sustained effects described herein, the polypeptide of the invention is administered in an amount from about 1 mg/kg to about 10 mg/kg. Exemplary dose ranges (inclusive of the values at the ends of each range) include 3-10 mg/kg, such as 3-9 mg/kg, 3-8 mg/kg, 3-7 mg/kg, 3-6 mg/kg, 3-5 mg/kg, 3-4 mg/kg, 4-10 mg/kg, 4-9 mg/kg, 4-8 mg/kg, 4-7 mg/kg, 4-6 mg/kg, 4-5 mg/kg, 5-10 mg/kg, 5-9 mg/kg, 5-8 mg/kg, 5-7 mg/kg, 5-6 mg/kg, 6-10 mg/kg, 6-9 mg/kg, 6-8 mg/kg, 6-7 mg/kg, 7-10 mg/kg, 7-9 mg/kg, 7-8 mg/kg, 8-10 mg/kg, 8-9 mg/kg, 9-10 mg/kg. A preferred dose range includes 3-6 mg/kg. Specific doses include doses of about 1, about 2, about 3, about 4, about 5, about 6, about 7, about 8, about 9 or about 10 mg/kg, in which 3 mg/kg and 6 mg/kg are preferred doses.

The desired dose may conveniently be presented in a single dose or as divided doses administered at appropriate intervals, for example, as weekly doses, e.g. 4 weekly doses (Q4W) or 8 weekly doses (Q8W).

In a preferred aspect, the polypeptide of the invention is administered in an amount from about 3 mg/kg to about 10 mg/kg as a single dose.

In another preferred aspect, the polypeptide of the invention is administered in an amount from about 3 mg/kg to about 10 mg/kg every 4 weeks.

In another preferred aspect, the polypeptide of the invention is administered in an amount from about 3 mg/kg to about 10 mg/kg every 8 weeks.

In another preferred aspect, the polypeptide of the invention is administered in an amount from about 3 mg/kg to about 6 mg/kg as a single dose.

In another preferred aspect, the polypeptide of the invention is administered in an amount from about 3 mg/kg to about 6 mg/kg every 4 weeks.

In another preferred aspect, the polypeptide of the invention is administered in an amount from about 3 mg/kg to about 6 mg/kg every 8 weeks.

In another preferred aspect, the polypeptide of the invention is administered at a dose of about 3 mg/kg as a single dose.

In another preferred aspect, the polypeptide of the invention is administered at a dose of about 3 mg/kg every 4 weeks.

In another preferred aspect, the polypeptide of the invention is administered at a dose of about 3 mg/kg every 8 weeks.

In another preferred aspect, the polypeptide of the invention is administered at a dose of about 6 mg/kg as a single dose.

In another preferred aspect, the polypeptide of the invention is administered at a dose of about 6 mg/kg every 4 weeks.

In another preferred aspect, the polypeptide of the invention is administered at a dose of about 6 mg/kg every 8 weeks.

The invention also provides methods for inhibiting IL-6 mediated signaling in a subject that include administering to the subject a polypeptide of the invention at lower doses to obtain equivalent effects in inhibiting IL-6 mediated signaling compared to the agents, compositions, methods and/or dosing schedules that are currently used and/or known in the art. Therefore, in another aspect of the method of the invention, the polypeptide of the invention is administered at a dose of about 1-2 mg/kg every 1-2 weeks, such as e. at a dose of about 2 mg/kg every 2 weeks or at a dose of about 1 mg/kg every week.

Methods are provided for inhibiting IL-6 mediated signaling in a subject that include administering to the subject a polypeptide of the invention in an amount from about 3 mg/kg to about 10 mg/kg, wherein total sIL-6R levels in serum are increased for at least 4 weeks after administration. In some embodiments, the serum level of sIL-6R is increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more. In a specific aspect, the levels of IL-6R are increased to and maintained at at least 400 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of sIL-6R are increased to and maintained at at least 450 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of sIL-6R are increased to and maintained at at least 500 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of sIL-6R are increased to and maintained at at least 550 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of sIL-6R are increased to and maintained at at least 600 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of sIL-6R are increased to and maintained at at least 650 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of sIL-6R are increased to and maintained at at least 700 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In a further aspect, methods are provided for inhibiting IL-6 mediated signaling in a subject that include administering to the subject a polypeptide of the invention in an amount from about 3 mg/kg to about 6 mg/kg, wherein total sIL-6R levels in serum are increased for at least 4 weeks after administration. In some embodiments, the serum level of sIL-6R is increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more. In a specific aspect, the levels of sIL-6R are increased to and maintained at at least 400 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of sIL-6R are increased to and maintained at at least 450 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of sIL-6R are increased to and maintained at at least 500 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of sIL-6R are increased to and maintained at at least 550 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of sIL-6R are increased to and maintained at at least 600 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of sIL-6R are increased to and maintained at at least 650 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of sIL-6R are increased to and maintained at at least 700 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In yet another aspect, methods are provided for inhibiting IL-6 mediated signaling in a subject that include administering to the subject a polypeptide of the invention in an amount of about 3 mg/kg, wherein total sIL-6R levels in serum are increased for at least 4 weeks after administration. In some embodiments, the serum level of sIL-6R is increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more. In a specific aspect, the levels of sIL-6R are increased to and maintained at at least 400 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of sIL-6R are increased to and maintained at at least 450 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of sIL-6R are increased to and maintained at at least 500 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of sIL-6R are increased to and maintained at at least 550 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of sIL-6R are increased to and maintained at at least 600 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of sIL-6R are increased to and maintained at at least 650 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of sIL-6R are increased to and maintained at at least 700 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In yet another aspect, methods are provided for inhibiting IL-6 mediated signaling in a subject that include administering to the subject a polypeptide of the invention in an amount of about 6 mg/kg, wherein total sIL-6R levels in serum are increased for at least 4 weeks after administration. In some embodiments, the serum level of sIL-6R is increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more. In a specific aspect, the levels of sIL-6R are increased to and maintained at at least 400 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of sIL-6R are increased to and maintained at at least 450 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of sIL-6R are increased to and maintained at at least 500 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of sIL-6R are increased to and maintained at at least 550 ng/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of sIL-6R are increased to and maintained at at least 600 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of sIL-6R are increased to and maintained at at least 650 ng/ml or more for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of sIL-6R are increased to and maintained at at least 700 ng/ml or more for up to at least 5 weeks, at least 6 weeks, at least 7 weeks, at least 8 weeks, at least 9 weeks, at least 10 weeks, at least 11 weeks, or even at least 12 weeks after administration.

A preferred dosage schedule includes 3 mg/kg of polypeptide of the invention every 4 weeks, wherein the levels of sIL-6R are increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more (during the treatment period).

Another preferred dosage schedule includes 6 mg/kg every 4 weeks, wherein the levels of sIL-6R are increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more (during the treatment period).

Another preferred dosage schedule includes 6 mg/kg every 8 weeks, wherein the levels of sIL-6R are increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more (during the treatment period).

In a preferred aspect, the polypeptide of the invention is SEQ ID NO: 34.

Accordingly, the present invention relates a method for inhibiting IL-6 mediated signaling in a subject, said method comprising administering to the subject a polypeptide with SEQ ID NO: 34 in an amount of about 3 mg/kg of SEQ ID NO: 34 every 4 weeks, wherein total sIL-6R levels in serum are increased to and maintained (throughout the treatment period) at at least 400 ng/ml. The invention thus also relates to a polypeptide with SEQ ID NO: 34 for inhibiting IL-6 mediated signaling, wherein the polypeptide is administered in an amount of 3 mg/kg of polypeptide with SEQ ID NO: 34 every 4 weeks and wherein total sIL-6R levels in serum are increased to and maintained (throughout the treatment period) at at least 400 ng/ml. The invention also relates to a polypeptide with SEQ ID NO: 34 for treatment of diseases and/or disorders associated with IL-6 mediated signaling, wherein the polypeptide is administered in an amount of 3 mg/kg of polypeptide with SEQ ID NO: 34 every 4 weeks and wherein total sIL-6R levels in serum are increased to and maintained (throughout the treatment period) at at least 400 ng/ml.

In a preferred aspect, the levels of sIL-6R are increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml, or more (during the treatment period).

The present invention also relates a method for inhibiting IL-6 mediated signaling in a subject, said method comprising administering to the subject a polypeptide with SEQ ID NO: 34 in an amount of about 6 mg/kg of SEQ ID NO: 34 every 4 weeks, wherein total sIL-6R levels in serum are increased to and maintained (throughout the treatment period) at at least 400 ng/ml. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 4 weeks and wherein total sIL-6R levels in serum are increased to and maintained (throughout the treatment period) at at least 400 ng/ml. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 4 weeks and wherein total sIL-6R levels in serum are increased to and maintained (throughout the treatment period) at at least 400 ng/ml.

In a preferred aspect, the levels of sIL-6R are increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml, or more (during the treatment period).

In a preferred aspect, a polypeptide with SEQ ID NO: 34 is administered in an amount of about 100 nmol/kg to about 150 nmol/kg of SEQ ID NO: 34 every 4 weeks and total sIL-6R levels in serum are increased to and maintained (throughout the treatment period) at at least 500 ng/ml.

In another preferred aspect, a polypeptide with SEQ ID NO: 34 is administered in an amount of about 100 nmol/kg to about 150 nmol/kg of SEQ ID NO: 34 every 4 weeks and total sIL-6R levels in serum are increased to and maintained (throughout the treatment period) at at least 550 ng/ml.

In yet another preferred aspect, a polypeptide with SEQ ID NO: 34 is administered in an amount of about 100 nmol/kg to about 150 nmol/kg of SEQ ID NO: 34 every 4 weeks and total sIL-6R levels in serum are increased to and maintained (throughout the treatment period) at at least 600 ng/ml.

In yet another preferred aspect, a polypeptide with SEQ ID NO: 34 is administered in an amount of about 100 nmol/kg to about 120 nmol/kg of SEQ ID NO: 34 every 4 weeks and total sIL-6R levels in serum are increased to and maintained (throughout the treatment period) at at least 500 ng/ml.

In yet another preferred aspect, a polypeptide with SEQ ID NO: 34 is administered in an amount of about 100 nmol/kg to about 120 nmol/kg of SEQ ID NO: 34 every 4 weeks and total sIL-6R levels in serum are increased to and maintained (throughout the treatment period) at at least 550 ng/ml.

In yet another preferred aspect, a polypeptide with SEQ ID NO: 34 is administered in an amount of about 100 nmol/kg to about 120 nmol/kg of SEQ ID NO: 34 every 4 weeks and total sIL-6R levels in serum are increased to and maintained (throughout the treatment period) at at least 600 ng/ml.

The present invention also relates a method for inhibiting IL-6 mediated signaling in a subject, said method comprising administering to the subject a polypeptide with SEQ ID NO: 34 in an amount of about 6 mg/kg of SEQ ID NO: 34 every 8 weeks, wherein total sIL-6R levels in serum are increased to and maintained (throughout the treatment period) at at least 400 ng/ml. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 8 weeks and wherein total sIL-6R levels in serum are increased to and maintained (throughout the treatment period) at at least 400 ng/ml. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 8 weeks and wherein total sIL-6R levels in serum are increased to and maintained (throughout the treatment period) at at least 400 ng/ml.

In a preferred aspect, the levels of sIL-6R are increased to and maintained at at least 400 ng/ml or more, such as at least 450 ng/ml, at least 500 ng/ml, more preferably at least 550 ng/ml, at least 600 ng/ml, at least 650 ng/ml, or even at least 700 ng/ml or more (during the treatment period).

Methods are provided for inhibiting IL-6 mediated signaling in a subject that include administering to the subject a polypeptide of the invention in an amount from about 3 mg/kg to about 10 mg/kg, wherein total IL-6 levels in serum are increased for at least 4 weeks after administration. In some embodiments, the serum level of IL-6 are increased to and maintained at at least 40 pg/ml or more, such as at least 45 pg/ml, at least 50 pg/ml, more preferably at least 55 pg/ml or even at least 60 pg/ml or more. In a specific aspect, the levels of IL-6 are increased to and maintained at at least 40 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of IL-6 are increased to and maintained at at least 45 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of IL-6 are increased to and maintained at at least 50 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of IL-6 are increased to and maintained at at least 55 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of IL-6 are increased to and maintained at at least 60 pg/ml or more for up to at least 5 weeks, at least 6 weeks, at least 7 weeks, at least 8 weeks, at least 9 weeks, at least 10 weeks, at least 11 weeks, or even at least 12 weeks after administration.

In a further aspect, methods are provided for inhibiting IL-6 mediated signaling in a subject that include administering to the subject a polypeptide of the invention in an amount from about 3 mg/kg to about 6 mg/kg, wherein total IL-6 levels in serum are increased for at least 4 weeks after administration. In some embodiments, the serum level of IL-6 is increased to and maintained at at least 40 pg/ml or more, such as at least 45 pg/ml, at least 50 pg/ml, more preferably at least 55 pg/ml or even at least 60 pg/ml or more. In a specific aspect, the levels of IL-6 are increased to and maintained at at least 40 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of IL-6 are increased to and maintained at at least 45 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of IL-6 are increased to and maintained at at least 50 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of IL-6 are increased to and maintained at at least 55 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of IL-6 are increased to and maintained at at least 60 pg/ml or more for up to at least 5 weeks, at least 6 weeks, at least 7 weeks, at least 8 weeks, at least 9 weeks, at least 10 weeks, at least 11 weeks, or even at least 12 weeks after administration.

In yet another aspect, methods are provided for inhibiting IL-6 mediated signaling in a subject that include administering to the subject a polypeptide of the invention in an amount of about 3 mg/kg, wherein total IL-6 levels in serum are increased for at least 4 weeks after administration. In some embodiments, the serum level of IL-6 is increased to and maintained at at least 40 pg/ml or more, such as at least 45 pg/ml, at least 50 pg/ml, more preferably at least 55 pg/ml or even at least 60 pg/ml or more. In a specific aspect, the levels of IL-6 are increased to and maintained at at least 40 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of IL-6 are increased to and maintained at at least 45 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of IL-6 are increased to and maintained at at least 50 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of IL-6 are increased to and maintained at at least 55 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of IL-6 are increased to and maintained at at least 60 pg/ml or more for up to at least 5 weeks, at least 6 weeks, at least 7 weeks, at least 8 weeks, at least 9 weeks, at least 10 weeks, at least 11 weeks, or even at least 12 weeks after administration.

In yet another aspect, methods are provided for inhibiting IL-6 mediated signaling in a subject that include administering to the subject a polypeptide of the invention in an amount of about 6 mg/kg, wherein total IL-6 levels in serum are increased for at least 4 weeks after administration. In some embodiments, the serum level of IL-6 is increased to and maintained at at least 40 pg/ml or more, such as at least 45 pg/ml, at least 50 pg/ml, more preferably at least 55 pg/ml or even at least 60 pg/ml or more. In a specific aspect, the levels of IL-6 are increased to and maintained at at least 40 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of IL-6 are increased to and maintained at at least 45 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of IL-6 are increased to and maintained at at least 50 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of IL-6 are increased to and maintained at at least 55 pg/ml for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of IL-6 are increased to and maintained at at least 60 pg/ml or more for up to at least 5 weeks, at least 6 weeks, at least 7 weeks, at least 8 weeks, at least 9 weeks, at least 10 weeks, at least 11 weeks, or even at least 12 weeks after administration.

A preferred dosage schedule includes 3 mg/kg of polypeptide of the invention every 4 weeks, wherein the levels of IL-6 are increased to and maintained at at least 40 pg/ml or more, such as at least 45 pg/ml, at least 50 pg/ml, more preferably at least 55 pg/ml or even at least 60 pg/ml or more (during the treatment period).

Another preferred dosage schedule includes 6 mg/kg of polypeptide of the invention every 4 weeks, wherein the levels of IL-6 are increased to and maintained at at least 40 pg/ml or more, such as at least 45 pg/ml, at least 50 pg/ml, more preferably at least 55 pg/ml or even at least 60 pg/ml or more (during the treatment period).

Another preferred dosage schedule includes 6 mg/kg of polypeptide of the invention every 8 weeks, wherein the levels of IL-6 are increased to and maintained at at least 40 pg/ml or more, such as at least 45 pg/ml, at least 50 pg/ml, more preferably at least 55 pg/ml or even at least 60 pg/ml or more (during the treatment period).

In a preferred aspect, the polypeptide of the invention is SEQ ID NO: 34.

Accordingly, the invention relates to a method for inhibiting IL-6 mediated signaling in a subject, said method comprising administering to the subject a polypeptide with SEQ ID NO: 34 in an amount of 3 mg/kg of polypeptide with SEQ ID NO: 34 every 4 weeks, wherein total sIL-6R levels in serum are increased to and maintained (throughout the treatment period) at at least 40 pg/ml. The invention thus also relates to a polypeptide with SEQ ID NO: 34 for inhibiting IL-6 mediated signaling, wherein the polypeptide is administered in an amount of 3 mg/kg of polypeptide with SEQ ID NO: 34 every 4 weeks and wherein total sIL-6R levels in serum are increased to and maintained (throughout the treatment period) at at least 40 pg/ml. The invention also relates to a polypeptide with SEQ ID NO: 34 for treatment of diseases and/or disorders associated with IL-6 mediated signaling, wherein the polypeptide is administered in an amount of 3 mg/kg of polypeptide with SEQ ID NO: 34 every 4 weeks and wherein total sIL-6R levels in serum are increased to and maintained (throughout the treatment period) at at least 40 pg/ml.

In a preferred aspect the levels of IL-6 are increased to and maintained at at least 40 pg/ml or more, such as at least 45 pg/ml, at least 50 pg/ml, more preferably at least 55 pg/ml or even at least 60 pg/ml or more (during the treatment period).

The invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 4 weeks, wherein total sIL-6R levels in serum are increased to and maintained (throughout the treatment period) at at least 40 pg/ml. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 4 weeks and wherein total sIL-6R levels in serum are increased to and maintained (throughout the treatment period) at at least 40 pg/ml. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 4 weeks and wherein total sIL-6R levels in serum are increased to and maintained (throughout the treatment period) at at least 40 pg/ml.

In a preferred aspect the levels of IL-6 are increased to and maintained at at least 40 pg/ml or more, such as at least 45 pg/ml, at least 50 pg/ml, more preferably at least 55 pg/ml or even at least 60 pg/ml or more (during the treatment period).

The invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 8 weeks, wherein total sIL-6R levels in serum are increased to and maintained (throughout the treatment period) at at least 40 pg/ml. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 8 weeks and wherein total sIL-6R levels in serum are increased to and maintained (throughout the treatment period) at at least 40 pg/ml. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 8 weeks and wherein total sIL-6R levels in serum are increased to and maintained (throughout the treatment period) at at least 40 pg/ml.

In a preferred aspect the levels of IL-6 are increased to and maintained at at least 40 pg/ml or more, such as at least 45 pg/ml, at least 50 pg/ml, more preferably at least 55 pg/ml or even at least 60 pg/ml or more (during the treatment period).

Methods are provided for inhibiting IL-6 mediated signaling in a subject that include administering to the subject a polypeptide of the invention in an amount from about 3 mg/kg to about 10 mg/kg, wherein CRP levels in serum are decreased for at least 4 weeks after administration. In some embodiments, the serum level of CRP is decreased to and maintained below 10 mg/l or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less. In a specific aspect, the levels of CRP are decreased to and maintained below 10 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 9 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 8 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 7.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 7 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 6.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 6 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 5.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased to and maintained below 5 mg/l or less for up to at least 5 weeks, at least 6 weeks, at least 7 weeks, at least 8 weeks, at least 9 weeks, at least 10 weeks, at least 11 weeks, or even at least 12 weeks after administration. In a further aspect, methods are provided for inhibiting IL-6 mediated signaling in a subject that include administering to the subject a polypeptide of the invention in an amount from about 3 mg/kg to about 6 mg/kg, wherein CRP levels in serum are decreased for at least 4 weeks after administration. In some embodiments, the serum level of CRP is decreased to and maintained below 10 mg/l or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less. In a specific aspect, the levels of CRP are decreased to and maintained below 10 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 9 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 8 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 7.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 7 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 6.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 6 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 5.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased to and maintained below 5 mg/l or less for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 3 mg/kg, wherein CRP levels in serum are decreased for at least 4 weeks after administration. In some embodiments, the serum level of CRP is decreased to and maintained below 10 mg/l or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less. In a specific aspect, the levels of CRP are decreased to and maintained below 10 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 9 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 8 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 7.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 7 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 6.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 6 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 5.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased to and maintained below 5 mg/l or less for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 6 mg/kg, wherein CRP levels in serum are decreased for at least 4 weeks after administration. In some embodiments, the serum level of CRP is decreased to and maintained below 10 mg/l or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less. In a specific aspect, the levels of CRP are decreased to and maintained below 10 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased to and maintained below 9 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in in an amount of about 6 mg/kg, wherein the levels of CRP are decreased to and maintained below 8 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased to and maintained below 7.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased to and maintained below 7 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased to and maintained below 6.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased to and maintained below 6 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased to and maintained below 5.5 mg/l for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased to and maintained below 5 mg/l or less for up to at least 5 weeks, at least 6 weeks, at least 7 weeks, at least 8 weeks, at least 9 weeks, at least 10 weeks, at least 11 weeks, or even at least 12 weeks after administration.

A preferred dosage schedule includes 3 mg/kg of polypeptide of the invention every 4 weeks, wherein the levels of CRP are decreased to and maintained below 10 mg/ml or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less (during the treatment period).

Another preferred dosage schedule includes 6 mg/kg of polypeptide of the invention every 4 weeks, wherein the levels of CRP are decreased to and maintained below 10 mg/ml or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less (during the treatment period).

Another preferred dosage schedule includes 6 mg/kg of polypeptide of the invention every 8 weeks, wherein the levels of CRP are decreased to and maintained below 10 mg/ml or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less (during the treatment period).

In a preferred aspect, the polypeptide of the invention is SEQ ID NO: 34.

Accordingly, the present invention relates to a method for inhibiting IL-6 mediated signaling in a subject, said method comprising administering to the subject a polypeptide with SEQ ID NO: 34 in an amount of 3 mg/kg of polypeptide with SEQ ID NO: 34 every 4 weeks, wherein CRP levels in serum are decreased and maintained below 10 mg/l. The invention thus also relates to a polypeptide with SEQ ID NO: 34 for inhibiting IL-6 mediated signaling, wherein the polypeptide is administered in an amount of 3 mg/kg of polypeptide with SEQ ID NO: 34 every 4 weeks and wherein CRP levels in serum are decreased to and maintained below 10 mg/l. The invention also relates to a polypeptide with SEQ ID NO: 34 for treatment of diseases and/or disorders associated with IL-6 mediated signaling, wherein the polypeptide is administered in an amount of 3 mg/kg of polypeptide with SEQ ID NO: 34 every 4 weeks and wherein CRP levels in serum are decreased to and maintained below 10 mg/l.

In a preferred aspect, the levels of CRP are decreased to and maintained below 10 mg/ml or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less (during the treatment period).

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 4 weeks, wherein CRP levels in serum are decreased to and maintained below 10 mg/l. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 4 weeks and wherein CRP levels in serum are decreased to and maintained below 10 mg/l. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 4 weeks and wherein CRP levels in serum are decreased to and maintained below 10 mg/l.

In a preferred aspect, the levels of CRP are decreased to and maintained below 10 mg/ml or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less (during the treatment period).

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 8 weeks, wherein CRP levels in serum are decreased to and maintained below 10 mg/l. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 8 weeks and wherein CRP levels in serum are decreased to and maintained below 10 mg/l. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 8 weeks and wherein CRP levels in serum are decreased to and maintained below 10 mg/l.

In a preferred aspect, the levels of CRP are decreased to and maintained below 10 mg/ml or less, such as below 9 mg/l or below 8 mg/l, more preferably below 7.5 mg/l, below 7 mg/l or below 6.5 mg/l, or even below 6 mg/l, below 5.5 mg/l, below 5 mg/l, or less (during the treatment period).

In a specific aspect, when the subject is also receiving methotrexate (MTX) therapy, the baseline CRP levels (i.e. the CRP levels before dosing the polypeptide of the invention) in serum are most likely already below 10 mg/ml or less (unrelated to the anti-IL-6R therapy). Accordingly, "reduction of CRP levels in serum below 10 mg/l or less and maintenance of CRP levels in serum below 10 mg/l or less" cannot be used as a relevant marker for the pharmacodynamic effect of the polypeptide of the invention in subjects that also receive MTX therapy, but only in subjects that do not receive methotrexate (MTX) therapy.

Methods are provided for inhibiting IL-6 mediated signaling in a subject that include administering to the subject a polypeptide of the invention in an amount from about 3 mg/kg to about 10 mg/kg, wherein CRP levels in serum are decreased for at least 4 weeks after administration. In some embodiments, the serum level of CRP is decreased by and maintained at 30% or more, 40% or more, 50% or more, 60% or more, or even 70% or more (reduction) compared to baseline (i.e. pre-treatment or normal) levels. In a specific aspect, the levels of CRP are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of CRP are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In a further aspect, methods are provided for inhibiting IL-6 mediated signaling in a subject that include administering to the subject a polypeptide of the invention in an amount from about 3 mg/kg to about 6 mg/kg, wherein CRP levels in serum are decreased for at least 4 weeks after administration. In some embodiments, the serum level of CRP is decreased by and maintained at 30% or more, 40% or more, 50% or more, 60% or more, or even 70% or more (reduction) compared to baseline (i.e. pre-treatment or normal) levels. In a specific aspect, the levels of CRP are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased by and maintained at 60% or more (reduction) compared to baseline (i.e. pre-treatment or normal) levels up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of CRP are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 3 mg/kg, wherein CRP levels in serum are decreased for at least 4 weeks after administration. In some embodiments, the serum level of CRP is decreased by and maintained at 30% or more, 40% or more, 50% or more, 60% or more, or even 70% or more (reduction) compared to baseline (i.e. pre-treatment or normal) levels. In a specific aspect, the levels of CRP are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of CRP are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 6 mg/kg, wherein CRP levels in serum are decreased for at least 4 weeks after administration. In some embodiments, the serum level of CRP is decreased by and maintained at 30% or more, 40% or more, 50% or more, 60% or more, or even 70% or more (reduction) compared to baseline (i.e. pre-treatment or normal) levels. In a specific aspect, the levels of CRP are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of CRP are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

A preferred dosage schedule includes 3 mg/kg of polypeptide of the invention every 4 weeks, wherein the levels of CRP are decreased by and maintained at 30% or more, 40% or more, 50% or more, 60% or more, or even 70% or more (reduction) compared to baseline (i.e. pre-treatment or normal) levels.

Another preferred dosage schedule includes 6 mg/kg of polypeptide of the invention every 4 weeks, wherein the levels of CRP are decreased by and maintained at 30% or more, 40% or more, 50% or more, 60% or more, or even 70% or more (reduction) compared to baseline (i.e. pre-treatment or normal) levels.

Another preferred dosage schedule includes 6 mg/kg of polypeptide of the invention every 8 weeks, wherein the levels of CRP are decreased by and maintained at 30% or more, 40% or more, 50% or more, 60% or more, or even 70% or more (reduction) compared to baseline (i.e. pre-treatment or normal) levels.

In a preferred aspect, the polypeptide of the invention is SEQ ID NO: 34.

Accordingly, the present invention relates to a method for inhibiting IL-6 mediated signaling in a subject, said method comprising administering to the subject a polypeptide with SEQ ID NO: 34 in an amount of 3 mg/kg of polypeptide with SEQ ID NO: 34 every 4 weeks, wherein CRP levels in serum are decreased by and maintained at 50% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 3 mg/kg of polypeptide with SEQ ID NO: 34 every 4 weeks and wherein CRP levels in serum are decreased by and maintained at 50% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 3 mg/kg of polypeptide with SEQ ID NO: 34 every 4 weeks and wherein CRP levels in serum are decreased by and maintained at 50% or more (reduction) compared to baseline (i.e. pre-treatment or normal) levels.

In a preferred aspect, the levels of CRP are decreased by and maintained at 30% or more, 40% or more, 50% or more, 60% or more, or even 70% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 4 weeks, wherein CRP levels in serum are decreased by and maintained at 50% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 4 weeks and wherein CRP levels in serum are decreased by and maintained at 50% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 4 weeks and wherein CRP levels in serum are decreased by and maintained at 50% or more (reduction) compared to baseline (i.e. pre-treatment or normal) levels.

In a preferred aspect, the levels of CRP are decreased by and maintained at 30% or more, 40% or more, 50% or more, 60% or more, or even 70% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 8 weeks, wherein CRP levels in serum are decreased by and maintained at 50% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 8 weeks and wherein CRP levels in serum are decreased by and maintained at 50% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 8 weeks and wherein CRP levels in serum are decreased by and maintained at 50% or more (reduction) compared to baseline (i.e. pre-treatment or normal) levels.

In a preferred aspect, the levels of CRP are decreased by and maintained at 30% or more, 40% or more, 50% or more, 60% or more, or even 70% or more (reduction) compared to baseline (i.e. pre-treatment or normal) levels.

Methods are provided for inhibiting IL-6 mediated signaling in a subject that include administering to the subject a polypeptide of the invention in an amount from about 3 mg/kg to about 10 mg/kg, wherein ESR levels in serum are decreased for at least 4 weeks after administration. In some embodiments, the serum level of ESR is decreased by and maintained at 30% or more, 40% or more, 50% or more, 60% or more, or even 70% or more (reduction) compared to baseline (i.e. pre-treatment or normal) levels. In a specific aspect, the levels of ESR are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of ESR are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of ESR are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of ESR are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of ESR are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In a further aspect, methods are provided for inhibiting IL-6 mediated signaling in a subject that include administering to the subject a polypeptide of the invention in an amount from about 3 mg/kg to about 6 mg/kg, wherein ESR levels in serum are decreased for at least 4 weeks after administration. In some embodiments, the serum level of ESR is decreased by and maintained at 30% or more, 40% or more, 50% or more, 60% or more, or even 70% or more (reduction) compared to baseline (i.e. pre-treatment or normal) levels. In a specific aspect, the levels of ESR are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of ESR are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of ESR are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of ESR are decreased by and maintained at 60% or more (reduction) compared to baseline (i.e. pre-treatment or normal) levels up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of ESR are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 3 mg/kg, wherein ESR levels in serum are decreased for at least 4 weeks after administration. In some embodiments, the serum level of ESR is decreased by and maintained at 30% or more, 40% or more, 50% or more, 60% or more, 70% or more (reduction) compared to baseline (i.e. pre-treatment or normal) levels. In a specific aspect, the levels of ESR are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of ESR are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of ESR are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of ESR are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of ESR are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 6 mg/kg, wherein ESR levels in serum are decreased for at least 4 weeks after administration. In some embodiments, the serum level of ESR is decreased by and maintained at 30% or more, 40% or more, 50% or more, 60% or more, or even 70% or more (reduction) compared to baseline (i.e. pre-treatment or normal) levels. In a specific aspect, the levels of ESR are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of ESR are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of ESR are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of ESR are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of ESR are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

A preferred dosage schedule includes 3 mg/kg of polypeptide of the invention every 4 weeks, wherein the levels of ESR are decreased and maintained at 30% or more, 40% or more, 50% or more, 60% or more, or even 70% or more (reduction) compared to baseline (i.e. pre-treatment or normal) levels.

Another preferred dosage schedule includes 6 mg/kg of polypeptide of the invention every 4 weeks, wherein the levels of ESR are decreased by and maintained at 30% or more, 40% or more, 50% or more, 60% or more, or even 70% or more (reduction) compared to baseline (i.e. pre-treatment or normal) levels.

Another preferred dosage schedule includes 6 mg/kg of polypeptide of the invention every 8 weeks, wherein the levels of ESR are decreased by and maintained at 30% or more, 40% or more, 50% or more, 60% or more, or even 70% or more (reduction) compared to baseline (i.e. pre-treatment or normal) levels.

In a preferred aspect, the polypeptide of the invention is SEQ ID NO: 34.

Accordingly, the present invention relates to a method for inhibiting IL-6 mediated signaling in a subject, said method comprising administering to the subject a polypeptide with SEQ ID NO: 34 in an amount of 3 mg/kg of polypeptide with SEQ ID NO: 34 every 4 weeks, wherein ESR levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 3 mg/kg of polypeptide with SEQ ID NO: 34 every 4 weeks and wherein ESR levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 3 mg/kg of polypeptide with SEQ ID NO: 34 every 4 weeks and wherein ESR levels in serum are decreased by and maintained at 30% or more (reduction) compared to baseline (i.e. pre-treatment or normal) levels.

In a preferred aspect, the levels of ESR are decreased by and maintained at 30% or more, 40% or more, 50% or more, 60% or more, or even 70% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 4 weeks, wherein ESR levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 4 weeks and wherein ESR levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 4 weeks and wherein ESR levels in serum are decreased by and maintained at 30% or more (reduction) compared to baseline (i.e. pre-treatment or normal) levels.

In a preferred aspect, the levels of ESR are decreased by and maintained at 30% or more, 40% or more, 50% or more, 60% or more, or even 70% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 8 weeks, wherein ESR levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 8 weeks and wherein ESR levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 8 weeks and wherein ESR levels in serum are decreased by and maintained at 30% or more (reduction) compared to baseline (i.e. pre-treatment or normal) levels.

In a preferred aspect, the levels of ESR are decreased by and maintained at 30% or more, 40% or more, 50% or more, 60% or more, or even 70% or more (reduction) compared to baseline (i.e. pre-treatment or normal) levels.

Methods are provided for inhibiting IL-6 mediated signaling in a subject that include administering to the subject a polypeptide of the invention in an amount from about 3 mg/kg to about 10 mg/kg, wherein fibrinogen levels in serum are decreased for at least 4 weeks after administration. In some embodiments, the serum level of fibrinogen is decreased by and maintained at 20% or more, 30% or more, 40% or more, or even 50% or more (reduction) compared to baseline (i.e. pre-treatment or normal) levels. In a specific aspect, the levels of fibrinogen are decreased by and maintained at 20% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of fibrinogen are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of fibrinogen are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the levels of fibrinogen are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In a further aspect, methods are provided for inhibiting IL-6 mediated signaling in a subject that include administering to the subject a polypeptide of the invention in an amount from about 3 mg/kg to about 6 mg/kg, wherein fibrinogen levels in serum are decreased for at least 4 weeks after administration. In some embodiments, the serum level of fibrinogen is decreased by and maintained at 20% or more, 30% or more, 40% or more, or even 50% or more (reduction) compared to baseline (i.e. pre-treatment or normal) levels. In a specific aspect, the levels of fibrinogen are decreased by and maintained at 20% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of fibrinogen are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of fibrinogen are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the levels of fibrinogen are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 3 mg/kg, wherein fibrinogen levels in serum are decreased for at least 4 weeks after administration. In some embodiments, the serum level of fibrinogen is decreased by and maintained at 20% or more, 30% or more, 40% or more, or even 50% or more (reduction) compared to baseline (i.e. pre-treatment or normal) levels. In a specific aspect, the levels of fibrinogen are decreased by and maintained at 20% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In a specific aspect, a polypeptide of the invention is administered in an amount of about 3 mg/kg, wherein the levels of fibrinogen are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of fibrinogen are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the levels of fibrinogen are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 6 mg/kg, wherein fibrinogen levels in serum are decreased for at least 4 weeks after administration. In some embodiments, the serum level of fibrinogen is decreased by and maintained at 20% or more, 30% or more, 40% or more, or even 50% or more (reduction) compared to baseline (i.e. pre-treatment or normal) levels. In a specific aspect, the levels of fibrinogen are decreased by and maintained at 20% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of fibrinogen are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of fibrinogen are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of fibrinogen are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the levels of fibrinogen are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

A preferred dosage schedule includes 3 mg/kg of polypeptide of the invention every 4 weeks, wherein the levels of fibrinogen are decreased by and maintained at 20% or more, 30% or more, 40% or more, or even 50% or more (reduction) compared to baseline (i.e. pre-treatment or normal) levels.

Another preferred dosage schedule includes 6 mg/kg of polypeptide of the invention every 4 weeks, wherein the levels of fibrinogen are decreased by and maintained at 20% or more, 30% or more, 40% or more, or even 50% or more (reduction) compared to baseline (i.e. pre-treatment or normal) levels.

Another preferred dosage schedule includes 6 mg/kg of polypeptide of the invention every 8 weeks, wherein the levels of fibrinogen are decreased by and maintained at 20% or more, 30% or more, 40% or more, or even 50% or more (reduction) compared to baseline (i.e. pre-treatment or normal) levels.

In a preferred aspect, the polypeptide of the invention is SEQ ID NO: 34.

Accordingly, the present invention relates to a method for inhibiting IL-6 mediated signaling in a subject, said method comprising administering to the subject a polypeptide with SEQ ID NO: 34 in an amount of 3 mg/kg of polypeptide with SEQ ID NO: 34 every 4 weeks, wherein fibrinogen levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 3 mg/kg of polypeptide with SEQ ID NO: 34 every 4 weeks and wherein fibrinogen levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 3 mg/kg of polypeptide with SEQ ID NO: 34 every 4 weeks and wherein fibrinogen levels in serum are decreased by and maintained at 30% or more (reduction) compared to baseline (i.e. pre-treatment or normal) levels.

In a preferred aspect, the levels of fibrinogen are decreased by and maintained at 20% or more, 30% or more, 40% or more, or even 50% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 4 weeks, wherein fibrinogen levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 4 weeks and wherein fibrinogen levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 4 weeks and wherein fibrinogen levels in serum are decreased by and maintained at 30% or more (reduction) compared to baseline (i.e. pre-treatment or normal) levels.

In a preferred aspect, the levels of fibrinogen are decreased by and maintained at 20% or more, 30% or more, 40% or more, or even 50% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 8 weeks, wherein fibrinogen levels in serum are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 8 weeks and wherein fibrinogen levels in serum are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 8 weeks and wherein fibrinogen levels in serum are decreased by and maintained at 30% or more (reduction) compared to baseline (i.e. pre-treatment or normal) levels.

In a preferred aspect, the levels of fibrinogen are decreased by and maintained at 20% or more, 30% or more, 40% or more, or even 50% or more (reduction) compared to baseline (i.e. pre-treatment or normal) levels.

Methods are provided for inhibiting IL-6 mediated signaling in a subject that include administering to the subject a polypeptide of the invention in an amount from about 3 mg/kg to about 10 mg/kg, wherein serum amyloid A levels are decreased for at least 4 weeks after administration. In some embodiments, the serum amyloid A level is decreased by and maintained at 30% or more, 40% or more, 50% or more, 60% or more, or even 70% or more (reduction) compared to baseline (i.e. pre-treatment or normal) levels. In a specific aspect, the serum amyloid A levels are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the serum amyloid A levels are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the serum amyloid A levels are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the serum amyloid A levels are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 10 mg/kg, wherein the serum amyloid A levels are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In a further aspect, methods are provided for inhibiting IL-6 mediated signaling in a subject that include administering to the subject a polypeptide of the invention in an amount from about 3 mg/kg to about 6 mg/kg, wherein serum amyloid A levels are decreased for at least 4 weeks after administration. In some embodiments, the serum amyloid A level is decreased by and maintained at 30% or more, 40% or more, 50% or more, 60% or more, or even 70% or more (reduction) compared to baseline (i.e. pre-treatment or normal) levels. In a specific aspect, the serum amyloid A levels are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the serum amyloid A levels are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the serum amyloid A levels are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the serum amyloid A levels are decreased by and maintained at 60% or more (reduction) compared to baseline (i.e. pre-treatment or normal) levels up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount from about 3 mg/kg to about 6 mg/kg, wherein the serum amyloid A levels are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 3 mg/kg, wherein serum amyloid A levels are decreased for at least 4 weeks after administration. In some embodiments, the serum amyloid A level is decreased by and maintained at 30% or more, 40% or more, 50% or more, 60% or more, or even 70% or more (reduction) compared to baseline (i.e. pre-treatment or normal) levels. In a specific aspect, the serum amyloid A levels are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the serum amyloid A levels are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the serum amyloid A levels are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the serum amyloid A levels are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 3 mg/kg, wherein the serum amyloid A levels are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

Methods are provided for inhibiting IL-6 mediated signaling in a subject that include administering to the subject a polypeptide of the invention in an amount of about 6 mg/kg, wherein serum amyloid A levels are decreased for at least 4 weeks after administration. In some embodiments, the serum amyloid A level is decreased by and maintained at 30% or more, 40% or more, 50% or more, 60% or more, or even 70% or more (reduction) compared to baseline (i.e. pre-treatment or normal) levels. In a specific aspect, the serum amyloid A levels are decreased by and maintained at 30% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the serum amyloid A levels are decreased by and maintained at 40% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the serum amyloid A levels are decreased by and maintained at 50% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the serum amyloid A levels are decreased by and maintained at 60% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

In another specific aspect, a polypeptide of the invention is administered in an amount of about 6 mg/kg, wherein the serum amyloid A levels are decreased by and maintained at 70% or more (reduction) compared to baseline (i.e. pre-treatment or normal) levels for up to at least 5 weeks, at least 6 weeks, at least 7 weeks, at least 8 weeks, at least 9 weeks, at least 10 weeks, at least 11 weeks, or even at least 12 weeks after administration.

A preferred dosage schedule includes 3 mg/kg of polypeptide of the invention every 4 weeks, wherein the serum amyloid A levels are decreased by and maintained at 30% or more, 40% or more, 50% or more, 60% or more, or even 70% or more (reduction) compared to baseline (i.e. pre-treatment or normal) levels.

Another preferred dosage schedule includes 6 mg/kg of polypeptide of the invention every 4 weeks, wherein the serum amyloid A levels are decreased by and maintained at 30% or more, 40% or more, 50% or more, 60% or more, or even 70% or more (reduction) compared to baseline (i.e. pre-treatment or normal) levels.

Another preferred dosage schedule includes 6 mg/kg of polypeptide of the invention every 8 weeks, wherein the serum amyloid A levels are decreased by and maintained at 30% or more, 40% or more, 50% or more, 60% or more, or even 70% or more (reduction) compared to baseline (i.e. pre-treatment or normal) levels.

In a preferred aspect, the polypeptide of the invention is SEQ ID NO: 34.

Accordingly, the present invention relates to a method for inhibiting IL-6 mediated signaling in a subject, said method comprising administering to the subject a polypeptide with SEQ ID NO: 34 in an amount of 3 mg/kg of polypeptide with SEQ ID NO: 34 every 4 weeks, wherein serum amyloid A levels are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 3 mg/kg of polypeptide with SEQ ID NO: 34 every 4 weeks and wherein serum amyloid A levels are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 3 mg/kg of polypeptide with SEQ ID NO: 34 every 4 weeks and wherein serum amyloid A levels are decreased by and maintained at 30% or more (reduction) compared to baseline (i.e. pre-treatment or normal) levels.

In a preferred aspect, the serum amyloid A levels are decreased by and maintained at 30% or more, 40% or more, 50% or more, 60% or more, or even 70% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 4 weeks, wherein serum amyloid A levels are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 4 weeks and wherein serum amyloid A levels are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 4 weeks and wherein serum amyloid A levels are decreased by and maintained at 30% or more (reduction) compared to baseline (i.e. pre-treatment or normal) levels.

In a preferred aspect, the serum amyloid A levels are decreased by and maintained at 30% or more, 40% or more, 50% or more, 60% or more, or even 70% or more (reduction) compared to baseline (i.e. pre-treatment or normal) levels.

The present invention also relates to a method for inhibiting IL-6 mediated signaling in a subject, said method comprising administering to the subject a polypeptide with SEQ ID NO: 34 in an amount of 6 mg/kg of polypeptide with SEQ ID NO: 34 every 8 weeks, wherein serum amyloid A levels are decreased by and maintained at 30% or more (reduction) compared to baseline (i.e. pre-treatment or normal) levels. The invention thus also relates to a polypeptide with SEQ ID NO: 34 for inhibiting IL-6 mediated signaling, wherein the polypeptide is administered in an amount of 6 mg/kg of polypeptide with SEQ ID NO: 34 every 8 weeks and wherein serum amyloid A levels are decreased by and maintained at 30% or more (reduction) compared to baseline (i.e. pre-treatment or normal) levels. The invention also relates to a polypeptide with SEQ ID NO: 34 for treatment of diseases and/or disorders associated with IL-6 mediated signaling, wherein the polypeptide is administered in an amount of 6 mg/kg of polypeptide with SEQ ID NO: 34 every 8 weeks and wherein serum amyloid A levels are decreased by and maintained at 30% or more (reduction) compared to baseline (i.e. pre-treatment or normal) levels.

In a preferred aspect, the serum amyloid A levels are decreased by and maintained at 30% or more, 40% or more, 50% or more, 60% or more, or even 70% or more (reduction) compared to baseline (i.e. pre-treatment or normal) levels.

Therapeutic Applications

The present invention provides methods and dosing schedules with polypeptides that are directed against IL-6R, which provide unexpectedly prolonged inhibition of IL-6 mediated signaling in a subject.

As such, the methods and dosing schedules of the present invention can be used for the prevention and treatment (as defined herein) of diseases and/or disorders related to IL-6 mediated signaling with lower doses and/or less frequent dosing than used for other therapeutics. Generally, "diseases and/or disorders related to IL-6 mediated signaling" can be defined as diseases and/or disorders that can be prevented and/or treated, respectively, by suitably administering to a subject in need thereof (i.e. having the disease and/or disorder or at least one symptom thereof and/or at risk of attracting or developing the disease or disorder) of either a polypeptide of the invention (and in particular, of a pharmaceutically active amount thereof) and/or of a known active principle active against IL-6, IL-6R, the IL-6/IL-6R complex (optionally in further complex with gp130) or a biological pathway or mechanism in which IL-6 and IL-6R are involved (and in particular, of a pharmaceutically active amount thereof).

Diseases and/or disorders related to IL-6 mediated signaling encompass diseases and disorders associated with IL-6R, with IL-6, with the IL-6/IL-6R complex (optionally in further complex with gp130), and/or with the signaling pathway(s) and/or the biological functions and responses in which IL-6, IL-6R and/or the IL-6/IL-6R complex (optionally in further complex with gp130) are involved, and in particular diseases and disorders associated with IL-6R, with IL-6, with the IL-6/IL-6R complex (optionally in further complex with gp130), and/or with the signaling pathway(s) and/or the biological functions and responses in which IL-6R, IL-6 and/or the IL-6/IL-6R complex (optionally in further complex with gp130) are involved, which are characterized by excessive and/or unwanted signaling mediated by IL-6 or by the pathway(s) in which IL-6 is involved.

Examples of such diseases and disorders associated with IL-6R, with IL-6, with the IL-6/IL-6R complex, and/or with the signaling pathway(s) and/or the biological functions and responses in which IL-6, IL-6R and/or the IL-6/IL-6R complex are involved, will be clear to the skilled person based on the disclosure herein, and for example include the following diseases and disorders: sepsis (Starnes et al. 1999, J. Immunol. 148: 1968) and various forms of cancer such as multiple myeloma disease (MM), renal cell carcinoma (RCC), plasma cell leukaemia (Klein et al. 1991, Blood 78: 1198-1204), lymphoma, B-lymphoproliferative disorder (BLPD) and prostate cancer. Non-limiting examples of other diseases caused by excessive IL-6 production or signaling include bone resorption (osteoporosis) (Roodman et al. 1992, J. Clin. Invest. 89: 45-52; Jilka et al. 1992, Science 257: 88-91), cachexia (Strassman et al. 1992, J. Clin. Invest. 89: 1681-1684), psoriasis, mesangial proliferative glomerulonephritis, Kaposi's sarcoma, AIDS-related lymphoma (Emilie et al. 1994, Blood 84: 2472-2479), inflammatory diseases and disorder such as rheumatoid arthritis, systemic onset juvenile idiopathic arthritis, hypergammaglobulinemia (Grau et al. 1990, J. Exp. Med. 172: 1505-1508), Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al. 1991, J. Clin. Invest. 87: 739-742). Other IL-6R, IL-6 and/or IL-6/IL-6R complex related disorders will be clear to the skilled person. Such diseases and disorders are also generally referred to herein as "IL-6R related diseases and/or disorders" or "IL-6 related diseases and/or disorders".

The methods and dosing schedules of the present invention that modulate, and in particular inhibit and/or prevent for prolonged periods of time and/or at lower doses and/or by less frequent dosing, binding of IL-6 to IL-6R, act as antagonist and will generally be used for the prevention and treatment (as defined herein) of these "IL-6R related diseases and/or disorders", "IL-6 related diseases and/or disorders" and/or "diseases and/or disorders related to IL-6 mediated signaling".

The invention thus also relates to a polypeptide of the invention for the prevention and treatment (as defined herein) of these "IL-6R related diseases and/or disorders", "IL-6 related diseases and/or disorders" and/or "diseases and/or disorders related to IL-6 mediated signaling" wherein the polypeptide inhibit and/or prevent for prolonged periods of time and/or at lower doses and/or by less frequent dosing, binding of IL-6 to IL-6R.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be a human being. As will be clear to the skilled person, the subject to be treated will in particular be a person suffering from, or at risk of, the diseases and/or disorders mentioned herein. For example, the subject may be a person suffering from, or at risk of, a disease and/or disorder related to IL-6 mediated signaling.

In particular, the polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

Definitions

Unless indicated or defined otherwise, all terms used have their usual meaning in the art, which will be clear to the skilled person. Reference is for example made to the standard handbooks, such as Sambrook et al. "Molecular Cloning: A Laboratory Manual" (2nd. Ed.), Vols. 1-3, Cold Spring Harbor Laboratory Press (1989); F. Ausubel et al. eds., "Current protocols in molecular biology", Green Publishing and Wiley Interscience, New York (1987); Lewin "Genes II", John Wiley & Sons, New York, N.Y., (1985); Old et al. "Principles of Gene Manipulation: An Introduction to Genetic Engineering", 2nd edition, University of California Press, Berkeley, Calif. (1981); Roitt et al. "Immunology" (6th. Ed.), Mosby/Elsevier, Edinburgh (2001); Roitt et al. Roitt's Essential Immunology, $10^{th}$ Ed. Blackwell Publishing, U K (2001); and Janeway et al. "Immunobiology" (6th Ed.), Garland Science Publishing/Churchill Livingstone, New York (2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews: Presta 2006 (Adv. Drug Deliv. Rev. 58 (5-6): 640-56), Levin and Weiss 2006 (Mol. Biosyst. 2(1): 49-57), Irving et al. 2001 (J. Immunol. Methods 248(1-2): 31-45), Schmitz et al. 2000 (Placenta 21 Suppl. A: S106-12), Gonzales et al. 2005 (Tumour Biol. 26(1): 31-43), which describe techniques for protein engineering, such as affinity maturation and other techniques for improving the specificity and other desired properties of proteins such as immunoglobulins.

A nucleic acid sequence or amino acid sequence is considered to be "(in) essentially isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

In addition, the term "sequence" as used herein (for example in terms like "immunoglobulin sequence", "variable domain sequence", "immunoglobulin single variable domain sequence", "VHH sequence" or "protein sequence"), should generally be understood to include both the relevant amino acid sequence as well as nucleic acid sequences or nucleotide sequences encoding the same, unless the context requires a more limited interpretation.

An amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The term "specificity" refers to the number of different types of antigens or antigenic determinants to which a particular antigen-binding molecule or antigen-binding protein (such as a Nanobody or a polypeptide of the invention) can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles or more). Any $K_D$ value greater than $10^{-4}$ mol/liter (or any $K_A$ value lower than $10^4$ liter/moles) is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person.

Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship $[K_D=1/K_A]$.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well-known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10,000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units $M^{-1}s^{-1}$. The on-rate may vary between $10^2$ $M^{-1}s^{-1}$ to about $10^2$ $M^{-1}s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}$=0.69 s).

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known Biacore instruments.

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+C_{ref}/K_{D\ ref})$. Note that if $c_{ref}\ll K_{D\ ref}$, $K_D\approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth et al. 1996 (Chemical Stability of Pharmaceuticals: A Handbook for Pharmacists and Peters et al, Pharmacokinete analysis: A Practical Approach). Reference is also made to Gibaldi and Perron 1982 (Pharmacokinetics, published by Marcel Dekker, 2nd Rev. edition).

As will also be clear to the skilled person (see for example pages 6 and 7 of WO 04/003019 and in the further references cited therein), the half-life can be expressed using parameters such as the t½-alpha, t½-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t½-beta, either with or without an increase in the t½-alpha and/or the AUC or both.

A polypeptide of the invention is said to "reduce levels of a marker (such as e.g. CRP, ESR, fibrinogen or serum amyloid A) by x % or more" or to "reduce levels of a marker by x % or more compared to baseline (i.e. pre-treatment or normal) levels" if administration of the polypeptide of the invention to the subject results in a reduction of the levels of said marker of x % compared to the levels before the treatment or compared to normal levels. In this case the levels of the marker in the treated subject are "decreased by x % or more" or "decreased by x % or more compared to baseline (i.e. pre-treatment or normal) levels". This means that the levels of the marker in the treated subject will be x % lower compared to the levels of the marker before treatment or compared to the normal levels of the marker. For example, if a polypeptide of the invention is said to "reduce serum levels of CRP by 30% or more" or to "reduce serum levels of CRP by 30% or more compared to baseline (pre-treatment or normal) levels", the serum levels of CRP in the treated subject will be 30% lower compared to the levels of CRP before treatment or compared to the normal levels of CRP. In this case the serum levels of CRP in the treated subject are "decreased by 30% or more" or "decreased by 30% or more compared to baseline (i.e. pre-treatment or normal) levels".

A polypeptide of the invention is said to "maintain levels of a marker (such as e.g. CRP, ESR, fibrinogen or serum amyloid A) at x % or more reduction" or "maintain levels of a marker (such as e.g. CRP, ESR, fibrinogen or serum amyloid A) at x % or more reduction compared to baseline levels" if the reduced levels of the marker are maintained x % lower compared to the levels of the marker before treatment or compared to the normal levels of the marker. In this case the levels of the marker in the treated subject are "maintained at x % or more (reduction)" or "maintained at x % or more (reduction) compared to baseline (i.e. pre-treatment or normal) levels". This means that the levels of the marker in the treated subject continue to be x % lower compared to the levels of the marker before treatment or compared to the normal levels of the marker. For example a polypeptide of the invention is said to maintain serum levels of CRP "at 30% or more reduction" if the reduced levels of serum CRP are maintained 30% or more lower compared to the serum CRP levels before treatment or compared to the normal serum levels of CRP. In this case the serum levels CRP in the treated subject are "maintained at 30% or more (reduction)" or "maintained at 30% or more (reduction) compared to baseline (i.e. pre-treatment or normal) levels". This means that the serum levels of CRP in the treated subject continue to be 30% lower compared to the serum levels of CRP before treatment or compared to the normal serum levels of CRP.

The Figures, and the Experimental Part/Examples are only given to further illustrate the invention and should not be interpreted or construed as limiting the scope of the invention and/or of the appended claims in any way, unless explicitly indicated otherwise herein.

EXAMPLES

List of Abbreviations

ADA Anti-drug antibody
bw bodyweight
C Concentration
CL Clearance
CLi Inter-compartmental flow
$CL_{IL6R}$ Target mediated clearance
$CL_{non-IL6R}$ Linear clearance
CRP C-reactive protein
DRF Dose range finding
ESR Erythrocyte sedimentation rate
h Hour
i.e. Id est
i.v. Intravenous
IC50 Concentration at which half of maximal effect is observed
Imax Maximal effect
kin Zero order synthesis rate constant
km Substrate concentration when the velocity of the reaction is ½ Vmax
kout First order elimination rate constant
MAD Multiple ascending dose
min Minutes
MTD Maximum tolerated dose
n Sigmoidicity factor
nM Nanomolar
PD Pharmacodynamic(s)
PK Pharmacokinetic(s)
Q2W Every 2 weeks
Q4W Every 4 weeks
Q8W Every 8 weeks
R Response
SAA Serum amyloid A
SAD Single ascending dose
SAEs Serious adverse events
sIL-6R Soluble interleukin 6 receptor
Vc Central volume
Vdss Volume of distribution at steady-state
Vmax Maximum velocity
Vt Peripheral volume
Determination of sIL-6R (=Total sIL-6R) Levels in Serum The method to determine total sIL-6R concentrations in human plasma was an in-house developed sandwich enzyme-linked immunosorbent assay (ELISA). A non-neutralizing anti-IL-6R monoclonal antibody (B—N12) was first coated on a 96 well Maxisorp plate by adsorption, after which excess binding sites were blocked with PBS-1% casein. Calibrators and validation samples were prepared from stock solutions of recombinant human sIL-6R using cynomolgus monkey sIL-6R free plasma and diluent (PBS/ 0.1% casein/0.05% Tween20 supplemented with 100 ng/mL IL6R304 to overcome drug interference). After transfer of the calibrators and samples onto the plate, detection was performed with a biotinylated goat anti-human IL-6R antibody and horseradish peroxidase (HRP)-labeled streptavidin. In the presence of $H_2O_2$, the peroxidase catalyzes a chemical reaction with the enhanced soluble 3,3',5,5'-tetramethylbenzidine (esTMB) resulting in a colorimetric change. After stopping the colorimetric reaction with 1M HCl, the optical density was measured at a wavelength of 450 nm in a plate spectrophotometer.

Determination of IL-6 Levels in Serum

For determining IL-6 concentrations in human serum, the commercially available "Human IL-6 Quantiglo ELISA Kit" from R&D Systems was used (cat #Q6000B). The assay was performed as described in the manufacturer's instructions. Assay Diluent RD1-83 was supplemented with 10 µg/mL IL6R304 before use to overcome IL-6R interference.

Determination of CRP Levels

For determining CRP concentrations in human serum, the commercially available "IMMAGE Immunochemistry Systems C-Reactive Protein (Kit Recorder #447280)" from Beckman Coulter Inc. (Brea, Calif., US) was used. The assay was performed as described in the manufacturer's instructions.

Determination of ESR Levels

For determining ESR levels in serum, the following commercially available assays were used: the Greiner ESR tube or the Preanalytics—VACUETTE® Evacuated Collection Tubes (Greiner Bio-One GmbH, Kremsmuenster, Austria), the Sarstedt Sediplus® 2000 (Sarstedt, Nümbrecht, Germany), or the Becton Dickinson Seditainer (Becton Dickinson, Franklin Lakes, N.J., USA).

Determination of Fibrinogen Levels

For determining fibrinogen levels in serum, the following commercially available assays were used: the STA® Fibrinogen 5 or the STA® Compact (Stago, Asniéres sur Seine, France), the ACL TOP® 500 CTS (Beckman Coulter Inc., Brea, Calif., US), or the Ceveron® alpha (TC technoclone, Vienna, Austria).

Determination of Serum Amyloid A Levels

The method to determine serum amyloid A was a sandwich enzyme-linked immunosorbent assay (ELISA). A highly purified monoclonal antibody against human SAA was coated onto the wells of the microtiter strip. Standards of known human SAA content, controls and unknown samples were pipetted into the coated wells, followed by the addition of biotinylated second monoclonal antibody. After washing, Streptavidin-Peroxidase was added. After a second incubation and washing to remove all unbound enzyme, a substrate solution (TMB) was added. The intensity of the obtained color was directly proportional to the concentration of human SAA present in the original specimen.

Example 1: Toxicology Studies with IL6R304

In a single dose toxicity study IL6R304 was administered to male cynomolgus monkeys as single i.v. doses of 0, 1, 5, 10, 25, 100 mg/kg b.w IL6R304. Blood samples for pharmacokinetic (PK), anti-drug antibody (ADA), and pharmacodynamic (PD) analysis purposes were collected from all animals at pre-dose and at selected time points post-dose. Samples were analysed for PK, PD and ADA purposes using validated methods.

Toxicokinetic samples were taken at 5 min, 0.5, 3, 8 h, day 1, 2, 4, 7, 14, 21, 28, 35, 49, 63 and 77 days post-dose.

Example 2: Preclinical Data

Pharmacokinetic (PK) and pharmacodynamic (PD) modeling was performed on data generated in a single dose toxicity study with IL6R304 in the cynomolgus monkey as described in Example 1.

2.1 Pharmacokinetic Modeling of Cynomolgus Monkey IL6R304 Plasma Concentrations

An open two-compartmental pharmacokinetic model with linear and a non-linear clearance from the central compartment captured the non-linear pharmacokinetic behavior of IL6R304 in the cynomolgus monkey.

The linear clearance mechanism is likely related to the non-saturable, and non-target mediated removal of IL6R304 and corresponds to the slow and non-specific proteolytic degradation of IL6R304. The non-linear and target-mediated clearance process is a saturable clearance mechanism; most probably representing binding of IL6R304 to membrane bound IL6-R and subsequent internalization and clearance.

All available individual plasma concentration data after a single i.v. dose were used for building the pharmacokinetic model (WinNonlin Professional Software Version 5.1 (Pharsight Corporation, Mountain View Calif., USA)).

At low IL6R304 concentrations ($C<<<K_m$) the contribution of the IL-6R-mediated clearance ($CL_{IL6-R}$) is predominant and equals $V_{max}/K_m$. At high IL6R304 concentrations ($C>>>Km$), the IL-6R-mediated clearance pathway becomes saturated and will proceed at the maximum mass turnover (i.e. $V_{max}$). Consequently, the overall clearance (CL) is dominated by the linear, non-IL-6R mediated pathway ($CL_{NON-IL6R}$).

The estimated PK parameters of IL6R304 in the cynomolgus monkey are listed in Table B-1. All parameters were estimated with sufficient precision.

TABLE B-1

Pharmacokinetic parameters of IL6R304 in the cynomolgus monkey.

| Parameter | Estimate | % CV |
|---|---|---|
| $V_c$ (mL/kg) | 48.5 | 4.0 |
| $V_t$ (mL/kg) | 47.6 | 6.5 |
| $V_{dss}$ (mL/kg) | 96.1 | |
| $CL_{NON-IL6R}$ (mL/h · kg) | 0.244 | 3.5 |
| $CL_t$ (mL/h · kg) | 1.18 | 18.7 |
| $V_{max}$ (µg/h · kg) | 2.498 | 11.7 |
| $K_m$ (µg/mL) | 0.924 | 35.0 |
| $CL_{IL6R}$ (mL/h · kg) | 2.70 | |

2.2 Semi-Mechanistic PK/PD Modeling (Cynomolgus Monkey IL6R304 Plasma Concentrations and Serum sIL-6R Concentrations)

In order to describe the pharmacodynamic effect of IL6R304 in a mathematical model sIL-6R was selected as a robust and precisely quantifiable biomarker which correlates to the concentration of active drug. The influence of IL6R304 administration on total sIL-6R levels can be explained by direct binding of IL6R304 to the receptor: the complex stays in circulation via the half-life extension moiety of IL6R304 (i.e. albumin binding). As the measurable changes in total sIL-6R concentrations follow a time-delayed kinetic, an indirect response model best describes the PK/PD relationship and was used to describe the effect of i.v. administered IL6R304 on the accumulation of sIL-6R/IL6R304 complex levels.

The model describes a drug response that results from the inhibition of the elimination of sIL-6R when bound to IL6R304. In this indirect response model, the rate of change of total sIL-6R-IL6R304 complex (Response R) is described by:

$$\frac{dR}{dt} = Kin - Kout * \left[1 - Imax * \frac{C^n}{IC50^n + C^n}\right] * R$$

With Kin, the zero order synthesis rate; R, the total sIL-6R; Imax, the maximum inhibition; C, the IL6R304 plasma concentration; IC50, the IL6R304 concentration at which half of the maximum effect is observed; n, the dose-response shape factor; and Kout, the first order elimination rate constant of sIL-6R.

All available total sIL-6R data from the single dose toxicity study after i.v. administration were used to build the PK/PD model (WinNonlin Professional Software Version 5.1, Pharsight Corporation, Mountain View Calif., USA) using the pharmacokinetic function as input function for the indirect response PK/PD model.

The pharmacodynamic effect of i.v. administered IL6R304 on the physiological turnover of serum sIL-6R in the monkey were adequately captured using a semi-mechanistic PK/PD model (indirect response model).

IL6R304 was able to almost completely inhibit the elimination of sIL-6R via the primary pathway ($I_{max}$=97%), and at this maximum effect level the calculated $k_{out}$ and corresponding half-life of sIL-6R was similar to that of cynomolgus monkey serum albumin. With an estimated $IC_{50}$ of 68 ng/mL or 2.64 nM, IL6R304 was shown to be a potent inhibitor of the elimination of non-complexed sIL-6R in cynomolgus monkey.

The estimated pharmacodynamic parameters of IL6R304, in cynomolgus monkey, are listed in Table B-2. All parameters were estimated with a sufficient degree of precision as indicated by CV % values below 25%.

TABLE B-2

Pharmacodynamic parameters of IL6R304 in cynomolgus monkeys.

| Parameter | Estimate | % CV |
|---|---|---|
| $K_{in}$ (ng/mL · h) | 2.56 | 7.1 |
| $R_0$ (ng/mL) | 21.8 | 4.8 |
| $I_{max}$ (%) | 0.974 | 0.4 |
| $IC_{50}$ (µg/mL) | 0.068 | 24.4 |
| $IC_{50}$ (nM) | 2.64 | |
| n | 0.87 | 10.5 |

Example 3: Scaling to Human: Simulation of IL6R304 PK/PD in Humans

The PK/PD model developed to describe the temporal profile of IL6R304 concentrations and corresponding serum sIL-6R levels in the cynomolgus monkey was scaled to human to assist in the dose selection of the first in human study.

To simulate the temporal profile of IL6R304 in human after i.v. bolus, volumes of distribution in the central ($V_c$) and peripheral ($V_t$) compartments, the inter-compartmental flow ($CL_i$) and the linear clearance (CL) were scaled using standard allometric factors (1 for $V_c$ and $V_t$, 0.75 for $CL_i$ and CL) (Boxenbaum and DiLea 1995, First-time-in-human dose selection: allometric thoughts and perspectives J. Clin. Pharmacol. 35: 957-966). For the nonlinear clearance, depending on the parameters $V_{max}$ and $K_m$, the $V_{max}$ was assumed to be equal as that reported for tocilizumab (TCZ) (as IL6R304 and TCZ bind to the same target with similar potency) (in-house data), and the $K_m$ was assumed to be equal to values obtained for cynomolgus monkey, as suggested by an in-house model comparing TCZ and IL6R304 behavior and indicating in cynomolgus monkey for IL6R304 a $K_m$ similar to that of TCZ, reported as similar to that in human.

The PK parameters used for the simulation of the IL6R304 plasma concentration-time profiles are listed in Table B-3.

TABLE B-3

Allometrically scaled pharmacokinetic parameters of IL6R304 in humans.

| Parameter (Units) | |
|---|---|
| $V_c$ (mL/kg) | 48.5 |
| $V_t$ (mL/kg) | 47.6 |
| $CL_{NON-IL6R}$ (mL/h · kg) | 0.0918 |
| $CL_i$ (mL/h · kg) | 0.446 |
| $V_{max}$ (µg/h · kg) | 4.46 |
| $K_m$ (µg/mL) | 0.924 |

Consequently, the predicted IL6R304 plasma levels were used in the PK/PD model developed in monkey to describe the temporal profile of total sIL-6R in human. In this model system parameters (baseline (R0) and kout) for human were derived from the literature (Kyrtsonis M. C., Desoussis G., Zervas C., Perifanis V., Baxevanis C., Stamatelou M., Maniatis A. 1996, Soluble interleukin-6 receptor (sIL-6R), a new prognostic factor in multiple myeloma. British Journal of hematology 93 (2): 398-400; Levi M., Charoin J. E., Frey N., Delor I., Jacqmin P. 2009, A mechanistic target mediated drug disposition (TMDD) model is required to correctly estimate the bioavailability of a subcutaneous formulation of Tocilizumab (TCZ), a monoclonal antibody with non-linear kinetics. American Conference on Pharmacometrics (ACoP) 2009, Mashantucket 2009), whereas the drug specific parameters IC50, $I_{max}$ and n were assumed equal to those determined in the monkey.

In Table B-4, the PD parameters used for the simulation of the IL6R304 serum sIL-6R concentration-time profiles are listed.

TABLE B-4

Pharmacodynamic parameters of IL6R304 used in the PK/PD simulations of serum sIL-6R concentrations.

| Parameter (Units) | |
|---|---|
| $K_{out}$ (h$^{-1}$) | 0.0625 |
| $R_0$ (ng/mL) | 27.7 |
| $I_{max}$ (%) | 0.974 |
| $IC_{50}$ (µg/mL) | 0.068 |
| n | 0.87 |

Simulated PD profiles indicated a dose-dependent increase of serum sIL-6R after a single i.v. dose with IL6R304, consistent with the indirect response model describing inhibition of serum sIL-6R elimination.

Example 4: Clinical Data

Clinical Study Design

A multi-center, randomized, double-blind, placebo-controlled, dose-escalation, phase I/II study in patients with RA, consisting of a single ascending dose (SAD) part and a multiple ascending dose (MAD) part, was conducted.

The SAD part consisted of 1 group of 4 (2+2) patients and 3 groups of 8 (6+2) patients each. In the first group 2 patients received a single intravenous (iv) dose of IL6R304 (0.3 mg/kg) and 2 patients received a single iv dose of placebo. As of the second group, 6 patients received a single intravenous (iv) dose of IL6R304 (1, 3, 6 mg/kg) and 2 patients received a single iv dose of placebo. At the end of the SAD part an interim PK/PD analysis was done to confirm the adequacy of the anticipated doses and dosing regimens to be used in the MAD part of the study.

The MAD part consists of 3 groups (Groups 6-8) of 12 patients each. In each group, 10 patients receive multiple iv doses of IL6R304 and 2 patients receive multiple iv doses of placebo. In the original protocol, the following dose levels were considered: 1 mg/kg Q2W (every two weeks), 3 mg/kg Q2W, 6 mg/kg Q4W (every four weeks) for 12 weeks of treatment.

Blood samples are planned to be collected for determination of IL6R304 levels at pre-dose, end of injection/infusion, 8 h, and Day 2, 3, 4, 5, 8, 15, 29, 36 and 57 post-dose. The same time schedule is planned for biomarkers (CRP, ESR, SAA, fibrinogen, IL-6, sIL-6R, TNF-α, IL-1β and IFN-γ) determination, except the end of injection/infusion and the Day 5 time-points.

An interim PK/PD analysis is performed at the end of the SAD part of the study on the IL6R304 and the sIL-6R data, as their expected profiles after multiple dose were considered most critical for the dose/dosing regimen selection for the second part of the study.

Preliminary Results from SAD Study
C-Reactive Protein (CRP)

An overview of the C-Reactive Protein (CRP) changes from baseline during the SAD study for the different treatment groups is given in FIG. 4 and Table B-5. A rapid and dose-proportional decrease from baseline was observed for this biomarker. The longest suppression (more than 57 days) was observed for the 6 mg/kg treatment group. This duration of the CRP reduction supports Q4W (every 4 weeks) and Q8W (every 8 weeks) dosing. The largest effect on CRP and disease activity score was obtained at 6 mg/kg.

Following IL6R304 administration, CRP levels declined rapidly from 8 hours post-dose (the first post-dose sampling time point). The maximum reduction in mean CRP levels varied between 74% and 53% of baseline across the dose range studied (60% on Day 8 for 0.3 mg/kg, 53% on Day 15 for 1 mg/kg, 74% on Day 29 for 3 mg/kg, 63% on Day 8 for 6 mg/kg).

There was no clear dose response with respect to magnitude of CRP decrease, but a dose-related increase in the duration of reduction was apparent.

The corresponding CRP levels for the placebo group did not show a clinically meaningful change from baseline.

Erythrocytes Sedimentation Rate (ESR)

An overview of the ESR changes from baseline during the SAD study for the different treatment groups is given in Table B-6.

Following IL6R304 administration, the ESR values declined starting from 48 hours post-dose onwards. The maximum decrease in mean ESR values varied between 82% and 32% of baseline across the dose range studied (32% on Day 4 for 0.3 mg/kg, 59% on Day 8 and 59% on Day 15 for 1 mg/kg, 82% on Day 15 for 3 mg/kg, 69% on Day 57 for 6 mg/kg).

A dose-dependent increase in the duration of reduction was apparent. The ESR values returned to baseline at Day 57 for all dose levels except the 6 mg/kg group.

The corresponding ESR values for the placebo group did not show a clinically meaningful change from baseline.

TABLE B-5

CRP values (relative changes from baseline (SD))

| Time after dosing | | Placebo (N = 8) | 0.3 mg/kg | 1 mg/kg | 3 mg/kg | 6 mg/kg |
|---|---|---|---|---|---|---|
| DAY1_8H | N | 8 | 2 | 6 | 6 | 6 |
| | % | −3.3 (17.25) | 4.7 (6.65) | −5.4 (14.16) | −17.8 (13.33) | −10.9 (12.73) |
| DAY2_24H | N | 8 | 2 | 6 | 6 | 6 |
| | % | −13.0 (15.29) | 5.6 (30.12) | −18.3 (8.72) | −34.8 (9.69) | −26.9 (12.22) |
| DAY3_48H | N | 8 | 2 | 6 | 5 | 6 |
| | % | −18.2 (16.96) | −37.7 (31.50) | −40.8 (8.52) | −57.7 (15.80) | −45.0 (9.84) |
| DAY4_72H | N | 8 | 2 | 6 | 5 | 6 |
| | % | −11.1 (27.33) | −59.7 (19.10) | −36.3 (23.93) | −68.6 (16.19) | −59.2 (9.81) |
| DAY 8 | N | 8 | 2 | 6 | 6 | 6 |
| | % | −18.9 (28.24) | −60.2 (41.56) | −49.1 (32.19) | −66.3 (30.00) | −63.4 (23.15) |
| DAY 15 | N | 8 | 2 | 6 | 5 | 6 |
| | % | 2.2 (42.18) | 145.1 (28.74) | −52.7 (23.48) | −72.6 (24.49) | −43.5 (72.19) |
| DAY 29 | N | 8 | 2 | 6 | 5 | 6 |
| | % | −12.6 (26.31) | 51.9 (29.99) | 23.2 (53.60) | −73.5 (22.34) | −62.8 (27.30) |
| DAY 36 | N | 8 | 2 | 6 | 6 | 6 |
| | % | 1.5 (51.68) | 39.7 (34.46) | 42.2 (73.16) | 11.3 (144.98) | −59.7 (37.94) |
| DAY 57 | N | 8 | 2 | 6 | 5 | 6 |
| | % | 11.1 (60.11) | 84.5 (119.49) | 5.1 (27.92) | −3.9 (52.21) | −52.1 (21.86) |
| FOLLOW UP | N | 8 | 2 | 6 | 6 | 6 |
| | % | 15.2 (57.60) | 39.0 (37.36) | 4.0 (17.40) | −14.9 (50.98) | −14.8 (37.85) |

TABLE B-6

Erythrocytes Sedimentation Rate (relative changes from baseline (SD))

| Time after dosing | | Placebo (N = 8) | 0.3 mg/kg | 1 mg/kg | 3 mg/kg | 6 mg/kg |
|---|---|---|---|---|---|---|
| DAY1_8H | N | 8 | 2 | 6 | 6 | 6 |
| | % | 23.4 (44.97) | 2.5 (21.19) | −20.2 (33.01) | −14.5 (25.31) | 6.5 (19.90) |
| DAY2_24H | N | 8 | 2 | 6 | 6 | 6 |
| | % | 11.4 (47.08) | −6.9 (25.53) | −12.5 (59.29) | −15.1 (23.32) | −10.1 (12.95) |
| DAY3_48H | N | 8 | 2 | 6 | 5 | 6 |
| | % | 6.1 (45.79) | 7.1 (10.10) | 0.5 (87.12) | −23.5 (14.08) | −35.4 (33.89) |
| DAY4_72H | N | 8 | 2 | 6 | 5 | 6 |
| | % | 23.4 (24.95) | −32.2 (7.44) | −43.5 (23.08) | −43.4 (14.18) | −28.0 (18.28) |
| DAY 8 | N | 8 | 2 | 6 | 6 | 6 |
| | % | 24.3 (54.28) | −26.1 (19.22) | −58.7 (17.16) | −67.5 (13.45) | −60.2 (30.95) |
| DAY 15 | N | 8 | 2 | 6 | 5 | 6 |
| | % | 58.0 (81.98) | −26.1 (19.22) | −58.8 (26.26) | −82.4 (8.10) | −53.8 (32.05) |
| DAY 29 | N | 8 | 2 | 6 | 5 | 6 |
| | % | 39.7 (82.42) | 5.6 (16.77) | 8.3 (45.03) | −81.2 (9.40) | −60.3 (27.72) |
| DAY 36 | N | 8 | 2 | 6 | 5 | 6 |
| | % | 47.6 (81.74) | 18.1 (9.82) | 14.7 (60.99) | −70.8 (16.36) | −66.3 (21.70) |
| DAY 57 | N | 8 | 2 | 6 | 5 | 6 |
| | % | 40.9 (68.08) | 15.0 (3.51) | 23.6 (40.51) | 3.0 (18.99) | −69.3 (19.63) |
| FOLLOW UP | N | 8 | 2 | 6 | 6 | 6 |
| | % | 82.6 (118.05) | −6.9 (25.53) | 1.3 (56.89) | −17.8 (30.31) | −6.5 (40.59) |

Fibrinogen

An overview of the fibrinogen changes from baseline during the SAD study for the different treatment groups is given in Table B-7.

Overall, a decrease from baseline in fibrinogen levels was observed following IL6R304 administration from 8 hours post-dose (the first post-dose sampling time point) for all dose levels. The maximum decrease in mean fibrinogen levels varied between 52% and 32% from baseline across the dose range studied (32% on Day 8 for 0.3 mg/kg, 42% on Day 15 for 1 mg/kg, 52% on Day 29 for 3 mg/kg, 37% on Day 15 for 6 mg/kg).

A dose-dependent increase in the duration of reduction was apparent. Fibrinogen levels returned to baseline at Day 57 for all dose levels except 6 mg/kg group.

The corresponding fibrinogen levels for the placebo group did not show a clinically relevant change from baseline.

Serum Amyloid A (SAA)

An overview of the serum amyloid A changes from baseline during the SAD study for the different treatment groups is given in Table B-8.

Overall, a decrease from baseline in SAA concentration was observed following IL6R304 administration for all dose levels from 8 hours post-dose. The maximum decrease in mean SAA levels varied between 74% and 58% of baseline across the dose range studied (69% on Day 8 for 0.3 mg/kg, 60% on Day 4 for 1 mg/kg, 74% on Day 15 for 3 mg/kg, 58% on Day 8 for 6 mg/kg).

A dose-dependent increase in the duration of reduction of SAA levels was apparent.

The SAA concentrations of the placebo-treated subjects increased above baseline at most time points.

TABLE B-7

Fibrinogen (relative changes after baseline (SD))

| Time after dosing | | Placebo (N = 8) | 0.3 mg/kg | 1 mg/kg | 3 mg/kg | 6 mg/kg |
|---|---|---|---|---|---|---|
| DAY1_8 | N | 8 | 2 | 6 | 6 | 6 |
| | % | −2.7 (6.00) | −3.2 (9.69) | −11.3 (4.30) | −12.4 (5.38) | −4.5 (4.75) |
| DAY2_24H | N | 8 | 2 | 6 | 6 | 6 |
| | % | 7.8 (8.80) | −1.5 (22.73) | −7.0 (6.58) | −9.6 (9.27) | −2.3 (11.83) |
| DAY3_48H | N | 8 | 2 | 6 | 5 | 6 |
| | % | −0.5 (9.75) | −6.1 (19.40) | −17.9 (4.75) | −16.0 (16.42) | −7.0 (15.64) |
| DAY4_72H | N | 8 | 2 | 6 | 5 | 6 |
| | % | 0.7 (5.28) | −16.0 (26.28) | −15.7 (7.39) | −16.9 (29.86) | −19.1 (14.72) |
| DAY 8 | N | 8 | 2 | 6 | 6 | 6 |
| | % | 2.1 (9.85) | −31.6 (22.03) | −35.1 (4.75) | −38.6 (15.66) | −28.5 (16.49) |
| DAY 15 | N | 8 | 2 | 6 | 5 | 6 |
| | % | 4.1 (18.37) | 11.3 (28.88) | −41.9 (6.60) | −49.9 (16.79) | −36.5 (21.69) |
| DAY 29 | N | 8 | 2 | 6 | 5 | 6 |
| | % | 3.6 (19.40) | 12.6 (29.61) | 0.9 (20.06) | −52.1 (14.58) | −35.0 (22.27) |
| DAY 36 | N | 8 | 2 | 6 | 5 | 6 |
| | % | 4.0 (15.65) | 31.1 (37.50) | 12.5 (17.87) | −34.3 (22.68) | −34.3 (23.42) |
| DAY 57 | N | 8 | 2 | 6 | 5 | 6 |
| | % | 6.3 (24.63) | 22.0 (14.36) | 1.1 (20.28) | −8.6 (7.24) | −30.4 (15.10) |
| FOLLOW UP | N | 8 | 2 | 6 | 6 | 6 |
| | % | 5.4 (19.43) | −0.5 (13.56) | 2.4 (6.36) | −5.5 (30.33) | 0.7 (25.08) |

TABLE B-8

Serum amyloid A (relative changes from baseline (SD))

| Time after dosing | | Placebo (N = 8) | 0.3 mg/kg | 1 mg/kg | 3 mg/kg | 6 mg/kg |
|---|---|---|---|---|---|---|
| DAY1_8H | N | 8 | 2 | 6 | 6 | 6 |
| | % | −4.3 (18.69) | −11.9 (16.26) | −12.5 (18.77) | −29.7 (24.18) | −7.9 (11.10) |
| DAY2_24H | N | 8 | 2 | 6 | 6 | 6 |
| | % | −10.3 (24.86) | −8.8 (26.04) | −30.2 (25.81) | −28.8 (17.49) | −25.0 (14.67) |
| DAY3_48H | N | 7 | 2 | 6 | 5 | 6 |
| | % | −2.8 (48.38) | −42.9 (29.44) | −51.4 (25.35) | −60.6 (16.41) | −38.5 (44.93) |
| DAY4_72H | N | 7 | 2 | 6 | 5 | 6 |
| | % | 10.7 (66.30) | −65.9 (28.80) | −60.3 (21.63) | −58.6 (31.51) | −42.5 (53.67) |
| DAY 8 | N | 8 | 2 | 6 | 6 | 6 |
| | % | 38.1 (93.77) | −69.1 (38.69) | −44.4 (68.57) | −68.1 (30.70) | −58.2 (24.40) |
| DAY 15 | N | 8 | 2 | 6 | 5 | 6 |
| | % | 39.8 (86.52) | 144.5 (87.78) | −48.6 (35.78) | −73.6 (21.42) | −4.5 (143.16) |
| DAY 29 | N | 8 | 2 | 6 | 5 | 6 |
| | % | 22.3 (73.33) | 81.4 (27.43) | 16.2 (41.97) | −67.4 (25.90) | −43.7 (64.10) |
| DAY 36 | N | 8 | 2 | 6 | 5 | 6 |
| | % | 24.4 (56.16) | 46.0 (7.09) | 18.9 (54.92) | 17.4 (163.79) | −30.1 (31.49) |
| DAY 57 | N | 8 | 2 | 6 | 5 | 6 |
| | % | 78.2 (164.35) | 71.4 (41.68) | −10.5 (38.20) | −6.8 (71.87) | 17.9 (92.56) |
| FOLLOW UP | N | 8 | 2 | 6 | 6 | 6 |
| | % | 76.1 (114.40) | 14.1 (30.62) | 27.6 (58.82) | −6.4 (59.62) | −7.3 (62.82) |

Interleukin-6

The changes in IL-6 levels (pg/ml) during the SAD study for the different treatment groups is given in FIG. 6.

Following IL6R304 administration, mean IL-6 plasma concentrations increased from 8 hours post-dose up to the follow-up visit for all IL6R304 dose levels.

The maximum increase from baseline in mean levels varied between 11,076% and 216% of baseline across the dose range studied (216% on Day 4 for 0.3 mg/kg, 2,054% on Day 15 for 1 mg/kg, 11,076% on Day 3 for 3 mg/kg [note: 1 subject had a very high value of 48,419], 746% on Day 15 for 6 mg/kg).

As expected, mean IL-6 levels of the placebo group did not show a clinically relevant change from baseline.

Soluble Interleukin-6 Receptor (sIL-6R)

The changes in sIL-6R levels (ng/ml) during the SAD study for the different treatment groups is given in FIG. 7.

Following IL6R304 administration, mean sIL-6R concentrations increased from 8 hours post-dose, with a dose-dependent increase in the duration of increase in sIL-6R levels. A dose-related effect of IL6R304 was observed on the maximal sIL-6R concentrations and the duration of increased sIL-6R. The mean sIL-6R levels returned to baseline values at Day 29, Day 36, Day 57 and at follow-up for the 0.3, 1, 3 and 6 mg/kg dose groups respectively.

Mean sIL-6R levels of the placebo group did not show a clinically relevant change from baseline.

DAS28 Score

The 28 joints assessed for Disease activity score using 28 joint counts (DAS28 score) included the proximal interphalangeal joints of the fingers, the interphalangeal joints of the thumbs, the 10 metacarpophalangeal joints, plus the wrists, elbows, shoulders and knees. The DAS28 score is a validated index that combines the tender and swollen joint counts, CRP, and patient global assessment of disease activity.

In order to calculate the DAS28 score, each of the 28 joints were evaluated for tenderness and swelling. The DAS28 score was derived from the following formula:

$$DAS28 = 0.56 * \text{sqrt}(TEN28) + 0.28 * \text{sqrt}(SW28) + 0.36 * Ln(CRP+1) + 0.014 * GH + 0.96$$

sqrt=square root
TEN28=28 joint count for tenderness
SW28=28 joint count for swelling
Ln(CRP)=natural logarithm of CRP
GH=patient's global assessment of disease activity on a VAS of 0-100 mm.

The DAS28% change from baseline, measured at Day 57 and at follow-up, showed an improvement upon single dose administration of IL6R304, at all dose levels tested (Table B-9).

TABLE B-9

Summary of DAS28 Score

| Cohort | Time after | DAS score | Placebo (N = 8) | IL6R304 (N = 20) |
|---|---|---|---|---|
| 0.3 mg/kg | DAY 1 Pre-dose | n | 2 | 2 |
| | | Moderate disease | 1 (50.0%) | 1 (50.0%) |
| | | High disease activity | 1 (50.0%) | 1 (50.0%) |
| | DAY 57 | n | 2 | 2 |
| | | Low disease activity | 0 (0.0%) | 1 (50.0%) |
| | | Moderate disease | 1 (50.0%) | 1 (50.0%) |
| | | High disease activity | 1 (50.0%) | 0 (0.0%) |
| | FOLLOW UP | n | 2 | 2 |
| | | Moderate disease | 0 (0.0%) | 2 (100.0%) |
| | | High disease activity | 2 (100.0%) | 0 (0.0%) |
| 1 mg/kg | DAY 1 Pre-dose | n | 2 | 6 |
| | | Low disease activity | 0 (0.0%) | 1 (16.7%) |
| | | Moderate disease | 2 (100.0%) | 4 (66.7%) |
| | | High disease activity | 0 (0.0%) | 1 (16.7%) |

TABLE B-9-continued

| | | Summary of DAS28 Score | | |
|---|---|---|---|---|
| Cohort | Time after | DAS score | Placebo (N = 8) | IL6R304 (N = 20) |
| | DAY 57 | n | 2 | 6 |
| | | Remission | 1 (50.0%) | 1 (16.7%) |
| | | Low disease activity | 0 (0.0%) | 3 (50.0%) |
| | | Moderate disease | 1 (50.0%) | 2 (33.3%) |
| | FOLLOW-UP | n | 2 | 6 |
| | | Remission | 0 (0.0%) | 1 (16.7%) |
| | | Low disease activity | 1 (50.0%) | 1 (16.7%) |
| | | Moderate disease | 1 (50.0%) | 4 (66.7%) |
| 3 mg/kg | DAY 1 Pre-dose | n | 2 | 6 |
| | | Low disease activity | 0 (0.0%) | 1 (16.7%) |
| | | Moderate disease | 2 (100.0%) | 1 (16.7%) |
| | | High disease activity | 0 (0.0%) | 4 (66.7%) |
| | DAY 57 | n | 2 | 5 |
| | | Remission | 0 (0.0%) | 1 (20.0%) |
| | | Moderate disease | 2 (100.0%) | 4 (80.0%) |
| | FOLLOW-UP | n | 2 | 6 |
| | | Remission | 0 (0.0%) | 2 (33.3%) |
| | | Moderate disease | 2 (100.0%) | 3 (50.0%) |
| | | High disease activity | 0 (0.0%) | 1 (16.7%) |
| 6 mg/kg | DAY 1 Pre-dose | n | 2 | 6 |
| | | Low disease activity | 1 (50.0%) | 0 (0.0%) |
| | | Moderate disease | 1 (50.0%) | 3 (50.0%) |
| | | High disease activity | 0 (0.0%) | 3 (50.0%) |
| | DAY 57 | n | 2 | 6 |
| | | Remission | 0 (0.0%) | 2 (33.3%) |
| | | Low disease activity | 1 (50.0%) | 2 (33.3%) |
| | | Moderate disease | 1 (50.0%) | 2 (33.3%) |
| | FOLLOW-UP | n | 2 | 6 |
| | | Low disease activity | 1 (50.0%) | 1 (16.7%) |
| | | Moderate disease | 1 (50.0%) | 5 (83.3%) |

DAS28 > 5.1: high disease activity; 3.2 <= DAS28 <= 5.1: moderate disease activity; DAS28 < 3.2: low disease activity; DAS28 < 2.6: remission.

The duration of improvement of DAS28 exceeded the duration of CRP reduction for all dose groups, indicating that the effect of IL6R304 on clinical activity persisted beyond its effect on the CRP biomarker (FIG. 5; FIG. 8).

EULAR Response

The EULAR response criteria assess individual changes in DAS28 score during a clinical study. The EULAR response criteria are defined in Table B-10.

TABLE B-10

| | EULAR Response | | |
|---|---|---|---|
| | Improvement in DAS28 Score Relative to Baseline | | |
| Present DAS28 | >1.2 | 0.6-1.2 | <0.6 |
| <3.2 | good response | moderate response | no response |
| 3.2-5.1 | moderate response | moderate response | no response |
| >5.1 | moderate response | no response | no response |

The EULAR scores indicated an improvement upon single dose administration of IL6R304, at all dose levels tested (Table B-11).

TABLE B-11

| | Summary of EULAR Response (Safety Population) | | | |
|---|---|---|---|---|
| Cohort | Time after dosing | EULAR response | Placebo* | IL6R304 |
| 0.3 mg/kg | DAY 57 | n | 2 | 2 |
| | | GOOD | 0 (0.0%) | 1 (50.0%) |
| | | MODERATE | 1 (50.0%) | 1 (50.0%) |
| | | NO | 1 (50.0%) | 0 (0.0%) |
| | FOLLOW UP | n | 2 | 2 |
| | | MODERATE | 0 (0.0%) | 2 (100.0%) |
| | | NO | 2 (100.0%) | 0 (0.0%) |

TABLE B-11-continued

Summary of EULAR Response (Safety Population)

| Cohort | Time after dosing | EULAR response | Placebo* | IL6R304 |
|---|---|---|---|---|
| 1 mg/kg | DAY 57 | n | 2 | 6 |
| | | GOOD | 1 (50.0%) | 1 (16.7%) |
| | | MODERATE | 0 (0.0%) | 3 (50.0%) |
| | | NO | 1 (50.0%) | 2 (33.3%) |
| | FOLLOW UP | n | 2 | 6 |
| | | GOOD | 2 (100.0%) | 1 (16.7%) |
| | | MODERATE | 0 (0.0%) | 4 (66.7%) |
| | | NO | 0 (0.0%) | 1 (16.7%) |
| 3 mg/kg | DAY 57 | n | 2 | 5 |
| | | GOOD | 0 (0.0%) | 1 (20.0%) |
| | | MODERATE | 1 (50.0%) | 4 (80.0%) |
| | | NO | 1 (50.0%) | 0 (0.0%) |
| | FOLLOW UP | n | 2 | 6 |
| | | GOOD | 0 (0.0%) | 2 (33.3%) |
| | | MODERATE | 2 (100.0%) | 2 (33.3%) |
| | | NO | 0 (0.0%) | 2 (33.3%) |
| 6 mg/kg | DAY 57 | n | 2 | 6 |
| | | GOOD | 0 (0.0%) | 3 (50.0%) |
| | | MODERATE | 0 (0.0%) | 2 (33.3%) |
| | | NO | 2 (100.0%) | 1 (16.7%) |
| | FOLLOW UP | n | 2 | 6 |
| | | MODERATE | 0 (0.0%) | 4 (66.7%) |
| | | NO | 2 (100.0%) | 2 (33.3%) |
| Overall* | DAY 57 | n | 8 | |
| | | GOOD | 1 (12.5%) | |
| | | MODERATE | 2 (25.0%) | |
| | | NO | 5 (62.5%) | |
| | FOLLOW UP | n | 8 | |
| | | GOOD | 2 (25.0%) | |
| | | MODERATE | 2 (25.0%) | |
| | | NO | 4 (50.0%) | |

*all placebo

PK/PD Interim Analysis

IL6R304, sIL-6R and fibrinogen levels were modeled by nonlinear mixed effects modeling using NONMEM version 7.1.0 double precision (ICON Development Solutions, South County Business Park Leopardstown Dublin 18, Ireland).

The approach used for the interim analysis was sequential: first a pharmacokinetic model was developed to describe the drug IL6R304 profiles, then the individual predicted pharmacokinetic parameters were used as an input to the sIL-6R PK/PD model.

Pharmacokinetic Model

The estimation method used in the pharmacokinetic model was the first order conditional estimation with interaction (FOCEI). Prior to modeling, the drug levels were log-transformed. An exponential error model (additive in the log scale) was assumed for residual variability.

In the study population, the pharmacokinetics of IL6R304 were adequately characterized by a bi-compartmental model with a linear (non-target related) and non-linear (target related) clearance from the central compartment. Bodyweight was found as a significant covariate on clearance and was included allometrically in the pharmacokinetic model.

An indirect response model with a sigmoidal inhibitory effect on the elimination of the drug-target complex was used to relate IL6R304 plasma levels to the total sIL-6R plasma concentrations.

Overall, the estimated parameters were in good agreement with the parameters scaled from pre-clinical species and used for the dose-range selection of the clinical trial. The estimated $I_{max}$ was 94%, and the $IC_{50}$ 68 ng/mL. The only parameter which differed significantly from those previously used was the $V_{max}$ of the nonlinear clearance component of the model, currently found three times lower. This violated the earlier made assumption in which $V_{max}$ for IL6R304 was expected to be similar to $V_{max}$ for TCZ, due to the similar potency of the compounds to bind sIL-6R (in-house data).

The pharmacokinetic consequence of this finding is that the exposure to the drug is more prolonged than initially expected, and supports the evaluation of less frequent dosing regimens. The parameters derived from this model allowed to simulate the levels of IL6R304 expected after repeated dosing following various IL6R304 dosing regimens.

sIL-6R PK/PD Model

The estimation method used in the sIL-6R PK/PD model was the first order conditional estimation (FOCE). Non-transformed data were used, and an additive error model was assumed for residual variability.

An indirect PK/PD model of inhibition of plasma sIL-6R elimination adequately captured the observed biomarker profiles.

In this indirect response model, the rate of change of sIL-6R (Response, R) is described by:

$$\frac{dR}{dt} = Kin - Kout * \left[1 - Imax * \frac{C^n}{IC50^n + C^n}\right] * R$$

With $k_{in}$, the zero-order synthesis rate; R, the plasma sIL-6R level, $I_{max}$, the maximum inhibition ($1 < I_{max} < 0$); C, the concentration of IL6R304; IC50, the IL6R304 concentration at which half of the maximum effect is observed; n, the concentration-response shape factor; and $k_{out}$, the first order elimination rate constant of plasma sIL-6R.

The parameters derived from this model allowed to simulate the levels of sIL-6R expected following various IL6R304 dosing regimens.

Simulations

The PK and PK/PD models developed on the data available from the SAD part of the clinical trial were used to predict the expected exposure and biomarker profiles after repeated administration of the doses/dosing regimens proposed for the MAD part of the study. The prolonged pharmacokinetic and pharmacodynamic profiles suggested that different dosing regimens as those initially planned could be used. With an estimated $t_{1/2}$ of 17 d (similar to that of albumin), the pharmacokinetic profile of IL6R304 was expected to allow for a Q4W or Q8W dosing regimen. Three dose levels/regimens were selected for the MAD phase of the study:

1 mg/kg Q4W
3 mg/kg Q4W
6 mg/kg Q8W

The PK/PD model developed to describe the IL6R304/sIL-6R relationship, and the ones back-engineered from TCZ models reported in the literature (Levi et al. 2012, J. Clin. Pharmacol. February 14. [Epub ahead of print]; Gibiansky and Frey 2012, J. Pharmacokinet. Pharmacodyn. 39(1):5-16; Zhang and Peck 2011, Expert Rev. Clin. Pharmacol. 4(5): 539-55) were used to simulate the expected biomarker levels and clinical response during the MAD part of the study at the selected dose-regimens, and to compare them with TCZ. IL6R304 plasma levels of 1000 typical individuals expected after repeated drug administration were simulated, together with the corresponding sIL-6R profiles. FIGS. 2 and 3 illustrate respectively the median IL6R304 and sIL-6R profiles expected at the three proposed doses/dosing regimens.

The effects expected at a dose of 6 mg/kg Q8W IL6R304 would be comparable to TCZ 8 mg/kg, while an improved effect is expected at a dose of 3 mg/kg Q4W.

Discussion:

The pharmacokinetic profiles of IL6R304 observed in this first clinical trial appeared more sustained than predicted based on preclinical data from monkeys, allometrically scaled, and combined with reasonable assumptions.

This discrepancy between the observed and the model-based simulations of IL6R304-time profiles was attributed to an estimated 3-fold lower Vmax of the non-linear clearance pathway relative to that anticipated based on preclinical data (4.5 μg/h·kg) (see Table B-3).

Conclusions for the SAD Study:

Single i.v. administration of IL6R304 up to 6 mg/kg was safe and well tolerated in RA patients.

No deaths or treatment-related serious adverse events (SAEs) occurred, and a maximum tolerated dose (MTD) has not been reached.

The pharmacokinetics of IL6R304 appear non-linear, due to a saturable target-dependent CL component. However the exposure to the drug is more sustained than expected, due to a target-mediated clearance less efficient than predicted from preclinical data and clinical data from TCZ.

The corresponding biomarker profiles (sIL-6R) appear consequently also more prolonged than expected. An almost complete inhibition of the elimination of sIL-6R is predicted leading to sIL-6R levels in the range or higher than the target level of 400 ng/mL.

TABLES

TABLE A-1

Protein sequences of improved Nanobodies (with FR and CDR sequences indicated)

| Nanobody | SEQ ID | FR1 | SEQ ID | CDR 1 | SEQ ID | FR2 | SEQ ID | CDR 2 | SEQ ID | FR3 | SEQ ID |
|---|---|---|---|---|---|---|---|---|---|---|---|
| PMP7F4 | 7 | EVQLVESGGGLVQPGGSL RLSCAASGTTFK | 11 | VNVMA | 18 | WYRQAPGKG RELVA | 20 | GIINGGSTTYAD SVKG | 27 | RFTISRDNAKNTLYLQM NSLRPEDTAVYYCAF | 29 |
| PMP7C4 | 2 | EVQLVESGGGLVQPGGSL RLSCAASGTTFR | 12 | INVMA | 18 | WYRQAPGKG RELVA | 20 | GIITNGSTSYAD SVKG | 22 | RFTISRDNAKNTLYLQM NSLRPEDTAVYYCAF | 29 |
| PMP7D6 | 3 | EVQLVESGGGLVQPGGSL RLSCAASGSIFR | 13 | VNVMA | 18 | WYRQAPGKG RELVA | 20 | AVINGGTTTYA DSVKG | 23 | RFTISRDNAKNTLYLQM NSLRPEDTAVYYCAF | 29 |
| PMP7G7 | 4 | EVQLVESGGGLVQPGGSL RLSCAASGTTFK | 11 | INIMA | 19 | WYRQAPGKG RELVA | 20 | GVITGGNTTYA DSVKG | 24 | RFTISRDNAKNTLYLQM NSLRPEDTAVYYCAF | 29 |
| PMP7G8 | 5 | EVQLVESGGGLVQPGGSL RLSCAASGSTFR | 14 | INVMA | 17 | WYRQAPGKG RELVA | 20 | GVINDGSTTYA DSVKG | 25 | RFTISRDNAKNTLYLQM NSLRPEDTAVYYCAF | 29 |
| PMP20F6 | 6 | EVQLVESGGGLVQPGGSL RLSCAASGSVFK | 15 | INVMA | 17 | WYRQAPGKG RELVA | 20 | GIVSGGSTSYA DSVKG | 26 | RFTISRDNAKNTLYLQM NSLRPEDTAVYYCAF | 29 |
| PMP20A11 | 1 | EVQLVESGGGLVQPGGSL RLSCAASGSVFK | 15 | INVMA | 17 | WYRQAPGKG RELVA | 20 | GIISGGSTSYAD SVKG | 21 | RFTISRDNAKNTLYLQM NSLRPEDTAVYYCAF | 29 |
| PMP20E10 | 8 | EVQLVESGGGLVQPGGSL RLSCAASGSVFK | 15 | INVMA | 17 | WYRQAPGKG RELVA | 20 | GIVSGGSTSYA DSVKG | 26 | RFTISRDNAKNTLYLQM NSLRPEDTAVYYCAF | 29 |
| PMP21A10 | 9 | EVQLVESGGGLVQPGGSL RLSCAASGSIFK | 16 | INVMA | 17 | WYRQAPGKG RELVA | 20 | GIVTGGSTSYA DSVKG | 28 | RFTISRDNAKNTLYLQM NSLRPEDTAVYYCAF | 29 |
| PMP21D11 | 10 | EVQLVESGGGLVQPGGSL RLSCAASGSVFK | 15 | INVMA | 17 | WYRQAPGKG RELVA | 20 | GIVTGGSTSYA DSVKG | 28 | RFTISRDNAKNTLYLQM NSLRPEDTAVYYCAF | 29 |

TABLE A-1-continued

Protein sequences of improved Nanobodies (with FR and CDR sequences indicated)

| Nanobody | CDR 3 | SEQ ID | FR4 | SEQ ID |
|---|---|---|---|---|
| PMP7F4 | VTTNSDYDLGRDY | 32 | WGQGTLVTVSS | 33 |
| PMP7C4 | VTTNSDYDLGRDY | 32 | WGQGTLVTVSS | 33 |
| PMP7D6 | VTTNSDYDLGRDY | 32 | WGQGTLVTVSS | 33 |
| PMP7G7 | VTTNSDYDLGRDY | 32 | WGQGTLVTVSS | 33 |
| PMP7G8 | VTTNSDYDLGRDY | 32 | WGQGTLVTVSS | 33 |
| PMP20F6 | ITTNSDYDLGRRY | 31 | WGQGTLVTVSS | 33 |
| PMP20A11 | ITTESDYDLGRRY | 30 | WGQGTLVTVSS | 33 |
| PMP20E10 | ITTESDYDLGRRY | 30 | WGQGTLVTVSS | 33 |
| PMP21A10 | ITTESDYDLGRRY | 30 | WGQGTLVTVSS | 33 |
| PMP21D11 | ITTESDYDLGRRY | 30 | WGQGTLVTVSS | 33 |

TABLE A-2

Protein sequences of improved Nanobodies

PMP7F4, SEQ ID NO: 7
EVQLVESGGGLVQPGGSLRLSCAASGTTFKVNVMAWYRQAPGKGRELVAG
IINGGSTTYADSVKGRFTISRDNAKNTLYLQMNSLRPEDTAVYYCAFVTT
NSDYDLGRDYWGQGTLVTVSS

PMP7C4, SEQ ID NO: 2
EVQLVESGGGLVQPGGSLRLSCAASGTTFRINVMAWYRQAPGKGRELVAG
IITNGSTSYADSVKGRFTISRDNAKNTLYLQMNSLRPEDTAVYYCAFVTT
NSDYDLGRDYWGQGTLVTVSS

PMP7D6, SEQ ID NO: 3
EVQLVESGGGLVQPGGSLRLSCAASGSIFRVNVMAWYRQAPGKGRELVAA
VINGGTTTYADSVKGRFTISRDNAKNTLYLQMNSLRPEDTAVYYCAFVTT
NSDYDLGRDYWGQGTLVTVSS

PMP7G7, SEQ ID NO: 4
EVQLVESGGGLVQPGGSLRLSCAASGTTFKINIMAWYRQAPGKGRELVAG
VITGGNTTYADSVKGRFTISRDNAKNTLYLQMNSLRPEDTAVYYCAFVTT
NSDYDLGRDYWGQGTLVTVSS

PMP7G8, SEQ ID NO: 5
EVQLVESGGGLVQPGGSLRLSCAASGSTFRINVMAWYRQAPGKGRELVAG
VINDGSTTYADSVKGRFTISRDNAKNTLYLQMNSLRPEDTAVYYCAFVTT
NSDYDLGRDYWGQGTLVTVSS

PMP20F6, SEQ ID NO: 6
EVQLVESGGGLVQPGGSLRLSCAASGSVFKINVMAWYRQAPGKGRELVAG
IVSGGSTSYADSVKGRFTISRDNAKNTLYLQMNSLRPEDTAVYYCAFITT
NSDYDLGRRYWGQGTLVTVSS

PMP20A11, IL6R300, SEQ ID NO: 1
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSS

PMP20E10, SEQ ID NO: 8
EVQLVESGGGLVQPGGSLRLSCAASGSVFKINVMAWYRQAPGKGRELVAG
IVSGGSTSYADSVKGRFTISRDNAKNTLYLQMNSLRPEDTAVYYCAFITT
ESDYDLGRRYWGQGTLVTVSS

PMP21A10, SEQ ID NO: 9
EVQLVESGGGLVQPGGSLRLSCAASGSIFKINVMAWYRQAPGKGRELVAG
IVTGGSTSYADSVKGRFTISRDNAKNTLYLQMNSLRPEDTAVYYCAFITT
ESDYDLGRRYWGQGTLVTVSS

PMP21D11, SEQ ID NO: 10
EVQLVESGGGLVQPGGSLRLSCAASGSVFKINVMAWYRQAPGKGRELVAG
IVTGGSTSYADSVKGRFTISRDNAKNTLYLQMNSLRPEDTAVYYCAFITT
ESDYDLGRRYWGQGTLVTVSS

TABLE A-3

Protein sequences of preferred polypeptides of the invention

IL6R304, SEQ ID NO: 34
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGSEVQLVESGGGLVQPGNSLRL
SCAASGFTFSSFGMSWVRQAPGKGLEWVSSISGSGSDTLYADSVKGRFTI
SRDNAKTTLYLQMNSLRPEDTAVYYCTIGGSLSRSSQGTLVTVSS

IL6R305, SEQ ID NO: 35
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSEVQLVESGGGLVQPGGSLRL
SCAASGSVFKINVMAWYRQAPGKGRELVAGIISGGSTSYADSVKGRFTIS
RDNAKNTLYLQMNSLRPEDTAVYYCAFITTESDYDLGRRYWGQGTLVTVS
SGGGGSGGGSEVQLVESGGGLVQPGNSLRLSCAASGFTFSSFGMSWVRQA
PGKGLEWVSSISGSGSDTLYADSVKGRFTISRDNAKTTLYLQMNSLRPED
TAVYYCTIGGSLSRSSQGTLVTVSS

TABLE A-3-continued

Protein sequences of preferred polypeptides of the invention

IL6R306, SEQ ID NO: 36
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGSEVQLVESGGGLVQPGNSLRL
SCAASGFTFSSFGMSWVRQAPGKGLEWVSSISGSGSDTLYADSVKGRFTI
SRDNAKTTLYLQMNSLRPEDTAVYYCTIGGSLSRSSQGTLVTVSSGGGGS
GGGSEVQLVESGGGLVQPGGSLRLSCAASGSVFKINVMAWYRQAPGKGRE
LVAGIISGGSTSYADSVKGRFTISRDNAKNTLYLQMNSLRPEDTAVYYCA
FITTESDYDLGRRYWGQGTLVTVSS

TABLE A-4

Preferred, but non-limiting examples of albumin-binding Nanobodies

ALB-1, SEQ ID NO: 37
AVQLVESGGGLVQPGNSLRLSCAASGFTFRSFGMSWVRQAPGKEPEWVSS
ISGSGSDTLYADSVKGRFTISRDNAKTTLYLQMNSLKPEDTAVYYCTIGG
SLSRSSQGTQVTVSS

ALB-8(humanized ALB-1), SEQ ID NO: 38
EVQLVESGGGLVQPGNSLRLSCAASGFTFSSFGMSWVRQAPGKGLEWVSS
ISGSGSDTLYADSVKGRFTISRDNAKTTLYLQMNSLRPEDTAVYYCTIGG
SLSRSSQGTLVTVSS ALB-2, SEQ ID NO: 39
AVQLVESGGGLVQGGGSLRLACAASERIFDLNLMGWYRQGPGNERELVAT
CITVGDSTNYADSVKGRFTISMDYTKQTVYLHMNSLRPEDTGLYYCKIRR
TWHSELWGQGTQVTVSS

TABLE A-5

Sequence listing of linkers

| Linker | SEQ ID NO: | Sequences |
|---|---|---|
| 5GS | 40 | GGGGS |
| 7GS | 41 | SGGSGGS |
| GS8 | 42 | GGGGSGGGS |
| 9GS | 43 | GGGGSGGGS |
| 10GS | 44 | GGGGSGGGGS |
| 15GS | 45 | GGGGSGGGGSGGGGS |
| 18GS | 46 | GGGGSGGGGSGGGGGGS |

TABLE A-5-continued

Sequence listing of linkers

| Linker | SEQ ID NO: | Sequences |
|---|---|---|
| 20GS | 47 | GGGGSGGGGSGGGGSGGGGS |
| 25GS | 48 | GGGGSGGGGSGGGGSGGGGSGGGGS |
| 30GS | 49 | GGGGSGGGGSGGGGSGGGGSGGGGSGGGGS |
| 35GS | 50 | GGGGSGGGGSGGGGSGGGGSGGGGSGGGGSGGGGS |
| G1 hinge | 51 | EPKSCDKTHTCPPCP |
| 9GS-G1 hinge | 52 | GGGGSGGGSEPKSCDKTHTCPPCP |
| Llama upper long hinge region | 53 | EPKTPKPQPAAA |
| G3 hinge | 54 | ELKTPLGDTTHTCPRCPEPKSCDTPPPCPRCPEPKSCDTPPPCPRCPEPKSCDTPPPCPRCP |
| Ala | 55 | AAA |

The entire contents of all of the references (including literature references, issued patents, published patent applications, and co-pending patent applications) cited throughout this application are hereby expressly incorporated by reference, in particular for the teaching that is referenced herein.

EQUIVALENTS

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for inhibiting IL-6 mediated signaling in a subject comprising administering to the subject a polypeptide that specifically binds IL-6R and that consists of the amino acid sequence set forth in SEQ ID NO: 34, wherein the amount of the polypeptide administered is effective:
- to increase total sIL-6R levels in serum to at least 400 ng/ml and to maintain total sIL-6R levels in serum of at least 400 ng/ml;
- to increase total IL-6 levels in serum to at least 40 pg/ml and to maintain total IL-6 levels in serum of at least 40 pg/ml;
- to reduce C-reactive protein (CRP) levels in serum below 10 mg/l and to maintain CRP levels in serum below 10 mg/l;
- to reduce CRP levels in serum by 50% or more compared to baseline levels and to maintain CRP levels in serum at 50% or more reduction compared to baseline levels;
- to reduce Erythrocytes Sedimentation Rate (ESR) levels in serum by 30% or more compared to baseline levels and to maintain ESR levels in serum at 30% or more reduction compared to baseline levels;
- to reduce fibrinogen levels in serum by 30% or more compared to baseline levels and to maintain fibrinogen levels in serum at 30% or more reduction compared to baseline levels; and/or
- to reduce serum amyloid A levels by 30% or more compared to baseline levels and to maintain serum amyloid A levels at 30% or more reduction compared to baseline levels;
- wherein the polypeptide is administered in an amount from 1 mg/kg to 10 mg/kg every 2 to 4 weeks; and
- wherein the polypeptide is not administered in an amount from 3 mg/kg to 6 mg/kg every 4 weeks.

2. The method of claim 1, wherein the subject is suffering from an inflammatory disease and/or disorder.

3. The method of claim 1, wherein the subject is suffering from rheumatoid arthritis.

4. The method of claim 1, wherein the polypeptide is administered in an amount from 1 mg/kg to 2 mg/kg.

5. The method of claim 4, wherein the polypeptide is administered in an amount of 1 mg/kg.

6. The method of claim 4, wherein the polypeptide is administered in an amount of 2 mg/kg.

7. The method of claim 1, wherein the polypeptide is administered in an amount from 3 mg/kg to 6 mg/kg.

8. The method of claim 7, wherein the polypeptide is administered in an amount of 3 mg/kg.

9. The method of claim 7, wherein the polypeptide is administered in an amount of 6 mg/kg.

10. The method of claim 1, wherein the polypeptide is administered as a multiple dose.

11. The method of claim 10, wherein the polypeptide is administered every 4 weeks.

12. The method of claim 11, wherein the polypeptide is administered at 3 mg/kg every 4 weeks.

13. The method of claim 11, wherein the polypeptide is administered at 6 mg/kg every 4 weeks.

14. The method of claim 10, wherein the polypeptide is administered every 2 weeks.

15. The method of claim 14, wherein the polypeptide is administered at 1 mg/kg every 2 weeks.

16. The method of claim 2, wherein the inflammatory disease is selected from rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma, and autoimmune insulin-dependent diabetes mellitus.

17. The method of claim 1, wherein the subject is suffering from a disease and/or disorder selected from sepsis, cancer, bone resorption, cachexia, psoriasis, mesangial proliferative glomerulonephritis, Kaposi's sarcoma, and AIDS-related lymphoma.

18. The method of claim 17, wherein the cancer is selected from multiple myeloma disease (MM), renal cell carcinoma (RCC), plasma cell leukaemia, lymphoma, B-lymphoproliferative disorder (BLPD) and prostate cancer.

19. The method of claim 17, wherein the bone resorption is osteoporosis.

* * * * *